(12) United States Patent
Qi et al.

(10) Patent No.: US 9,623,083 B2
(45) Date of Patent: Apr. 18, 2017

(54) METHOD TO SCREEN FOR AN ACTIVATOR OF ADIPOSE-RESIDENT NK CELLS

(75) Inventors: Ling Qi, Ithaca, NY (US); Yewei Ji, Ithaca, NY (US)

(73) Assignee: Cornell University, Ithaca, NY (US)

( * ) Notice: Subject to any disclaimer, the term of this patent is extended or adjusted under 35 U.S.C. 154(b) by 282 days.

(21) Appl. No.: 14/241,482

(22) PCT Filed: Aug. 30, 2012

(86) PCT No.: PCT/US2012/052967
§ 371 (c)(1),
(2), (4) Date: Feb. 27, 2014

(87) PCT Pub. No.: WO2013/033283
PCT Pub. Date: Mar. 7, 2013

(65) Prior Publication Data
US 2014/0193361 A1 Jul. 10, 2014

Related U.S. Application Data

(60) Provisional application No. 61/528,995, filed on Aug. 30, 2011, provisional application No. 61/855,455, filed on Oct. 7, 2011.

(51) Int. Cl.
| | |
|---|---|
| G01N 33/53 | (2006.01) |
| A61K 38/20 | (2006.01) |
| G01N 33/50 | (2006.01) |
| A61K 38/19 | (2006.01) |
| A61K 31/7032 | (2006.01) |
| C12N 5/0783 | (2010.01) |
| A61K 31/7028 | (2006.01) |
| C12Q 1/68 | (2006.01) |
| G01N 33/68 | (2006.01) |

(52) U.S. Cl.
CPC ...... *A61K 38/2086* (2013.01); *A61K 31/7028* (2013.01); *A61K 31/7032* (2013.01); *A61K 38/19* (2013.01); *A61K 38/208* (2013.01); *A61K 38/2026* (2013.01); *A61K 38/2066* (2013.01); *C12N 5/0646* (2013.01); *C12Q 1/6851* (2013.01); *G01N 33/505* (2013.01); *G01N 33/5088* (2013.01); *G01N 33/6863* (2013.01); *G01N 33/6869* (2013.01)

(58) Field of Classification Search
CPC .................................................. G01N 33/6863
See application file for complete search history.

(56) References Cited

U.S. PATENT DOCUMENTS

2004/0171557 A1  9/2004  Iian et al.

FOREIGN PATENT DOCUMENTS

| JP | 2006-288382 A | 10/2006 |
| WO | 2006/029010 A2 | 3/2006 |
| WO | 2009/111889 A1 | 9/2009 |
| WO | 2011/052919 A2 | 5/2011 |

OTHER PUBLICATIONS

Gordon, S., et al., "Alternative activation of macrophages: mechanism and functions", Immunity, May 28, 2010, pp. 593-604, vol. 32.
Bouhlel, M.A., et al., "PPARgamma activation primes human monocytes into alternative M2 macrophages with anti-inflammatory properties", Cell Metabolism, Aug. 2007, pp. 137-143, vol. 6.
Kang, K., et al., "Adipocyte-derived Th2 cytokines and myeloid PPARdelta regulate macrophage polarization and insulin sensitivity", Cell Metabolism, Jun. 2008, pp. 485-495, vol. 7.
Lumeng, C.N., et al., "Obesity induces a phenotypic switch in adipose tissue macrophage polarization", The Journal of Clinical Investigation, Jan. 2007, pp. 175-184, vol. 117, No. 1.
Zeyda, M., et al., "Human adipose tissue macrophages are of an anti-inflammatory phenotype but capable of excessive pro-inflammatory mediator production", International Journal of Obesity, Jun. 26, 2007, pp. 1420-1428, vol. 31, Nature Publishing Group.
Bourlier,V., et al., "Remodeling phenotype of human subcutaneous adipose tissue macrophages", Circulation, Jan. 28, 2008, pp. 806-815, vol. 117, American Heart Association, Dallas, TX.
Shaul, M.E., et al., "Dynamic, M2-like remodeling phenotypes of CD11c+ adipose tissue macrophages during high-fat diet—induced obesity in mice", Diabetes, May 2010, pp. 1171-1181, vol. 59.
Samuel, V.T., et al., "Mechanism of hepatic insulin resistance in non-alcoholic fatty liver disease", Journal of Biological Chemistry, May 27, 2004, pp. 32345-32353, vol. 279, No. 31.
Kraegen, E.W., et al., "Development of muscle insulin resistance after liver insulin resistance in high-fat-fed rats", Diabetes, Nov. 1991, pp. 1397-1403, vol. 40.
Kleeman,R., et al., "Time-resolved and tissue-specific systems analysis of the pathogenesis of insulin resistance", PLoS ONE, Jan. 21, 2010, pp. 1-17, e8817, vol. 5, issue 1.
Xia, S., et al., "Gr-1+ CD11b+ myeloid-derived suppressor cells suppress inflammation and promote insulin sensitivity in obesity", Journal of Biological Chemistry, Jul. 1, 2011, pp. 23591-23599, vol. 289, No. 26.
Bolstad, B.M., et al., A comparison of normalization methods for high density oligonucleotide array data based on variance and bias. Bioinfonnatics, 2003, pp. 185-193, vol. 19, No. 2.
Irizarry, R.A., et al., "Summaries of Affymetrix GeneChip probe level data", Nucleic Acids Research, 2003, e15, pp. 1-8, vol. 31, No. 4.
Dai, M., et al., "Evolving gene/transcript definitions significantly alter the interpretation of GeneChip data", Nucleic Acids Research, Nov. 10, 2005, e175, pp. 1-9, vol. 33, No. 20.

(Continued)

*Primary Examiner* — Prema Mertz
(74) *Attorney, Agent, or Firm* — Scully Scott Murphy & Presser

(57) ABSTRACT

Obesity is associated with a state of chronic low-grade inflammation and the present invention establishes that adipose-resident natural killer T (NKT) cells attenuate inflammation in adipose tissue and improves systemic glucose homeostasis in mice at different stages of obesity. Accordingly, the present invention provides methods of treating type-2 diabetes or those at risk for type-2 diabetes using activators of adipose-resident NKT cells. Such activators include particular glycolipids (e.g., a-galactosylceramide and its analogs other than sulfated analogs) and cytokines that promote M2 macrophage polarization. The invention also includes methods to screen for activators of adipose-resident NKT cells.

4 Claims, 37 Drawing Sheets

(56) References Cited

OTHER PUBLICATIONS

Sartor, M.A., et al., "Intensity-based hierarchical Bayes method improves testing for differentially expressed genes in microarray experiments", BMC Bioinformatics, Dec. 2006, pp. 1-9, vol. 7, No. 538.

Saeed, A.I., et al., "TM4: a free, open-source system for microarray data management and analysis", Biotechniques, Feb. 2003, pp. 374-378, vol. 34, No. 2.

Bendelac, A., et al., "CD1 Recognition by Mouse NK1 + T Lymphocytes", Science, May 12, 1995, pp. 863-865, vol. 268.

Bendelac, A., "Positive Selection of Mouse NK1 + T Cells by CD1-expressing Cortical Thymocytes", J. Exp. Med, Dec. 1995, pp. 2091-2096, vol. 182.

Kawano, T., et al., "CD1d-Restricted and TCR-Mediated Activation of Vα 14 NKT Cells by Glycosylceramides", Science, Nov. 28, 1997, pp. 1626-1629, vol. 278.

Bai, L., et al., "Lysosomal recycling terminates CD1d-mediated presentation of short and polyunsaturated variants of the NKT cell lipid antigen αGalCer", Proc Natl Acad Sci USA 106, Jun. 23, 2009, pp. 10254-10259, vol. 106, No. 25.

Weisberg, S.P., et al., "Obseity is associated with macrophage accumulation in adipose tissue", The Journal of Clinical Investigation, Dec. 2003, pp. 1796-1808, vol. 112, No. 12.

Xu, H., et al., "Chronic inflammation in fat plays a crucial role in the development of obesity-related insulin resistance", The Journal of Clinical Investigation, Dec. 2003, pp. 1821-1830, vol. 112, No. 12.

Rausch, M.E., et al., "Obesity in C57BL/6J mice is characterized by adipose tissue hypoxia and cytotoxic T-cell infiltration", International Journal of Obesity, 2008, pp. 451-463, vol. 32.

Liu, J., et al., "Genetic deficiency and pharmacological stabilization of mast cells reduce diet-induced obesity and diabetes in mice", Nature Medicine, Aug. 2008, pp. 940-945, vol. 15, No. 8.

Odegaard, J.I., et al., "Alternative M2 Activation of Kupffer Cells by PPARδ Ameliorates Obesity-Induced Insulin Resistance", Cell Metalbolism, Jun. 2008, pp. 496-507, vol. 7.

Wu, D., et al., "Eosinophils Sustain Adipose Alternatively Activated Macrophages Associated with Glucose Homeostasis", Science, Apr. 8, 2011, pp. 243-247, vol. 332.

Schipper, H.S., et al., "Adipose tissue-resident immune cells: key players in immunometabolism", Trends in Endocrinology and Metabolism, Aug. 2012, pp. 407-415, vol. 23, No. 8.

Lynch, L., et al., "Invariant NKT cells and CD1d+ cells amass in human omentum and are depleted in patients with cancer and obesity", Eur. J. Immunol., 2009, pp. 1893-1901, vol. 39.

Kotas, M.A., et al., "Impact of CD1d Deficiency on Metabolism", PLoS ONE, Sep. 2011, pp. 1-17, e25478, vol. 6, issue 9.

Mantell, B.S., et al., "Mice Lacking NKT Cells but with a Complete Complement of CD8+ T-Cells Are Not Protected against the Metabolic Abnormalities of Diet-Induced Obesity", PLoS One, Jun. 2011, pp. 1-7, e19831, vol. 6, issue 6.

Ohmura, K., et al., "Natural Killer T Cells Are Involved in Adipose Tissues Inflammation and Glucose Intolerance in Diet-Induced Obese Mice", Arterioscler Thromb Vasc Biol., 2010, pp. 193-199, vol. 30.

Schmieg, J., et al., Glycolipid presentation to natural killer T cells differs in an organ-dependent fashion, Proc Natl Acad Sci USA, Jan. 25, 2005, pp. 1127-1132, vol. 102, No. 4.

Lee, P.T., et al., "Distinct Functional Lineages of Human Vα24 Natural Killer T Cells", J. Exp. Med., Mar. 4, 2002, pp. 637-641, vol. 195, No. 5.

Benlagha, K.., et al., "A Thymic Precursor to the NK T Cell Lineage", Science, Apr. 19, 2002, pp. 553-555, vol. 296.

Pellicci, D.G., et al., "A Natural Killer T (NKT) Cell Development Pathway Involving a Thymus-dependent NK1.1- CD4+ CD1d-dependent Precursor Stage", J. Exp. Med., Apr. 1, 2002, pp. 835-844, vol. 195, No. 7.

Brigl, M., et al., "Innate and cytokine-driven signals, rather than microbial antigens, dominate in natural killer T cell activation during microbial infection", The Journal of Experimental Medicine, May 9, 2011, pp. 1163-1177, vol. 208, No. 6.

Chawla, A., "Control of Macrophage Activation and Function by PPARs", Circulation Research, Jan. 4, 2010, pp. 1559-1569, vol. 106.

Marathe, C., et al., "Preserved glucose tolerance in high-fat-fed C57BL/6 mice transplanted with PPARγ-/-, PPARδ-/-, PPARγδ-/-, or LXRαβ-/- bone marrow", Journal of Lipid Research, 2009, pp. 214-224, vol. 50.

Giaccone, G., et al., "A Phase I Study of the Natural Killer T-Cell Ligand α-Galactosylceramide (KRN7000) in Patients with Solid Tumors", Clinical Cancer Research, Dec. 2002, pp. 3702-3709, vol. 8.

Sha, H., et al., "The IRE1α-XBP1 Pathway of the Unfolded Protein Response Is Required for Adipogenesis", Cell Metabolism, Jun. 3, 2009, pp. 556-564, vol. 9.

Wilson, M.T., et al., "The response of natural kill T cells to glycolipid antigens is characterized by surface receptor down-modulation and expansion", Proc Natl Acad Sci USA, Sep. 16, 2003, pp. 10913-10918, vol. 100, No. 19.

Kis, J., et al., "Reduced CD4+ subset and Th1 bias of the human iNKT cells in Type 1 diabetes mellitus", Journal of Leukocyte Biology, Mar. 2006, pp. 654-662, vol. 81.

Vijayanand, P., et al., "Invariant Natural Killer T Cells in Asthma and Chronic Obstructive Pulmonary Disease", The New England Journal of Medicine, Apr. 5, 2007, pp. 1410-1422, vol. 356.

Cerundolo, V., et al., "Harnessing invariant NKT cells in vaccination strategies", Nature Review Immunology, Jan. 2009, pp. 28-38, vol. 9.

Matthews, D.R., et al., "Homeostasis model assessment: insulin resistance and β-cell function from fasting plasma glucose and insulin concentrations in man", Diabetologia, 1985, pp. 412-419, vol. 28.

Beckman, E.M., et al., "Recognition of a lipid antigen by CD1-restricted α β+ T cells", Nature, 1994, pp. 691-694, vol. 372.

Bendalac, A., et al., "The Biology of NKT Cells", Annu. Rev. Immunol, 2007, pp. 297-336, vol. 25.

Berzins, S.T., et al., "Presumed guilty: natural killer T cell defects and human disease", Nature Reviews, Feb. 2011, pp. 131-142, vol. 11.

Brigl, M., et al., "Mechanism of CD1d-restricted natural killer T cell activation during microbial infection", Nature Immunology, Dec. 2003, pp. 1230-1237, vol. 4, No. 12.

Donath, M.Y., et al., "Type 2 diabetes as an inflammatory disease", Nature, Feb. 2011, pp. 98-107, vol. 11.

Feuerer, M., et al., "Lean, but not obese, fat enriched for a unique population of regulatory T cells that affect metabolic parameters", Nature Medicine, Aug. 2009, pp. 930-940, vol. 15, No. 8.

Godfrey, D.I., et al., "Raising the NKT family", Nature Immunology, Mar. 2010, vol. 11, No. 3, 197-206.

Hong, S., et al. ,"The natural T-cell ligand α-galactosylceramide prevents autoimmune diabetes in non-obese diabetic mice", Nature Medicine, Sep. 2001, pp. 1052-1056, vol. 7, No. 9.

Ishii, M., et al., "Epigenetic regulation of the alternatively activated macrophage phenotype", Blood, Oct. 8, 2009, pp. 3244-3254, vol. 114, No. 15.

Koller, B.H., et al., "Normal Development of Mice Deficient in β 2 M, MHC Class I Proteins, and CD8+ T Cells", Science, Jun. 8, 1990, New Series, pp. 1227-1230, vol. 248, No. 4960.

Kronenberg, M., "Toward an Understanding of NKT Cell Biology: Progress and Paradoxes", Annu. Rev. Immunol., 2005, pp. 877-900, vol. 26.

Miyamoto, K., et al., "A synthetic glycolipid prevents autoimmune encephalomyelitis by inducing T H 2 bias of natural killer T cells", Nature, Oct. 4, 2001, pp. 531-534, vol. 413.

Nishimura, S., et al., "CD8+ effector T cells contribute to macrophage recruitment and adipose tissue inflammation in obesity", Nature, Aug. 2009, pp. 914-921, vol. 15, No. 8.

Odegaard, J.I., et al., "Macrophage-specific PPARγ controls alternative activation and improves insulin resistance", Nature, Jun. 28, 2007, pp. 1116-1121, vol. 447.

(56) References Cited

OTHER PUBLICATIONS

Olefsky, J., et al., Macrophages, Inflammation, and Insulin Resistance, Annu. Rev. Physiol., 2010, pp. 219-246, vol. 72.

Porcelli, S., et al., "CD1b restricts the response of human CD4 8 T lymphocytes to a microbial antigen", Nature, Dec. 10, 1992, pp. 593-597, vol. 360.

Saeed, A.I., et al., "TM4 Microarray Software Suite", Methods in Enzymology, 2006, pp. 134-193, vol. 411.

Satoh, T., et al., "The Jmjd3-Irf4 axis regulates M2 macrophage polarization and host responses against helminth infection", Nature Immunology, Oct. 2010, pp. 936-945, vol. 11, No. 10.

Winer, D.A., et al., "B Cells promaote insulin resistance through modulation of T cells and production of pathogenic IgG antibodies", Nature Medicine, May 2011, pp. 610-618, vol. 17, No. 5.

Yoshimoto, T., etal., "Role of NK1.1 + T Cells in a T H 2 response and in Immunoglobulin E Production", Science, Dec. 15, 1995, New Series, pp. 1845-1847, vol. 270, No. 5243.

Zijlstra, M., et al., β2-Microglobulin deficient mice lack CD4-8+ cytolytic T cells, Nature, Apr. 19, 1990, pp. 742-746, vol. 344.

Kaminski, D.A., et al., "Adaptive immunity and adipose tissue biology", Trends Immunol., Oct. 2010, pp. 384-390, vol. 31, No. 10.

Szanto, A., et al., "STAT6 Transcription Factor is a Facilitator of the Nuclear Receptor PPARγ-Regulated Gene Expression in Macrophages and Dendritic Cells", Immunity 33, Nov. 24, 2010, pp. 699-712.

Bushard, K., "Sulphated galactosylceramide", Diabetologica, 2005, pp. 1007-1008, vol. 53.

Bushard, K., et al., "Involvement of sulfatide in beta cells and type 1 and type 2 diabetes", Diabetologica, 2005, pp. 1957-1962, vol. 48.

Gill, J.M.R., et al., "Ceramides: A new player in the inflammation-insulin resistance paradigm?", Diabetologica, 2009, pp. 2475-2477, vol. 52.

Guebre-Xabier, M., et al., "Altered Hepatic Lymphocyte Subpopulation in Obesity-Related Murine Fatty Livers: Potential Mechanism for Sensitization to Liver Damage", Hepatology, Mar. 2000, pp. 633-640.

Ji, Y., et al., "Activation of Natural Killer T Cells Promotes M2 Macrophage Polarization in Adipose Tissue and Improves Systemic Glucose Tolerance via the IL-4/STAT6 Signaling Axis in Obesity", JBC Papers in Press. Published on Mar. 6, 2012 as Manuscript M112.350066, Downloaded from www.jbc.org by guest, on Aug. 16, 2012, pp. 1-22.

Ji, Y., et al., Short-Term High-Fat Challenge Promotes Alternative Macrophage Polarization in Adipose Tissue via Natural Killer T Cells and Interleukin-4, JBC Papers in Press. Published on May 29, 2012 as Manuscript M112.371807, Downloaded from www.jbc.org by guest, on Aug. 9, 2012, pp. 1-21.

Ma, X., et al., "Probiotics Improve High Fat Diet-induced Hepatic Steatosis and Insulin resistance by Increasing Hepatic NKT cells", J. Hepatol., Nov. 2008, pp. 821-830, vol. 49, No. 5.

Margalit, M., et al., "Glucocerebroside Ameliorates the Metabolic Syndrome in OB/OB Mice", The Journal of Pharmacology and Experimental Therapeutics, 2006, pp. 105-110, vol. 319, No. 1.

Miyazaki, Y., et al., "Effect of High Fat Diet on NKT Cell Function and NKT Cell-mediated Regulation of Th1 Responses", Scandinavian Journal of Immunology 67, 2008, pp. 230-237.

Qi, Ling, Use Dietary Lipids to Treat Type-2 Diabetes, Division of Nutrition Sciences, Cornell University, Slide Presentation, pp. 1-24.

Roman-Gonzalez, A., et al., "Frequency and function of circulating invariant NKT cells in autoimmune diabetes mellitus and thyroid diseases in Colombian patients", Human Immunology, 2009, pp. 262-268, vol. 70.

Satoh, M., et al., "Type II NKT Cells Stimulate Diet-Induced Obesity by Mediating Adipose Tissue Inflammation, Steatohepatitis", PLoS ONE, Feb. 2012, e30568, pp. 1-12, vol. 7., issue 2.

Yang, L., et al., Endoplasmic reticulum stress, hepatocyte CD1d and NKT cell abnormalities in murine fatty livers, Laboratory Investigation, Sep. 2007, pp. 927-937, vol. 87.

Anonymous author, "KRN7000 applied to diabetes research", www.alpha-galcer.net/diabetesresearch.html, pp. 1-2.

Winer, S., et al., "Normalization of Obesity-Associated Insulin Resistance through Immunotherapy: CD4+ T Cells Control Glucose Homeostatisis", Nat. Med., Aug. 2009, pp. 921-929, vol. 15, No. 8.

International Search Report dated Dec. 6, 2012issued in International Application No. PCT/US2012/052967.

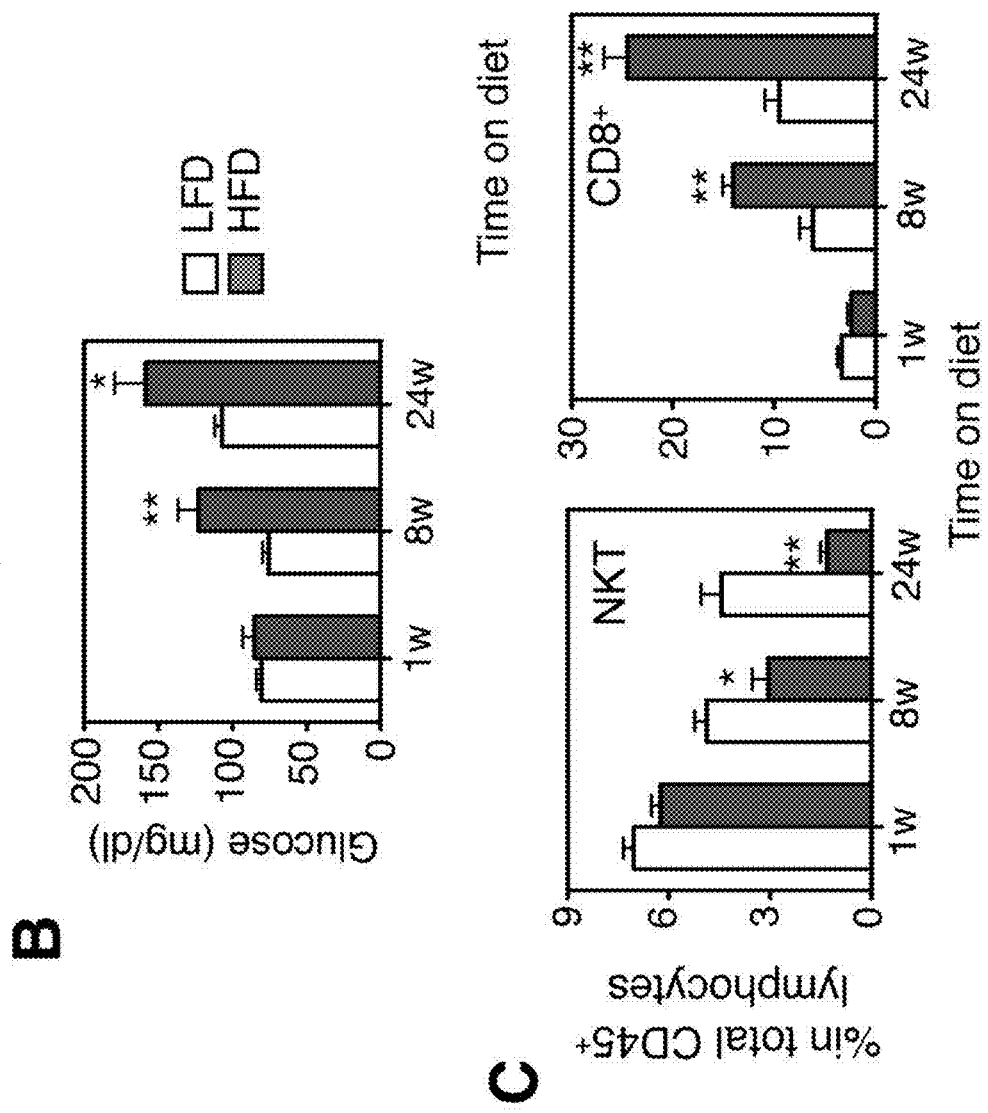
Figs. 2B-C

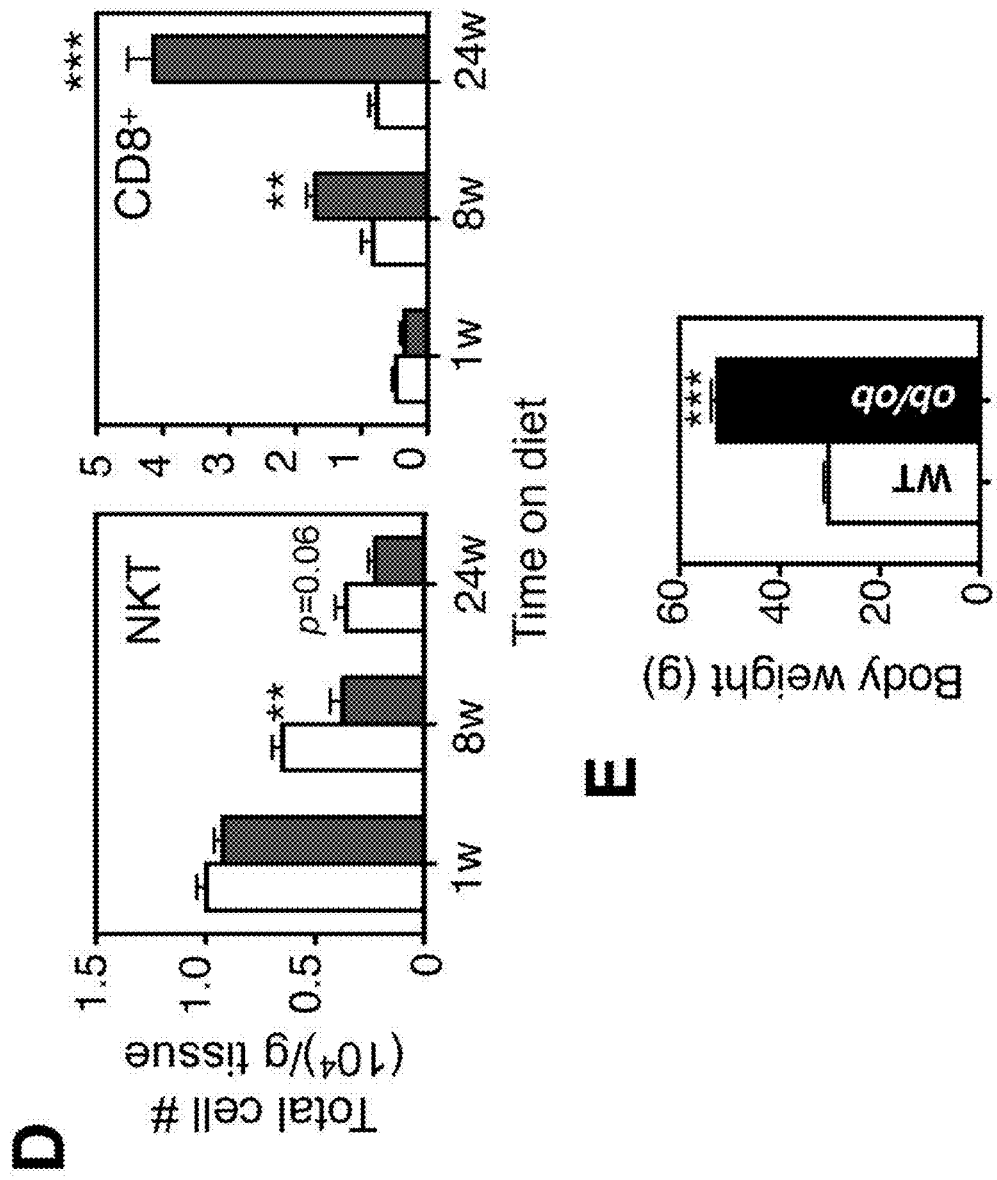
Figs. 2D-E

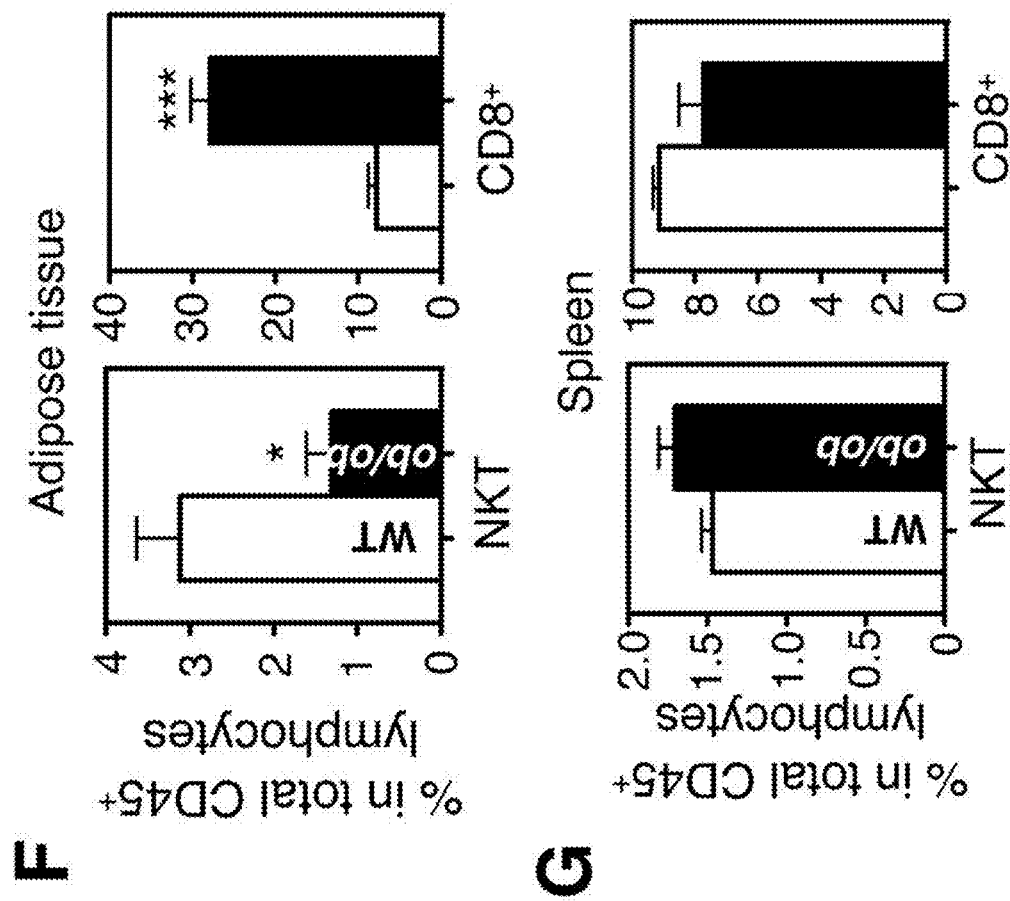
Figs. 2F-G

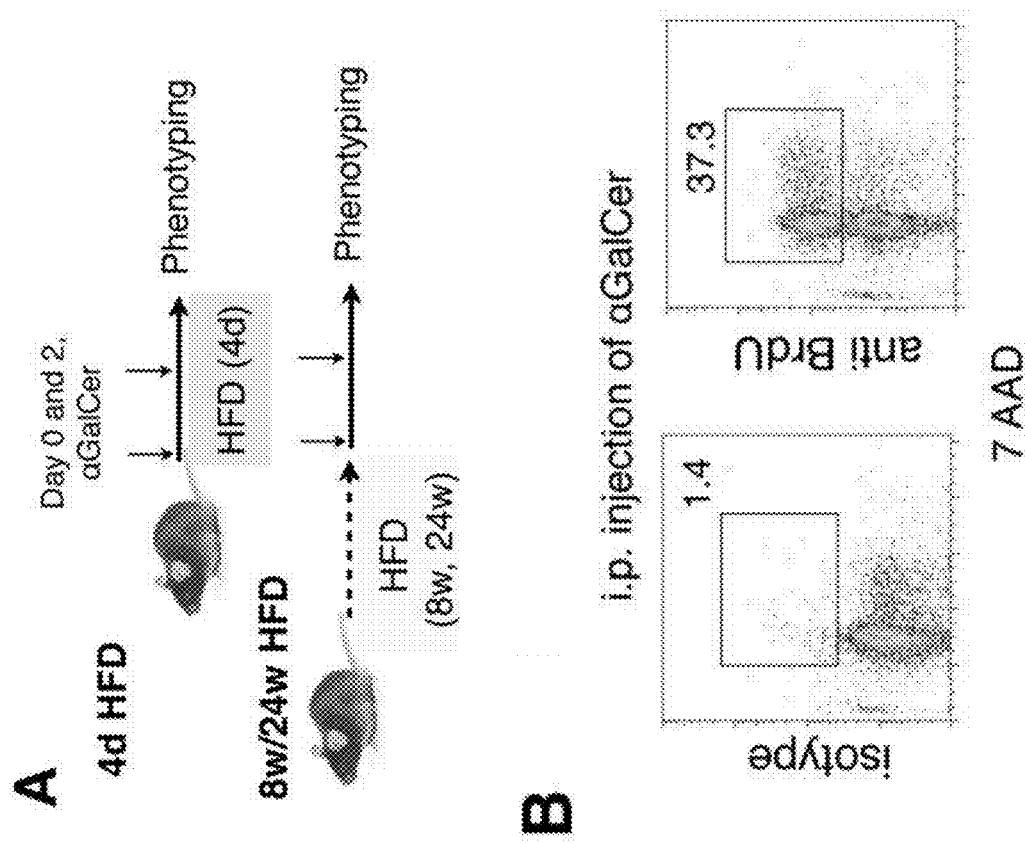
Figs. 3A-B

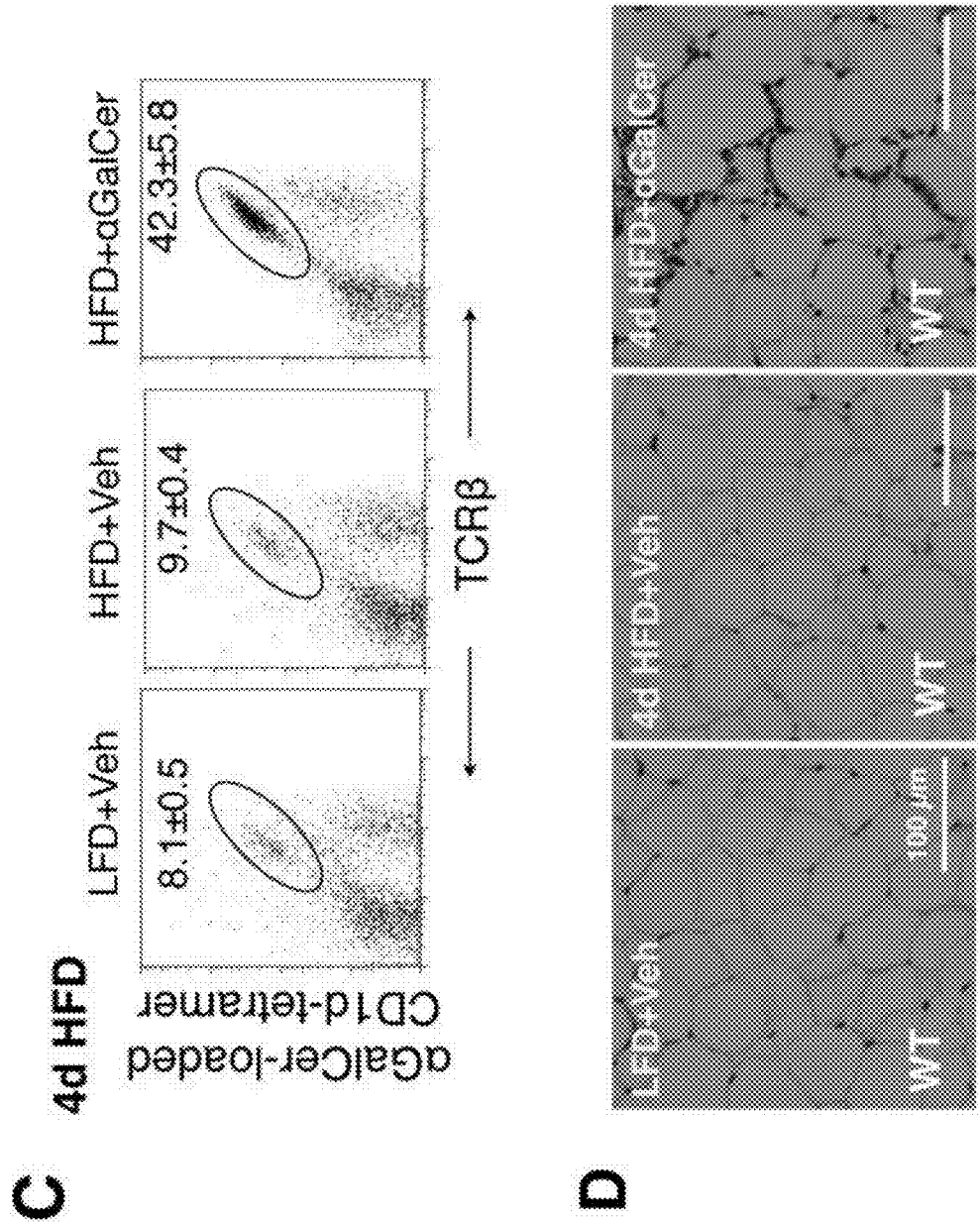
Figs. 3C-D

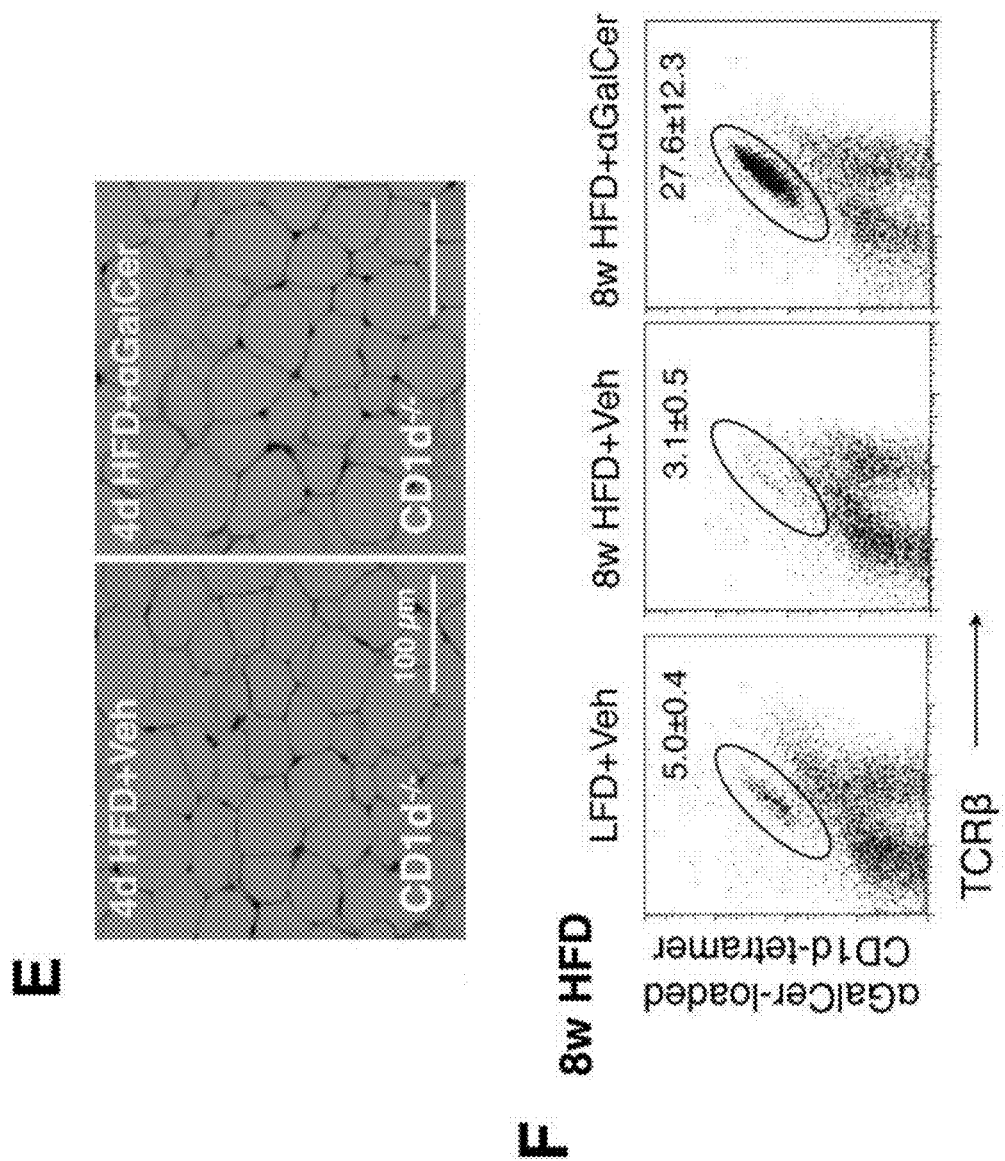
Figs. 3E-F

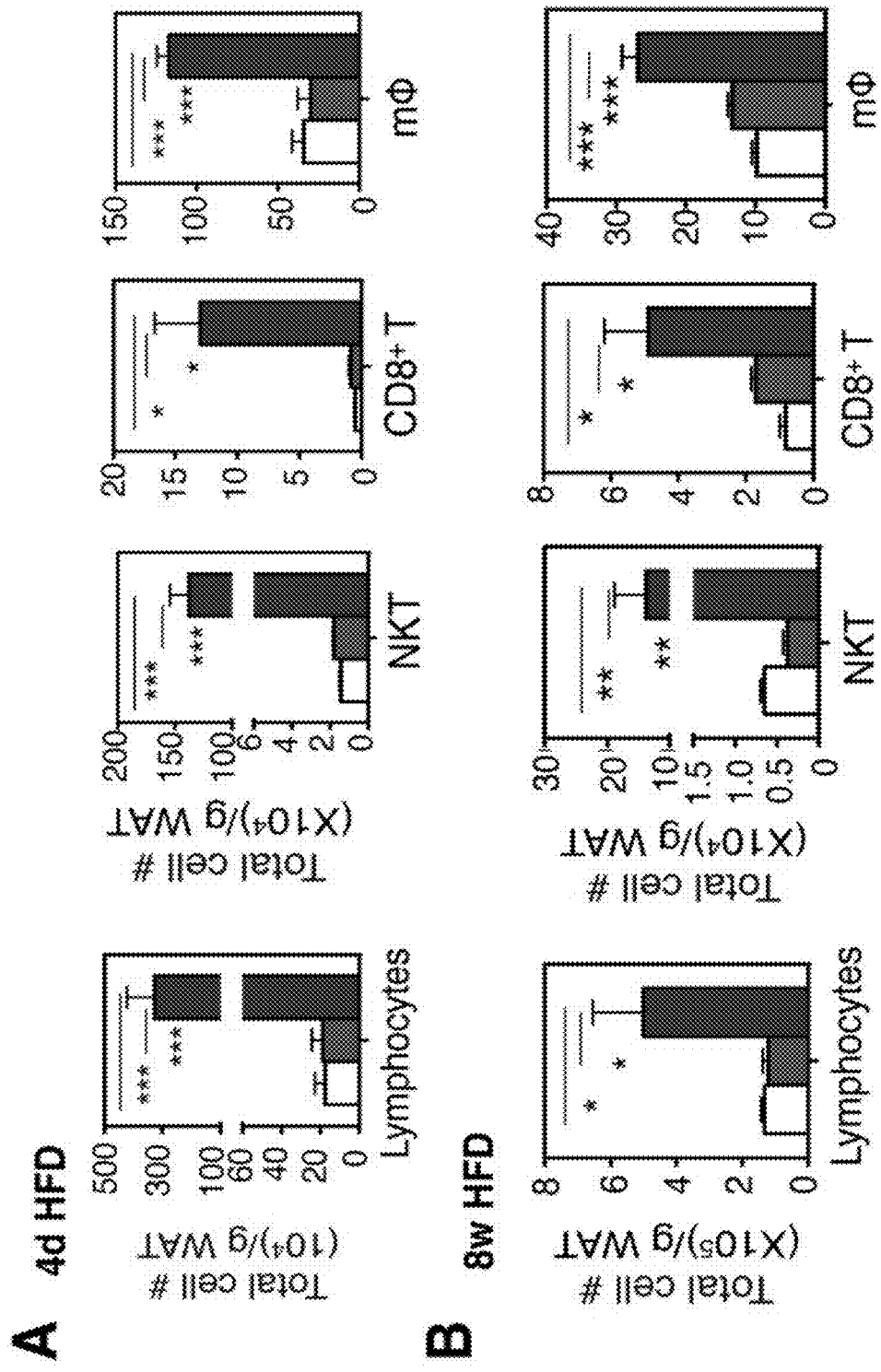
Figs. 5A-B

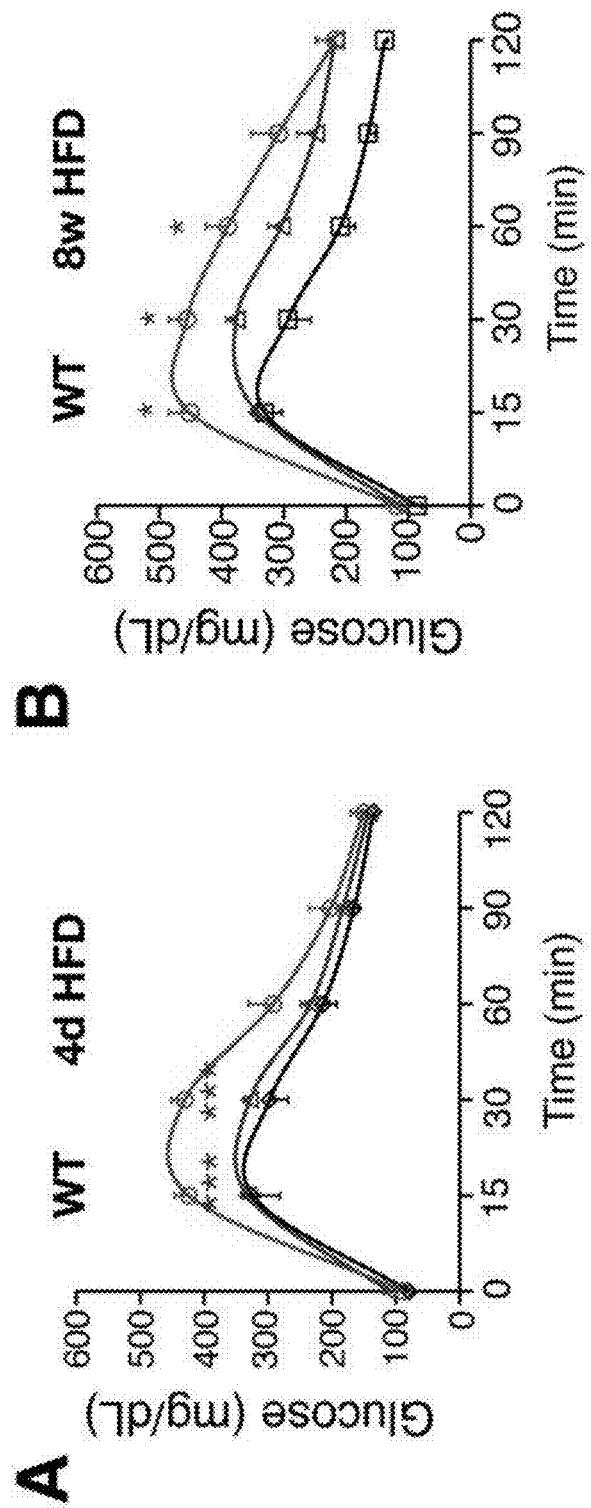
Figs. 6A-B

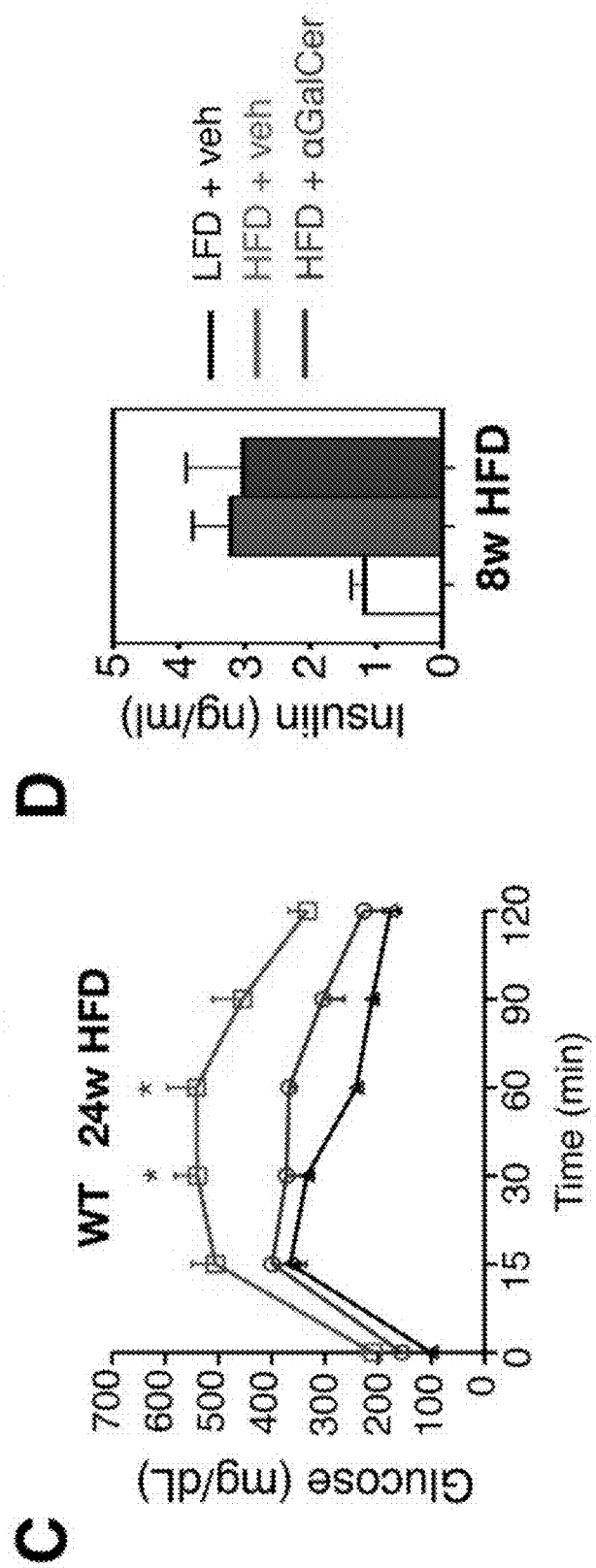
Figs. 6C-D

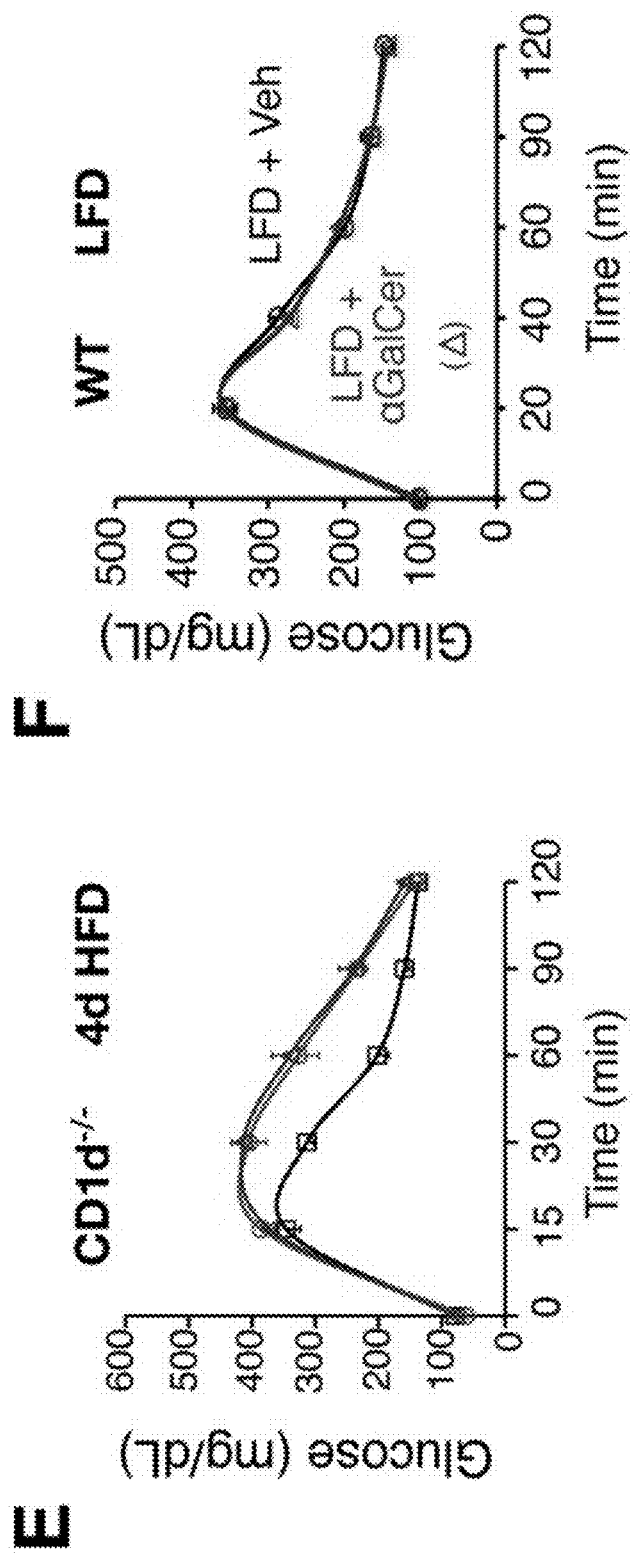
Figs. 6E-F

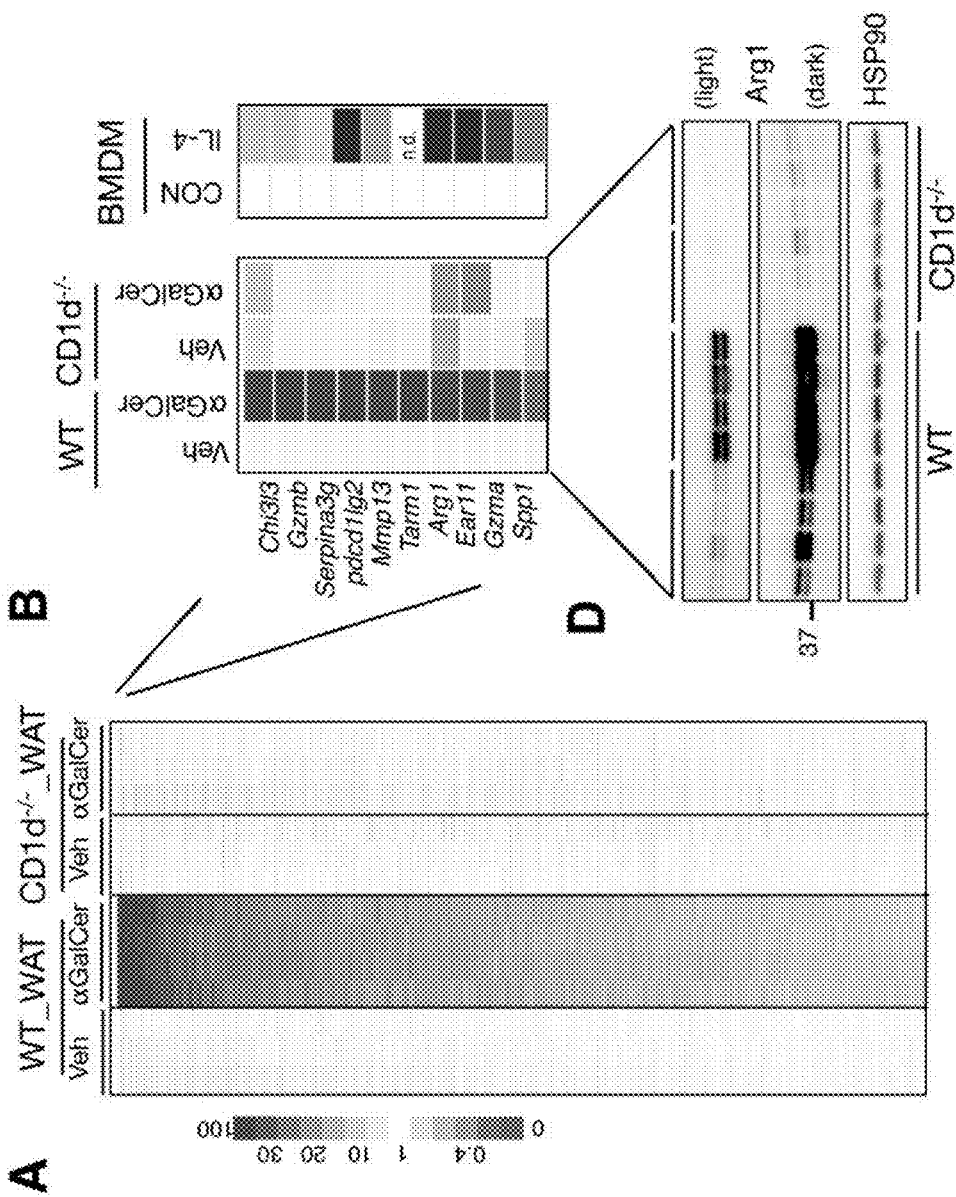
Figs. 9A, B, D

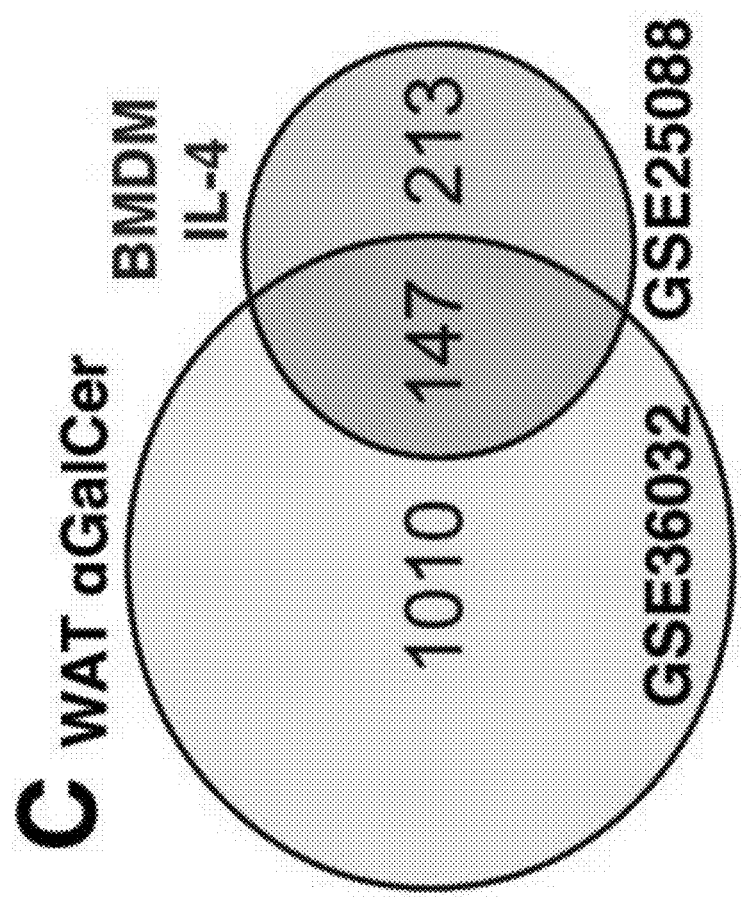

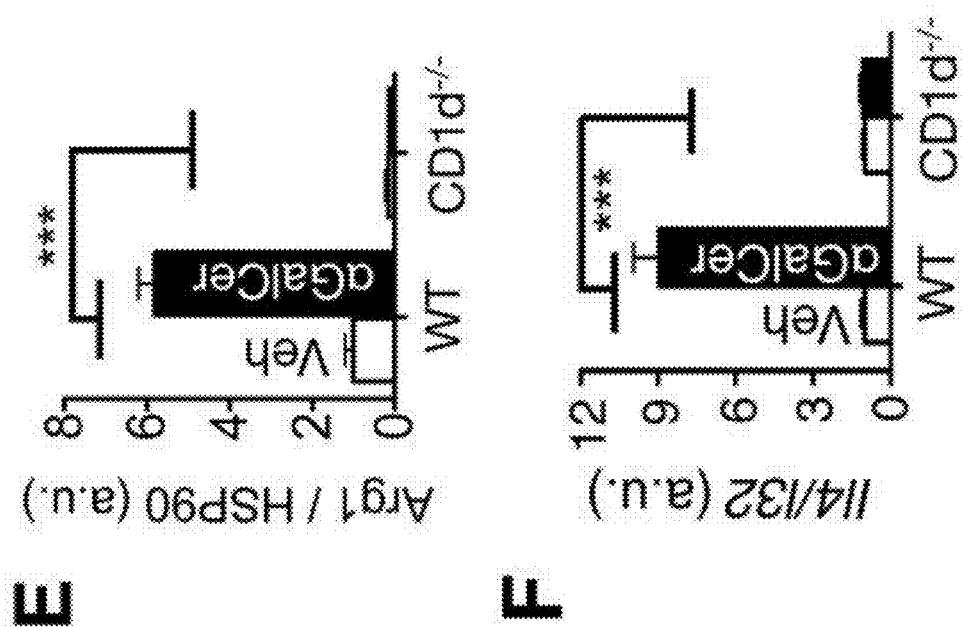
Figs. 9E-F

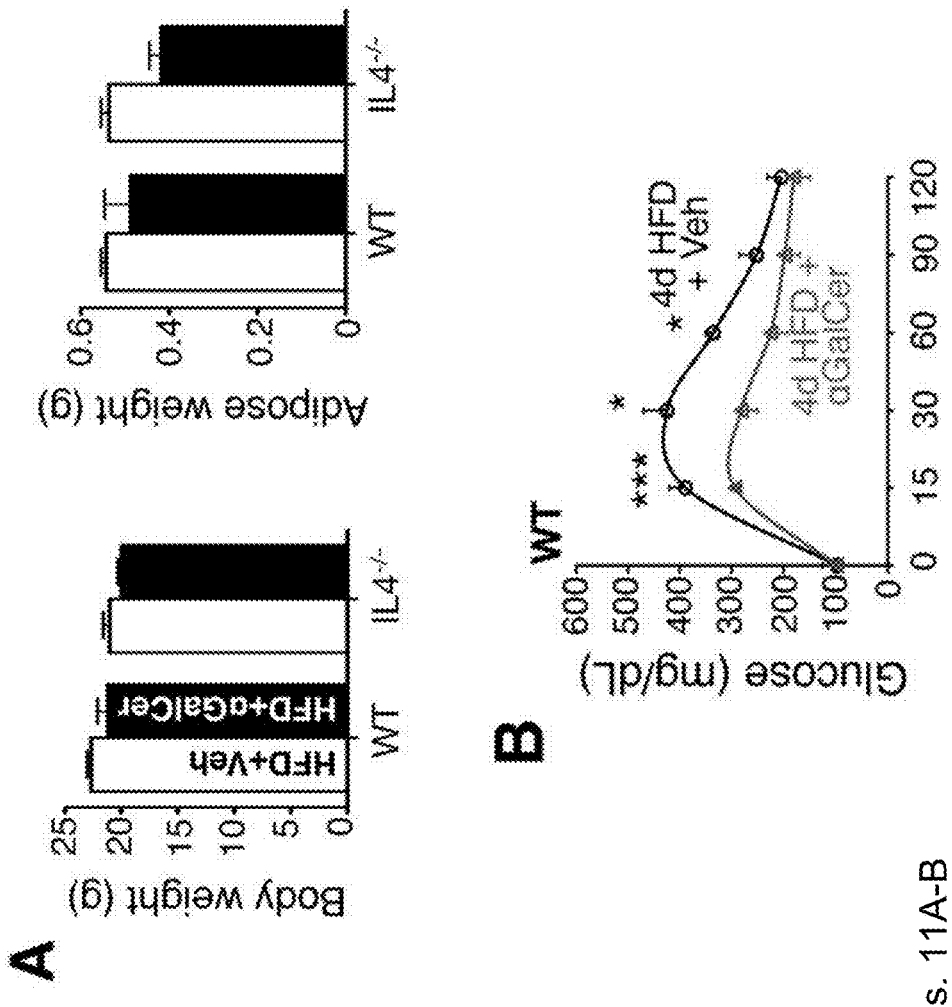
Figs. 11A-B

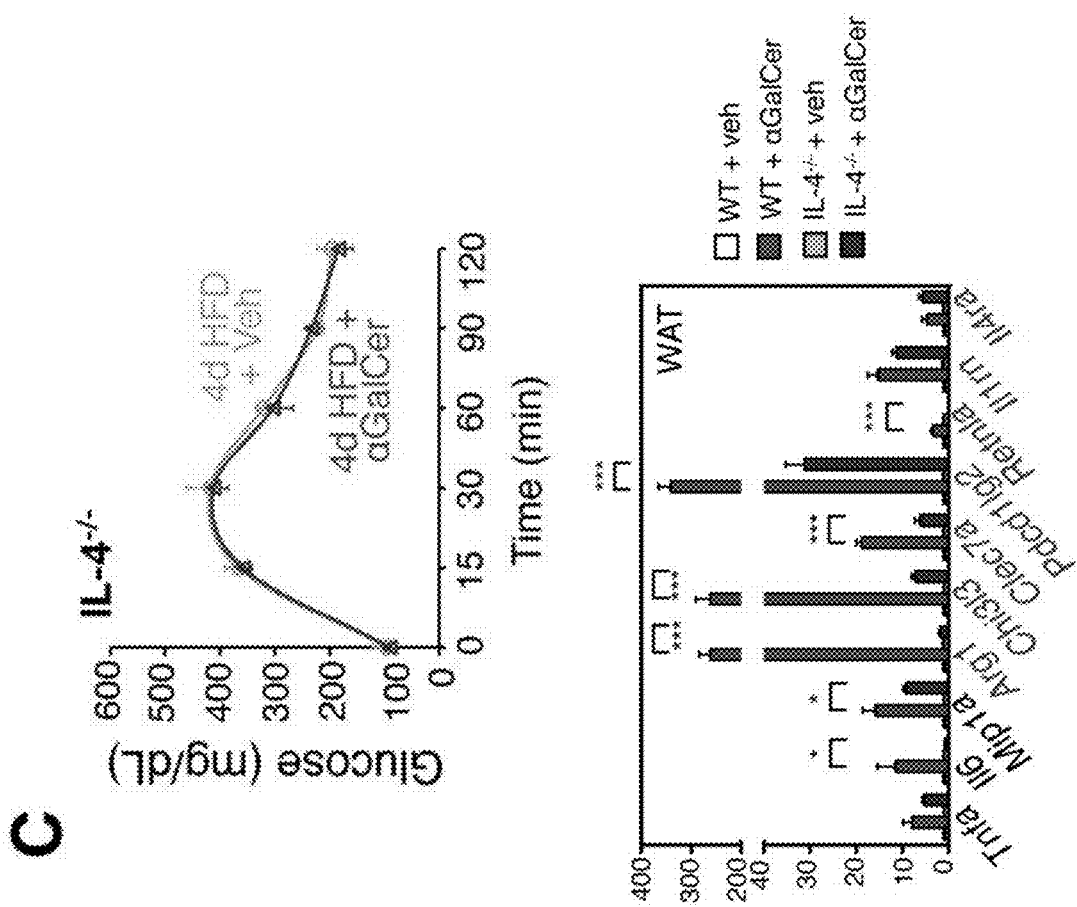
Figs. 11C-D

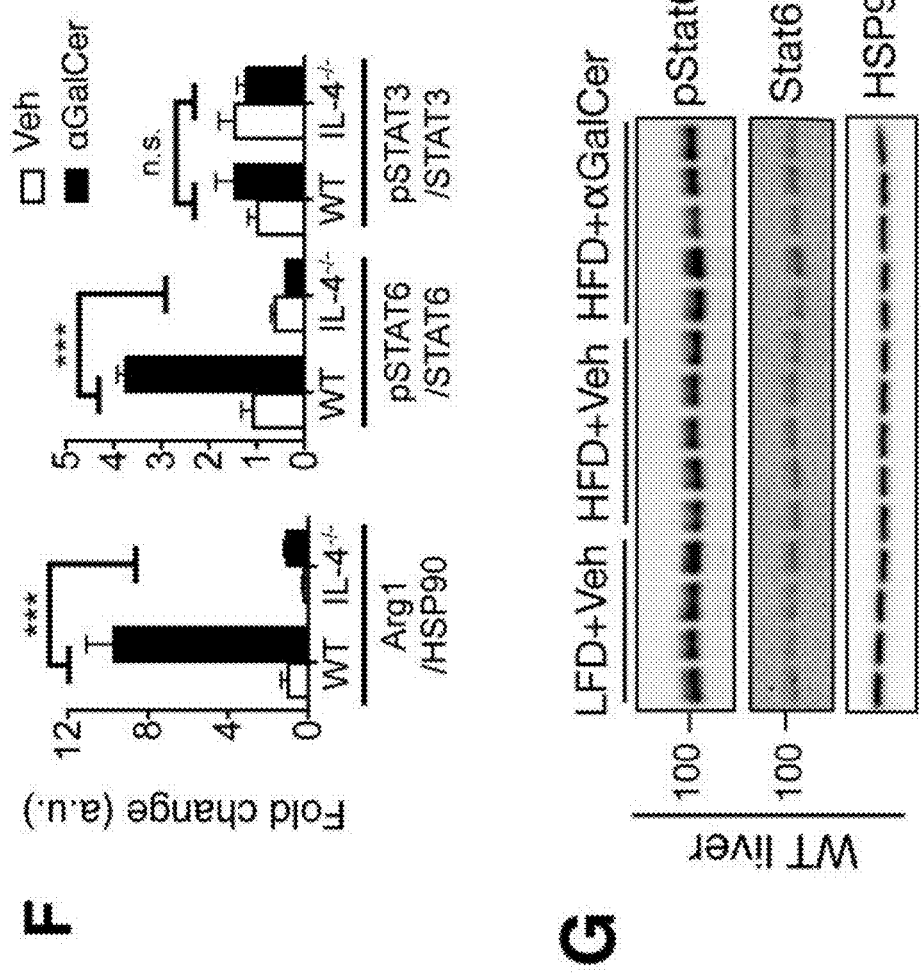
Figs. 11F-G

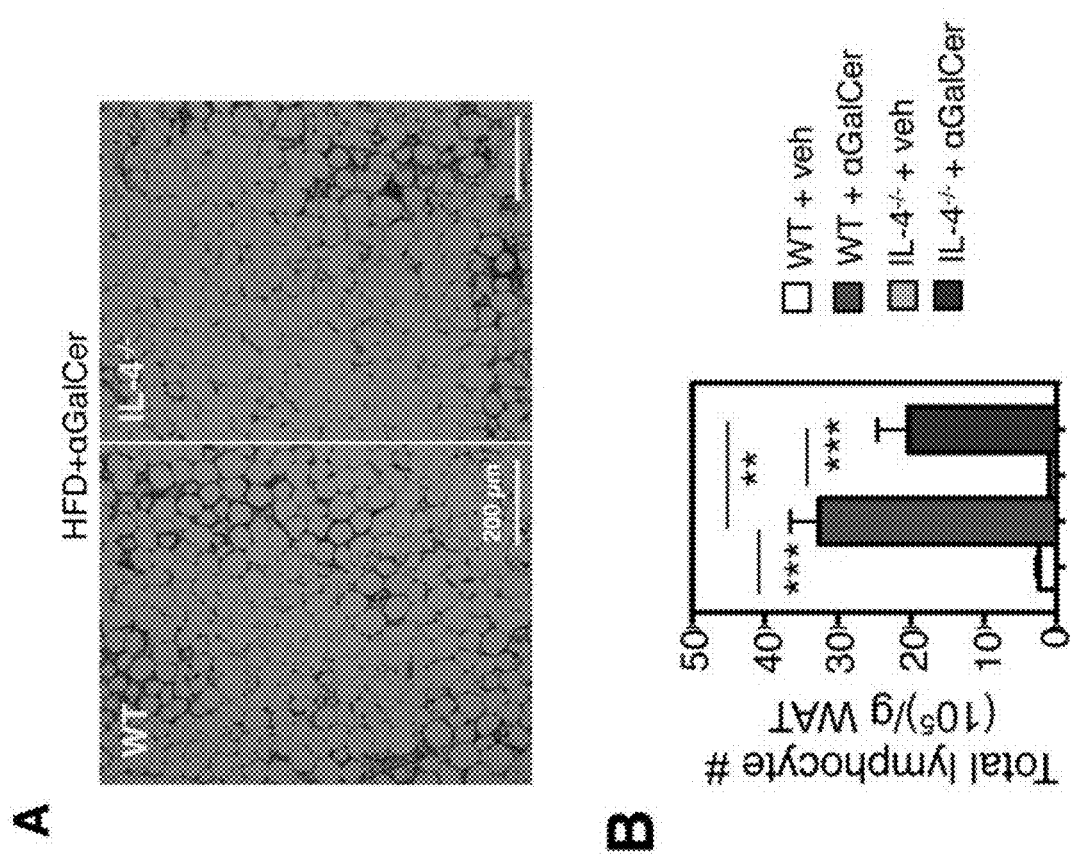
Figs. 12A-B

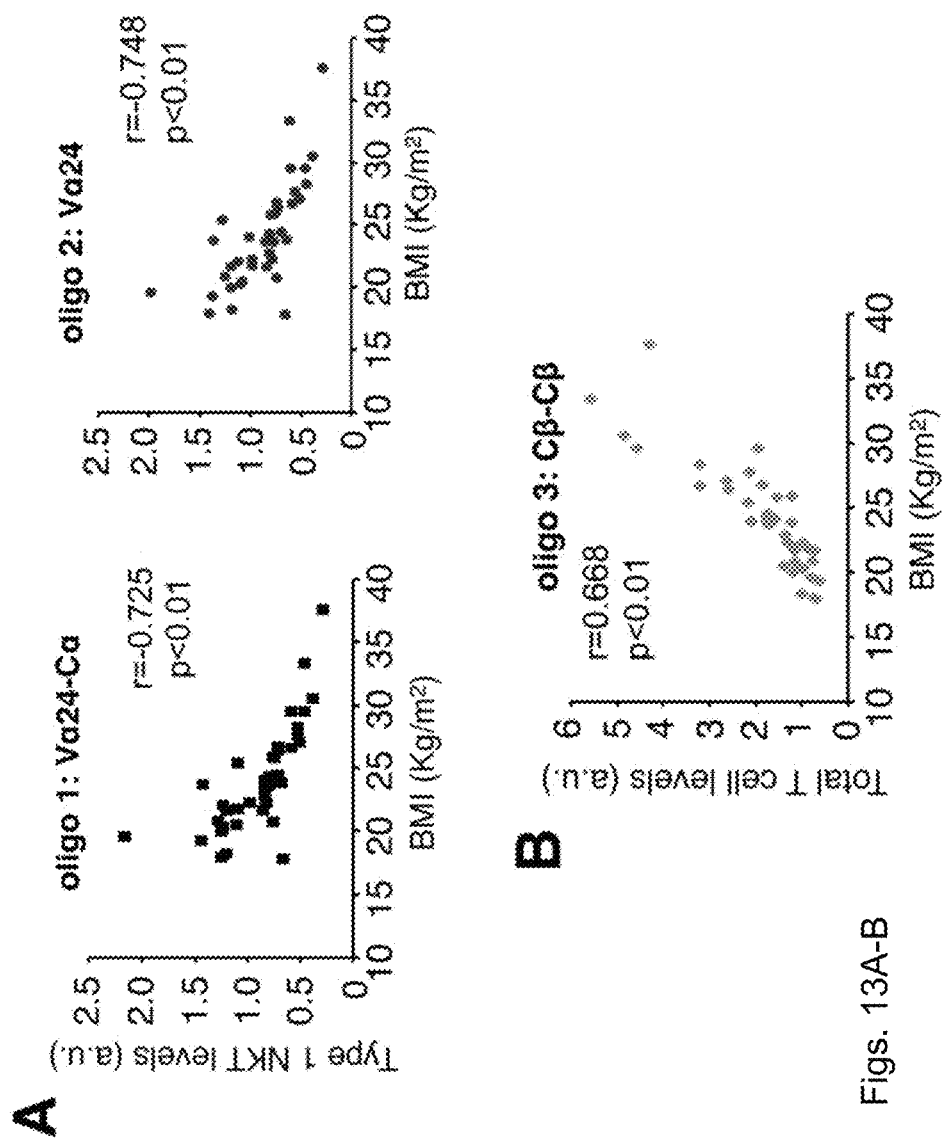
Figs. 13A-B

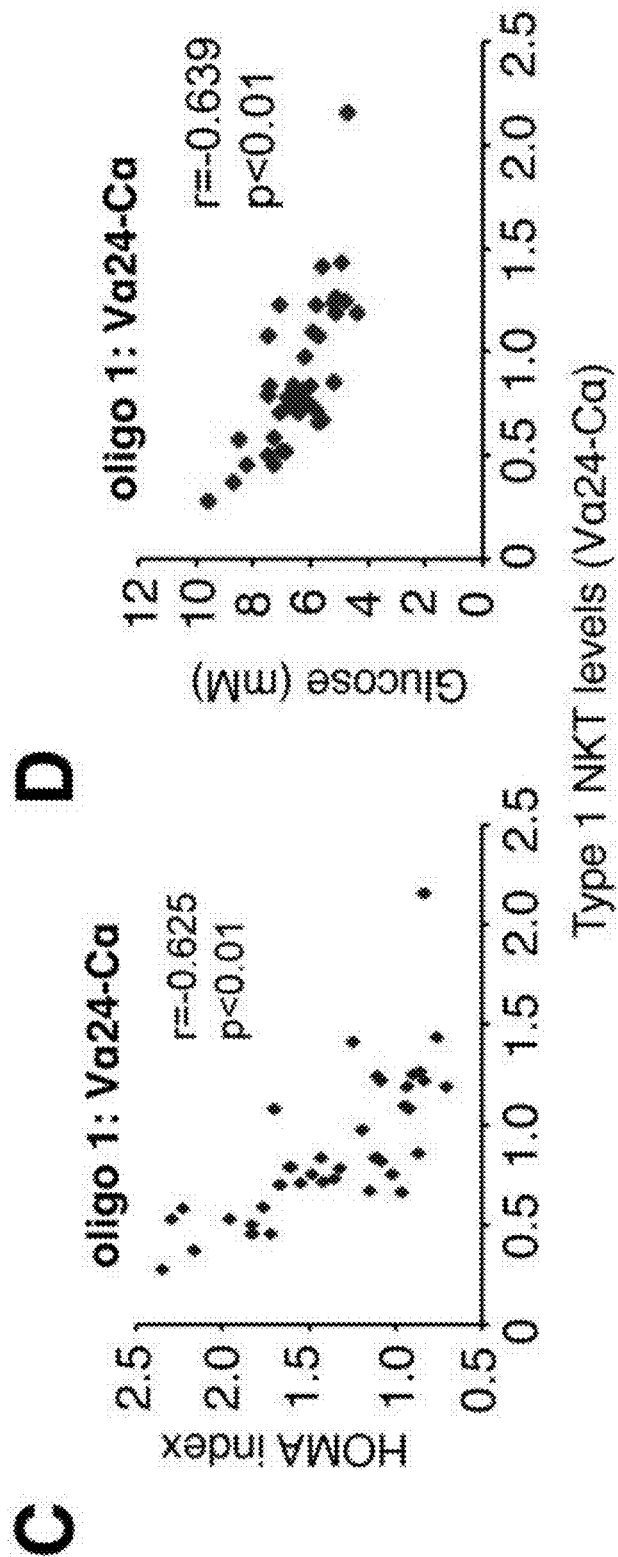
Figs. 13C-D

METHOD TO SCREEN FOR AN ACTIVATOR OF ADIPOSE-RESIDENT NK CELLS

CROSS-REFERENCE TO RELATED APPLICATIONS

This application claims priority from U.S. Provisional Application No. 61/528,995, filed Aug. 30, 2011 and U.S. Provisional Application No. 61/544,455, filed Oct. 7, 2011 which are herein incorporated by reference in their entirety.

GOVERNMENT FUNDING

This invention was made with government support under Grant Nos. R01DK082582 and R01DK082582-Slawarded by the National Institutes of Health NIDKK. The government has certain rights in the invention.

INCORPORATION BY REFERENCE OF SEQUENCE LISTING

The Sequence Listing in an ASCII text file, named as 28002_5594_04_SequenceListing.txt of 7 KB, created on Feb. 24, 2014, and submitted to the United States Patent and Trademark Office via EFS-Web, is incorporated herein by reference.

FIELD OF THE INVENTION

Obesity is associated with a state of chronic low-grade inflammation and the present invention establishes that adipose-resident natural killer T (NKT) cells attenuate inflammation in adipose tissue and improves systemic glucose homeostasis in mice at different stages of obesity. Accordingly, the present invention provides methods of treating type-2 diabetes or those at risk for type-2 diabetes using activators of adipose-resident NKT cells. Such activators include particular glycolipids (e.g., α-galactosylceramide and its analogs other than sulfatide analogs) and cytokines that promote M2 macrophage polarization.

Natural killer T (NKT) cells have been implicated in autoimmunity, microbial infection and cancer and represent an important immunotherapeutic target (Cerundolo et al. (2009) *Nat Rev Immunol* 9, 28-38). Unlike conventional $CD4^+$ and $CD8^+$ T cells, NKT cells recognize and are activated by lipid antigens presented by the MHC class I homologue molecule CD1d on antigen presenting cells such as macrophages and dendritic cells (Bendelac et al. (1995a) *Science* 268, 863-865; Bendelac (1995b) *J Exp Med* 182, 2091-2096; Porcelli et al. (1992) *Nature* 360, 593-597; Beckman et al. (1994) *Nature* 372, 691-694). Among different types of NKT cells, type 1 or invariant NKT cells are the most abundant and best characterized (Godfrey et al. (2010) *Nat Immunol* 11, 197-206). The prototypical lipid antigen is the marine sponge-derived α-galactosylceramide (αGalCer) (Kawano et al. (1997) *Science* 278, 1626-1629), which is not found in mammals, and has been used widely to specifically study type 1 NKT cells in vivo (Bendelac et al. (2007) *Annu Rev Immunol* 25, 297-336). Upon aGalCer activation, NKT cells secrete large amounts of $T_H1$ cytokine, IFN-γ, and $T_H2$ cytokines, IL-4 and IL-13 (Yoshimoto et al. (1995) *Science* 270, 1845-1847). αGalCer challenge has been shown to protect against the development of type-1 diabetes (Miyamoto et al. (2001) *Nature* 413, 531-534; Hong et al. (2001) *Nat Med* 7, 1052-1056) and autoimmune encephalomyelitis, although some of these findings remain controversial (Bendelac et al. (2007)).

The ability of NKT cells to secrete both $T_H1$ and $T_H2$ cytokines upon activation underlies their unique regulatory functions that bridge innate and adaptive immunity (Bendelac et al. (2007); Berzins et al. (2011) *Nat Rev Immunol* 11, 131-142). It is important to note that secretion of $T_H1$ and/or $T_H2$ cytokines by NKT cells is context-dependent (Bendelac et al. (2007); Berzins et al. (2011)) as the nature of the lipid antigens, the subsets of NKT cells, and the microenvironment of the tissues may have significant influences on their cytokine profiles (Miyamoto et al. (2001); Bai et al. (2009) *Proc Natl Acad Sci USA* 106, 10254-10259). Indeed, studies have shown that NKT cells may promote or suppress immune processes by skewing adaptive immune responses towards either a $T_H1$ or $T_H2$ response (Bendelac et al. (2007); Kronenberg (2005) *Annu Rev Immunol* 23, 877-900). However, whether and how NKT cell activation affects obesity-associated inflammation remains to be characterized.

Obesity is associated with a state of chronic low-grade inflammation that significantly contributes to the pathogenesis of this disorder and its associated complications. At late stages of obesity, a variety of immune cells, most notably macrophages (Weisberg et al. (2003) *J. Clin. Invest.* 112, 1796-1808; Xu et al. (2003) *J. Clin. Invest.* 112, 1821-1830), $CD8^+$ T (Rausch et al. (2008) *Int J Obes* (Lond) 32, 451-463; Nishimura et al. (2009) *Nat Med* 15, 914-920), mast cells (Liu et al. (2009 *Nat Med* 15, 940-945), B cells (Winer et al. (2011) *Nat Med* 17, 610-617) and myeloid-derived suppressor cells with immunosuppressive functions (Xia et al. (2011) *J Biol Chem* 289, 23591-23599) infiltrate adipose tissue during diet-induced obesity, with concurrent down-regulation of other immune cells such as regulatory T cells (Treg) (Feuerer et al. (2009) *Nat Med* 15, 930-939). Some of these immune cells may affect the polarization of macrophages to classical (M1) or alternative (M2) activation status via directly or indirectly influencing the local $T_H1$ or $T_H2$ cytokines in the adipose microenvironment (Olefsky et al. (2010) *Annu Rev Physiol* 72, 219-246; Donath et al. (2011) *Nat Rev Immunol* 11, 98-107; Gordon S. et al. (2010) *Immunity* 32, 593-604). Unlike M1, M2 macrophages may contribute to improved insulin sensitivity due to their capacity to resolve inflammation and facilitate wound healing (Gordon et al. (2010); Lumeng et al. (2007) *J. Clin. Invest.* 117, 175-184; Odegaard et al. (2008) *Cell Metab* 7, 496-507; Odegaard et al. (2007 *Nature* 447, 1116-1120). Bias towards M2 polarization can be promoted by immunomodulatory $T_H2$ cytokines such as IL-4 and IL-13. Past studies have identified adipocytes, $CD4^+$ T cells, and eosinophils in adipose tissue as a potential source of $T_H2$ cytokines (Kang et al. (2008) *Cell Metab* 7, 485-495; Wu et al. (2011) *Science* 332, 243-247). Schipper reviews the role of adipose-tissue resident cells in immunometabolism (Schipper et al. (2012) *Trends Endocrinol Metab* 23, 407-415).

Further, a study in 2009 reported the presence of NKT cells in adipose tissue, whose abundance seems decreased with obesity (Lynch et al. (2009) *Eur J Immunol* 39, 1893-1901) and two more recent studies demonstrated the lack of metabolic effect in NKT-deficient $CD1d^{-/-}$ mice following long-term HFD feeding (Kotas et al. (2011) *PLoS ONE* 6, e25478; Mantell et al. (2011) *PLoS ONE* 6, e19831). Despite the seeming negligible role of NKT cells from such loss of function studies, the data reported herein asked whether gain-of-function of NKT cells affects obesity-associated glucose homeostasis and positively demonstrated that aGalCer-mediated activation of NKT cells enhances alternative macrophage polarization in adipose tissue and improves glucose homeostasis in animals at different stages of obesity, providing a new therapeutic target for treating type-2 diabetes, and obesity-associated inflammation.

SUMMARY OF THE INVENTION

Natural killer T (NKT) cells are therapeutic targets in various disease models and under clinical trials for cancer patients. However, their function in obesity and type 2 diabetes heretofore remained unclear. The data gathered in the present invention show that adipose tissues of both mice and humans contain a population of type-1 NKT cells, whose abundance decreases with increased adiposity and insulin resistance. Although loss-of-function of NKT cells had no effect on glucose tolerance in animals with prolonged high-fat diet (HFD) feeding, activation of NKT cells by lipid agonist α-galactosylceramide (αGalCer) enhances alternative macrophage polarization in adipose tissue and improves glucose homeostasis in animals at different stages of obesity. Furthermore, the effect of NKT cells is largely mediated by the IL-4/STATE signaling axis in obese adipose tissue.

According, the present invention is directed to a method for treating an individual having type-2 diabetes or at risk for type-2 diabetes which comprises administering an activator of adipose-resident NKT cells for a time and in an amount to improve glucose tolerance or to decrease insulin resistance in said individual. The activators of the invention include, glycolipids such as α-galactosylceramide and its analogs, with the proviso that said analog is not sulfatide or a sulfatide analog, the cytokines IL-4, IL-10, IL-12 or IL-13 or any other $T_H2$-promoting cytokine or a compound that promotes M2 macrophage polarization.

In some embodiments, the above method can be used to reduce or ameliorate obesity-associated inflammation.

Another aspect of the invention relates to an isolated population of mammalian adipose-resident type-1 NKT cells which has at least 50% to about 80% CD4$^-$CD8$^-$ type-1 NKT cells and about 20 to 30% CD4$^+$CD8$^-$ type-1 NKT cells. These cells exhibit the other markers found on type-1 NKT cells (reactive to aGalCer-loaded CD1d-tetramer, TCRβ$^+$CD44$^{hi}$CD69$^+$CD25$^-$). In some embodiments, the cells are of murine or human origin.

Still a further aspect of the invention provides an in vitro method to screen for an activator of adipose-resident NKT cells by (a) preparing an isolated population of adipose-resident type-1 NKT; (b) contacting said cells with a candidate activator for a time sufficient to induce said cells to release a TH2 cytokine; and (c) detecting whether said cells have produced increased levels of a TH2 cytokine relative to untreated adipose-resident NKT cells. Methods of detecting gene and protein expression on are well known and include, for example, northern blots and other nucleic acid hybridization techniques, RNA-Seq, various PCR techniques, including q-PCR and RT-PCR, ELISAs, immunoblots and immunohistochemical staining.

In some embodiments, the method to screen for an activator of adipose-resident NKT cells comprises (a) preparing an isolated population of adipose-resident type-1 NKT; (b) contacting said cells with a candidate activator for a time sufficient to promote M2 macrophage polarization; and (c) detecting whether said cells have increased expression, relative to untreated adipose-resident NKT cells, of an M2 gene selected from any one or more of the group consisting of Arginase 1 (Arg1), chitinase 3-like 3 (Chi3l3), C-type lectin domain family 7, member a (Clec7a), Programmed cell death 1 ligand 2 (Pdc1Ig2), Resistin like alpha (Retnla), Interleukin 1 receptor antagonist (Il1rn), and Interleukin receptor 4 alpha (Il4ra). The foregoing detection techniques, or any other known in the art, can be used.

Yet another aspect of the invention is drawn to an in vivo method to screen for an activator of adipose-resident NKT cells by (a) administering a candidate activator to one or more mice maintained on a high fat diet (HFD) for at least about 4 days up to about 24 weeks or to one or more control mice; (b) sacrificing said one or more mice from about 4 to about 7 days after administering said activator; (c) preparing white adipose tissue (WAT) from said mice; and (d) detecting whether (i) said WAT contains increased expression, relative to expression in WAT from control mice, of any one or more of IL4, IL13, IL12, Arg1, Chi3l3, Clec71, Pdcd1Ig2, Retnla, IL1m and IL4ra, (ii) M2 macrophage polarization increases in said WAT relative to that in WAT from control mice, and/or (iii) whether one or more $T_H2$ cytokine are produced. The foregoing detection techniques, or any other known in the art, can be used. The mice used in this method can be wild-type mice or have a genetic predisposition to obesity, such as ob/ob mice.

BRIEF DESCRIPTION OF THE DRAWINGS

FIGS. 1A and 1B show the analysis of NKT cells in epididymal adipose tissue of 6 w-old male lean mice on an LFD (white bars) and after a 4 d HFD (black bars). Panels A shows the total number of NKT cells per gram of adipose tissue and Panel B shows the percent of NKT cells in total adipose lymphocytes (n=12 per cohort, with 3 repeats). FIG. 1C provides FACS characterization of cell-surface markers CD4-CD8 of αGalCer-CD1d-tetramer-positive NKT cells from indicated tissues. Numbers in the flow histogram indicate the percent of CD1d-tetramer-positive NKT cells (n=10-12 per cohort, at least 4 repeats). Values represent mean±s.e.m. *, P<0.05.

FIG. 2 illustrates that the abundance of adipose NKT cells decreases with HFD feeding in two obese mouse models. FIG. 2C provides the percentages of NKT and CD8$^+$ T lymphocytes in total lymphocytes in adipose tissue during HFD feeding compared to age-matched LFD cohort (n=12 per cohort, 3 repeats). FIG. 2D provides total cell numbers of various T lymphocytes per g adipose tissue during HFD feeding (n=12, 3 repeats). FIG. 2E provides the body weight of adult 36-40 w-old ob/ob mice relative to wildtype controls. FIGS. 2F and 2G provide the percentages of NKT and CD8$^+$ T cells in adipose tissue and spleen of ob/ob mice compared to age-matched WT lean animals (n=10 per cohort, 2 repeats), respectively. Values represent mean±s.e.m. *, P<0.05, , P<0.01, and *, P<0.005. In panels A-D, white bars are LFD mice; black bars are HFD mice. In panels E-F, white bars are wildtype mice (WT) and black bars are ob/ob mice.

FIG. 3 shows that αGalCer challenge activates NKT cells in adipose tissue. FIG. 3A is a schematic diagram for three gain-of-function models with 4 d-, 8 w-, and 24 w-HFD feeding. 6 w-old mice that have been placed on HFD for 4 d, 8 w and 24 w were injected i.p. with αGalCer or vehicle (veh) on day 0 and day 2. GTT was conducted on day 4 and mice were sacrificed for tissues on day 5. FIG. 3B shows BrdU labeling of CD1d-tetramer-positive NKT cells in adipose tissue following αGalCer challenge. FIGS. 3C and 3F show flow analysis of NKT cells in adipose tissue of mice on 4 d or 8 w HFD, respectively, with the indicated treatments. Number refers to the percentage of NKT cells in total CD45$^+$ lymphocytes in stromal vascular cells (SVC) of adipose tissue. FIGS. 3D and 3E show H&E sections of adipose tissue of WT and CD1d$^{-/-}$ mice after 4 d HFD, respectively, with the indicated treatments.

FIGS. 5A and 5B graphically quantitates the indicated cell numbers per g adipose tissue for total CD45$^+$ lymphocytes, NKT cells, CD8$^+$ T cells, and F4/80$^+$CD11b$^+$ macrophages of mice that have been on LFD, HFD with vehicle or HFD with αGalCer challenge for 4 d or 8 w, respectively (n=4 per cohort).

FIG. 6 shows that NKT cell activation improves systemic glucose homeostasis in murine diet-induced obesity (DIO). FIGS. 6A-6C depicts the results of a GTT of WT mice on LFD (dark line-black), HFD injected with vehicle (light gray line-red) or HFD injected with αGalCer (medium grey line-blue) for different lengths of time. The mice in FIG. 6A were on 4 d HFD (n=12-15 per cohort; 3 repeats); in FIG. 6B the mice were on 8 w HFD (n=9-10 per cohort: 2 repeats); and in FIG. 6C were on 24 w HFD (n=3-4 per HFD cohort and n=10 for LFD). * refer to the P values comparing between HFD+veh and HFD+αGalCer groups. FIG. 6D shows the fasting insulin levels in mice under 8 w HFD (n=9-10 per cohort, 2 repeats). Each bar represents LFD (white), HFD with vehicle (grey) or HFD with αGalCer injection (dark). FIG. 6E depicts the results of a GTT of CD1d$^{-/-}$ mice on LFD (dark line-black), HFD injected with vehicle (light gray line-red) or HFD injected with αGalCer (medium grey line-blue) under 4 d HFD (n=9-10 per cohort, 2 repeats). FIG. 6F depicts the results of a GTT of WT mice on LFD with veh (circles) or αGalCer injection (triangles) (n=10 per cohort, 2 repeats) after about 6 weeks on LFD. Values represent mean±s.e.m. *, P<0.05, and ***, P<0.005.

FIG. 9 establishes that NKT cell activation increases IL-4 signaling in adipose tissue. FIG. 9A depicts a heat map showing the fold-change of gene expression in WAT of WT or CD1d$^{-/-}$ mice on 4 d HFD with or without αGalCer injection (n=3-4 per cohort). Each lane is one individual. A total of 1,556 differentially-expressed genes with q<0.001 and fold-change>2 are shown. FIG. 9B provides the top 10 genes upregulated by αGalCer and their expression changes in IL-4-treated BMDM (GSE25088). n.d., not detected. Scale: 0-1, blue shades; 1-100, red shades. In FIG. 9A, the columns labeled WT_WAT Veh and both CD1d−/−_WAT are mixtures of pale blues and reds. For the remaining column, WT_WAT αGalCer, the intensities range from light to deep shades of red. In the expanded heat map in FIG. 9B, the intensities in the columns labeled WT_WAT Veh and both CD1d−/−_WAT are all white/blue shades. For the BMDM CON column, all boxes are white whereas in the IL-4 column, the boxes are red except for the third gene (light blue) and the tenth gene (dark blue).

FIG. 9C is a Venn diagram showing the overlap of significantly upregulated genes in αGalCer-injected WAT vs. IL-4-treated BMDM datasets. As not all αGalCer-induced genes existed in the IL-4_BMDM dataset, only 1,157 genes, rather than 1,556 genes induced by αGalCer, were included in the Venn diagram. FIG. 9D is a Western blot of Arg1 expression in WAT of WT and CD1d$^{-/-}$ cohorts used in Panel A (n=3-4 per cohort, 2 repeats). Each lane represents an independent sample. FIG. 9E shows the quantitative analysis of the blots in Panel D with the values of the WT+veh sample set at 1. FIG. 9F depicts the Q-PCR analysis of 114 mRNA levels in WAT of WT or CD1d$^{-/-}$ mice on 4 d HFD with or without αGalCer injection (n=4 per cohort). Values represent mean±s.e.m. ***, P<0.005. For panels E and F, the bars represent vehicle injection (white bar) and αGalCer injection (black bar).

FIG. 11 establishes that the NKT cell activation signal acts through the IL-4/STAT6 axis in adipose tissue. 6-7 w-old mice WT or IL-4$^{-/-}$ mice were placed on either LFD or HFD for 4 d with two αGalCer or vehicle injections prior to metabolic phenotyping (n=7-8, 2 repeats). FIG. 11A provides bar graphs showing the weight of body and epididymal adipose tissues on the left and right, respectively. FIGS. 11B and 11C show the results of a GTT in mice injected with vehicle (circles) or αGalCer (triangles) for WT and IL-4$^{-/-}$ mice, respectively. FIG. 11D provides a Q-PCR analysis for the same M1 and M2 genes in FIG. 7 from WAT of WT mice (left two bars for each gene) or of IL-4$^{-/-}$ mice (right two bars for each gene). Within each pair, the left bar is injection with vehicle (veh) and the right bar is injection with αGalCer (n=6 per cohort, 2 repeats). In FIG. 11F, the ratios of Arg1 to HSP90 and p-Y STAT3/6 to total STAT3/6 are quantitated. FIG. 11G shows Western blots for p-Y STAT6 proteins in the liver of the WT mice under LFD, 4 d HFD with vehicle or 4 d HFD with αGalCer injection (n=4-5 per cohort). In FIGS. 11E and 11G, each lane represents an independent sample. Values represent mean±s.e.m. *, P<0.05, , P<0.01, *, P<0.005; n.s., not significant. For FIGS. 11A and 11F, open bars represent 4 d HFD mice injected with vehicle; black bars represent 4 d HFD mice injected with αGalCer.

FIG. 12A shows H&E sections of adipose tissue from WT mice (left) and IL-4$^{-/-}$ mice (right) on a 4 d HFD after αGalCer injection (n=4-5 mice). FIG. 12B graphically depicts the total number of lymphocytes in adipose tissue of WT or IL-4$^{-/-}$ mice on 4 d HFD with or without αGalCer challenge (n=5-6 per cohort, 2 repeats).

FIG. 13 graphically depicts the correlations between adipose NKT cells and various metabolic parameters in humans. NKT cells in visceral adipose tissues of 39 human subjects were analyzed by two oligo sets: Oligos 1-2 measured the Vα24 TCR mRNA levels of type 1 NKT cells. As a control, oligo 3 measured the TCR mRNA levels of total T cells. FIG. 13A shows a scatter plot Vα24 type 1 NKT mRNA levels versus BMI for Oligo 1 (left) and 2 (right). FIG. 13B shows a scatter plot of total T cell mRNA levels versus BMI. FIG. 13C shows a scatter plot of insulin resistance as measured by HOMA versus type 1 NKT mRNA levels measured with Oligo 1. FIG. 13D shows a scatter plot of glucose levels measured at the 2 h point of an oral GTT versus type 1 NKT mRNA levels measured with Oligo 1.

DETAILED DESCRIPTION OF THE INVENTION

1. Definitions and Abbreviations

Figure 1:
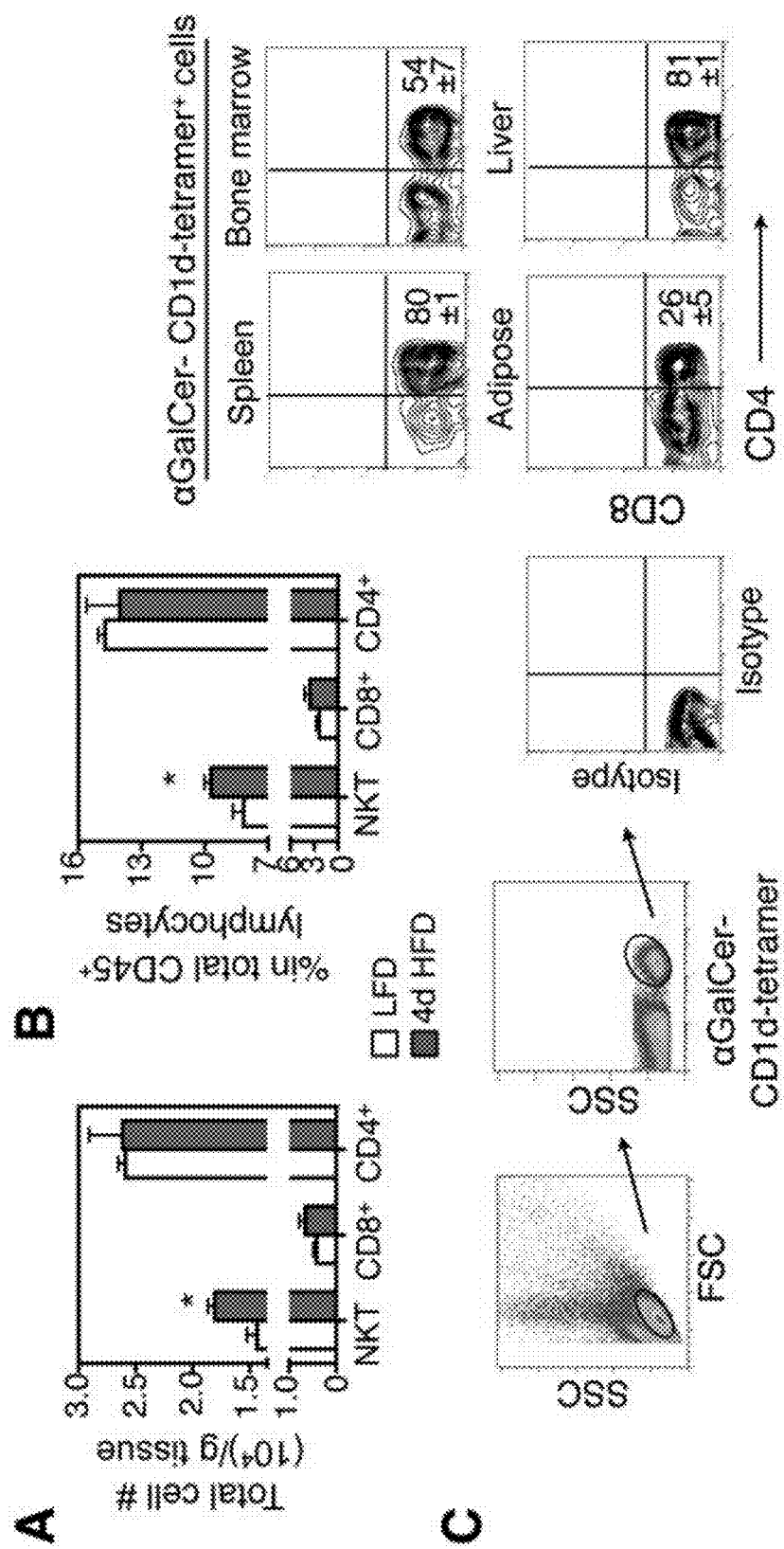
FIG. 1 shows that adipose-resident type I NKT cells increase with 4 d HFD and are predominantly CD4$^-$CD8$^-$.

Type-2 diabetes is a chronic metabolic disease in which individuals have insulin resistance and inadequate insulin regulation, preventing proper glucose utilization. Most individuals with type-2 diabetes are obese, and experience hyperglycemia, usually detectable as abnormal or impaired fasting glucose or abnormal or impaired glucose tolerance before diagnosis.

As used herein "an individual at risk for type-2 diabetes" is an individual who has a set of symptoms and risk factors associated with type-2 diabetes or pre-diabetic conditions leading to type-2 diabetes. Additionally or alternatively, individuals at risk for type-2 diabetes will have a glycated hemoglobin (A1C) level between 5.7-6.4%. Values above that range indicate the presence of diabetes, whereas values below that range are normal. In accordance with well established clinical practice, tests to determine random and fasting glucose levels can also be used to establish whether an individual is at risk for type-2 diabetes.

Whether an individual has type-2 diabetes or is at risk therefor is determined by standard clinical, medical criteria and diagnosis.

Adipose tissue, unless qualified in context, includes both visceral fat and subcutaneous fat. It may be composed of white adipose tissue or brown adipose tissue.

The terms "type-1 NKT" or "invariant NKT" (iNKT) cells are used interchangeably. These cells are distinct cell types from type-II NKT.

As used herein, "an activator of adipose-resident NKT cells" includes but is not limited to cytokines and glycolipids, including αGalCer and its analogs (other than sulfatides or a sulfatide analogs) and other compounds (whether small molecule, oligonucleotides, nucleic acid, peptides, protein or otherwise) that stimulate an increase of type-1 NKT in adipose tissue, especially in murine adipose tissue, or promote M2 macrophage polarization. The αGalCer analogs for use in the invention are those in which the galactosyl moiety can be replace by other monosaccharides, e.g., glucose, gulose and N-acetylglucosamine, those in which the lipid chain of the ceramide can be varied in length, and combinations thereof.

Mammalian includes any mammal, with particular preference for murine, human and primate mammals.

The abbreviations used herein include αGalCer, α-galactosylceramide; ANOVA, analysis of variance; DIO, diet-induced obesity; GSEA, gene-set enrichment analysis; GTT, glucose tolerance test; HFD, high-fat diet; HOMO, homeostasis model assessment; LFD, low-fat diet; NES, normalized enrichment score; NKT, natural killer T cells; OGTT, oral glucose tolerance test; Q-PCR, quantitative PCR; SVC, stromal vascular cells; Veh, vehicle; WAT, white adipose tissue; and WT, wild type.

2. General Overview

The role of NKT cells in regulating obesity-associated inflammation has heretofore been incomplete. With the discovery and characterization of a new subset of type-I NKT cells in adipose tissue and in diet-induced obesity (DOI), this role is being elucidated. In the present invention, adipose-resident type-1 NKT cells from mice WAT have been characterized and shown to be primarily CD4$^-$CD8$^-$ type-1 NKT cells with about 20 to 30% CD4$^+$CD8$^-$ type-1 NKT cells and sulfatide insensitive, which when activated lead to $T_H2$-skewed anti-inflammatory responses and mediate glucose homeostasis. In contrast, spleen and liver type-1 NKT cells are predominantly CD4$^+$CD8$^-$ type-1 NKT cells, with at most a few percentage of CD4$^-$CD8$^-$ type-1 NKT cells, are activated by sulfatide, and when activated lead to $T_H1$-skewed pro-inflammatory response.

Prior studies and data herein with CD1d-/- mice fed an HFD confirmed loss of NKT cells had no metabolic effect and suggested that the NKT cells were dispensable for glucose homeostasis in loss-of function studies. Further, a study using β2-microglobulin (β2m)-deficient mice which lack all MHC class 1 molecules including CD1d concluded that NKT cells infiltrate adipose tissue and that loss of NKT cells reduces inflammation in obesity while activation of NKT cells by one injection of αGalCer had mild effect on glucose tolerance in HFD animals (Ohmura et al. (2010) *Arterioscler Thromb Vasc Biol* 30, 193-199), opposite to the findings in the present invention. However, interpretation of those results is confounded by the fact that the β2m knockout mice not only are deficient in NKT but also CD8+ T cells (Koller et al. (1990) *Science* 248, 1227-1230; Zijlstra et al. (1990) *Nature* 344, 742-746). Accordingly, the absence of CD8+ T cells may account for the reported phenotypes (Nishimura et al. (2009)).

In contrast, the gain-of-function study of the present invention demonstrated that αGalCer-mediated NKT cell activation promotes M2 macrophage polarization in adipose tissue and exerts a salutary effect on systemic glucose homeostasis through the IL-4/STAT6 signaling axis. These gain-of-function data are in line with the known function of NKT cells in altering $T_H1/T_H2$ responses in vivo (Bendelac et al. (2007)). The lack-of-effect of NKT cells at late stages of obesity in the absence of stimulation is not surprising given the massive infiltration and expansion of other cells such as CD8+ T cells and macrophages (Olefsky J. M. et al. (2010) *Annu Rev Physiol* 72, 219-246; Donath M. Y. et al. (2011) *Nat Rev Immunol* 11, 98-107) and given the concomitant reduction of NKT cells.

However, upon activation by a potent stimulus such as αGalCer, NKT cells have significant impact on inflammatory responses in adipose tissue and systemic glucose tolerance in obese animals.

In line with the role of IL-4 in $T_H2$ responses, the data herein suggest the IL-4 is an important mediator of NKT cell function in adipose tissue in the context of obesity and does not exclude a role for other $T_H2$ cytokines such as IL-13, which is known to be secreted by NKT cells (Yoshimoto et al. (1995)) as supported by the observation that loss of IL-4 only partially blocked αGalCer-mediated induction of M2 genes in adipose tissue. While IL-4 and IL-13 share a common signaling pathway through the IL-4 receptor a subunit (IL-4Ra) and may have diverse functions in vivo, since IL13 is involved in TH2 responses, it may have sufficient anti-inflammatory activity for improving glucose tolerance in obesity.

The further observation that, unlike their hepatic counterparts, adipose-resident NKT cells have a $T_H2$-biasing effect upon αGalCer activation is very intriguing. The difference may be related to the nature of antigen presenting cells, tissue microenvironment and/or the different lineage of NKT cells in adipose tissue (Bendelac et al. (2007)). The data herein showed that unlike CD4+CD8− NKT cells in the liver, the majority of NKT cells in adipose tissue are CD4−CD8−, and thus may be associated with specific functional changes. Indeed, earlier studies have shown that CD4−CD8− vs. CD4+CD8− NKT cells likely represent functionally separate lineages that may promote different $T_H$ response with distinct capacities to secrete $T_H1$ and $T_H2$ cytokines (Bendelac et al. (2007); Lee et al. (2002) *J Exp Med* 195, 637-641; Benlagha et al. (2002) *Science* 296, 553-555; Pellicci et al. (2002) *J Exp Med* 195, 835-844). Alternatively, the tissue-specific NKT effect may reflect a unique microenvironment of adipose tissue in terms of antigen presenting cells. Since adipocytes express CD1d transcripts, they may be able to present lipids to and directly activate NKT cells whereas Kupffer cells in the liver have been shown to be important for αGalCer-mediated NKT cell activation (Schmieg et al. (2005) *Proc Natl Acad Sci USA* 102, 1127-1132). Finally, as NKT cell activation by bacterial lipid antigens may be toll-like receptor 4-dependent and IL-12-mediated (Brigl et al. (2003) *Nat Immunol* 4, 1230-1237; Brigl et al. (2011) *J Exp Med* 208, 1163-1177), it will be interesting to investigate whether different cytokine environments of the liver vs. adipose tissue may explain the tissue-specific NKT effect upon αGalCer activation.

The data herein show that αGalCer-mediated NKT activation leads to activation of the IL-4/STAT6 signaling axis in adipose tissue, promoting M2 macrophage polarization. The mechanism of how IL-4 mediates macrophage polarization in adipose tissue remains unclear. It has been shown that STAT6 may modulate the activities of nuclear receptors (PPARγ or PPARβ/δ) (Chawla (2010) *Circ Res* 106, 1559-1569) or induce the expression of histone H3K27 demethylase Jmjd3 (encoded by Kdm6b gene) (Ishii et al. (2009) *Blood* 114, 3244-3254; Satoh et al. (2010) *Nat Immunol* 11, 936-944) to influence M2 macrophage polarization. The data show that M2 marker genes induced by αGalCer are not affected by lack of either PPARγ or PPARβ/δ in myeloid cells, consistent with two recent studies demonstrating that PPARγ and PPARβ/δ in macrophages or myeloid cells are dispensable for the $T_H2$ responses (Szanto et al. (2010) *Immunity* 33, 699-712; Marathe et al. (2009) *J Lipid Res* 50, 214-224). The discrepancies may be due to different genetic backgrounds of mice, fatty acids composition of diets, or gut microbiota.

In line with the animal data, the abundance of type 1 NKT cells in adipose tissue decreases in obese humans. Although this was initially reported by an earlier study (Lynch et al. (2009)), the present data, using a much larger cohort, further demonstrate that abundance of type 1 NKT cells in adipose tissue negatively correlates with BMI, insulin resistance and OGTT glucose levels. The near-perfect correlations between adipose NKT and metabolic parameters suggest that these cells may be involved in the regulation of insulin sensitivity in obese humans. Since αGalCer is not toxic, is well tolerated in humans and often stimulates the expansion of residual NKT cell populations in other disease settings (Berzins et al. (2011); Giaccone et al. (2002) *Clin Cancer Res* 8, 3702-3709), one embodiment of the present invention provides a method wherein NKT-activating glycolipids are used in treating type 2 diabetes. Similar methods using NKT lipid agonists can skew $T_H2$ bias in adipose tissue and hence delay or ameliorate the development of inflammation and type 2 diabetes in obese patients.

3. Methods of Treatment

The present invention provides a method for treating an individual having type-2 diabetes or at risk for type-2 diabetes by administering an activator of adipose-resident NKT cells for a time and in an amount to improve glucose tolerance or to decrease insulin resistance in said individual. Such activators can also be used to treat, e.g., reduce or ameliorate, obesity-associate inflammation.

Activators of adipose-resident NKT cells include glycolipids, ceramides and cytokines which promote M2 macrophage polarization or cause TH2-biased immune responses that are anti-inflammatory. Particular glycolipids include, but are not limited to α-galactosylceramide (chemical name, (2S,3S,4R)-1-O-(alpha-D-galactosyl)-N-hexacosanoyl-2-amino-1,3,4-octadecanetriol) and its analogs (provided the analogs do not include sulfatide or are sulphated) such as those with galactosyl moiety replaced by another monosaccharides, e.g., glucose, gulose and N-acetylglucosamine or by different length lipid chains in the ceramide moiety. OCH, a synthetic sphingosine truncated derivative of αGalCer (OCH chemical name, tetracosanoic acid 1-galactopyranosyloxy-3,4-dihydroxydec-2-yl amide), is not effective in vivo.

Cytokines which can act as activators of adipose-resident NKT cells include, but are not limited to, IL-4, IL-10, IL-12 and IL-13. Any other NKT lipid agonist can be useful to activate adipose-resident NKT cells and can be identified using the screening methods described herein.

As used herein, "treatment" refers to clinical intervention in an attempt to alter the disease course of the individual or cell being treated, and can be performed either for prophylaxis or during the course of clinical disease.

As used herein, the terms "therapeutically-effective amount" and "effective amount" are used interchangeably to refer to an amount of a composition of the invention that is sufficient to result in improved glucose tolerance or decreased resistance to insulin. Glucose tolerance and insulin resistance can be assessed by standard assays known in art. Improvements in obesity associated inflammation can be assessed by reduction in one or more measures of inflammation or changes in inflammatory markers that indicate anti-inflammatory effects.

A therapeutically-effective amount can be administered to a patient in one or more doses sufficient to affect glucose tolerance or reduce insulin resistance and thereby reduce the pathological consequences of the type-2 diabetes, or reduce the symptoms thereof. The amelioration or reduction need not be permanent, but may be for a period of time ranging from at least one hour, at least one day, or at least one week or more. The effective amount is generally determined by the physician on a case-by-case basis and is within the skill of one in the art. Several factors are typically taken into account when determining an appropriate dosage to achieve an effective amount. These factors include age, sex and weight of the patient, the severity of the condition, as well as the route of administration, dosage form and regimen and the desired result.

The activators of the invention can be delivered by any convenient route, including oral, parenteral, s.c., i.p, i.v. routes as well as part of a dietary or feeding regimens.

The optimal dosage, delivery and/or feeding routes and frequency of αGalCer, cytokines, and other $T_H2$-biasing lipid agonists in humans can be readily determined by the skilled artisan using routine methods.

For example, the daily dosage of the activators can be varied over a wide range from 0.01 to 1,000 mg per adult per day, depending on whether the activator is a glycolipid or cytokine. In general, the compositions contain 0.01, 0.05, 0.1, 0.5, 1.0, 2.5, 5.0, 10.0, 15.0, 25.0, 50.0, 100, 250 and 500 mg of the active ingredient. A medicament in unit dosage form typically contains from about 0.01 mg to about 500 mg of the active ingredient, and preferably from 0.05 mg to about 10 mg when the active ingredient is a glycolipid and from 1 mg to about 100 mg when the active ingredient is a cytokine An effective amount of the drug is ordinarily supplied at a dosage level from 0.0002 mg/kg to about 20 mg/kg of body weight per day, especially from about 0.001 mg/kg to 0.10 mg/kg of body weight per day. For a glycolipid, the preferred dosage level range from 0.001 mg/kg to about 1 mg/kg of body weight per day and include a range from 0.001 mg/kg to about 0.01 mg/kg of body weight per day. It will be understood, however, that the specific dose level and frequency of dosage for any particular patient may be varied and will depend upon a variety of factors including the activity of the specific compound employed, the metabolic stability, and length of action of that compound, the age, the body weight, general health, sex, diet, mode and time of administration, rate of excretion, drug combination, the severity of the particular condition, and the host undergoing therapy.

The activators of the invention can be provided, for example, as pharmaceutical compositions for oral, sublingual, subcutaneous, intramuscular, intravenous, transdermal, inhalation, local or rectal administration, with the active principle, alone or in combination with another active principle. Such compositions can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Capsules are one preferred embodiment. Compositions for prolonged release (e.g., including sustained or delayed release) can also be administered.

The activators of the invention can be provided, especially a glycolipid for example, in a consumer food product, including as beverages and powders or liquids and the like for mixing into a consumer food product or beverage.

4. Screening Methods

The present invention provides in vitro and in vivo methods for screening candidate compounds capable for activating adipose-tissue resident NKT cells or for other medical benefits associated with improving glucose tolerance, reducing insulin resistance and/or reducing obesity-associated inflammation.

The in vitro methods take advantage of the fact that adipose-resident NKT cells release greater anti-inflammatory mediators into the medium when stimulated with glycolipids, and particularly with αGalCer stimulation. Hence, one such method, a compound is screened for NKT activating activity by preparing an isolated population of adipose-resident type-1 NKT and contacting those cells with a candidate activator for a time and in an amount sufficient to induce increased release of a $T_H2$ cytokine relative to untreated adipose-resident NKT cells. Alternately, or in addition, one can monitor for the ability of the candidate activator to promote M2 macrophage polarization relative to controls. Such polarization can be detected, for example, by whether the cells have increased expression, relative to untreated adipose-resident NKT cells, of an M2 gene selected from any one or more of the group consisting of Arginase 1 (Arg1), chitinase 3-like 3 (Chi3l3), C-type lectin domain family 7, member a (Clec7a), Programmed cell death 1 ligand 2 (Pdc1Ig2), Resistin like alpha (Retnla), Interleukin 1 receptor antagonist (IL1rn), and Interleukin receptor 4 alpha (IL4ra).

To detect in increased gene and protein expression of a $T_H2$ cytokine or an M2 gene, a myriad of techniques are available in the art, including but not limited to northern blots and other nucleic acid hybridization techniques, RNA-Seq, various PCR techniques, including q-PCR and RT-PCR, ELISAs, immunoblots and immunohistochemical staining.

The amounts and times for contacting cells with a potential activator can be readily determined by the skilled artisans and examples thereof are provided in the Example section. For detection, medium or cells can be harvested for analysis.

This invention further provides methods of screening candidate compounds using a mouse model of obesity. In one embodiment, a method is provided for screening candidate compounds for ability to increase adipose-resident NKT cells, to improve glucose utilization and to skew gene expression to promote M2 macrophage polarization in adipose tissue. Mouse models of obesity include wildtype mice fed HFD diets for from about 4 days to about 24 weeks as well as genetic obesity models such as an ob/ob mouse. The candidate compounds can be fed to the mice or can be delivered by any convenient route, including i.p. (intraperitoneal), s.c. (subcutaneous), oral and the like. Any adipose tissue can be isolated for analysis to detect whether the compound has activated adipose-resident NKT cells. WAT is preferred.

Hence, one method to screen for an activator of adipose-resident NKT cells comprises administering a candidate activator to one or more mice a high fat diet (HFD) for at least about 4 days up to about 24 weeks or to one or more genetically obese mice. After a period of time, the mice are sacrificed for analysis of WAT. Prior to sacrifice, the mice can be subjected to GTT for assessing NKT activation by glucose tolerance relative to appropriate controls. Once WAT is obtained, one detects whether the WAT contains increased expression, relative to expression in WAT from control mice, of any one or more of IL4, IL13, IL12, Arg1, Chi3l3, Clec71, Pdcd1lg2, Retnla, Il1m and Il4ra. Alternatively or in addition, one can analyze the WAT to detect whether M2 macrophage polarization increases in treated WAT relative to untreated control WAT and/or whether one or more $T_H2$ cytokine are produced. Methods for detecting such gene and protein expression are known in the art and have been described above.

The candidate activators for use in the present in vitro and in vivo screening methods can be any type of compound including small molecules, lipids, proteins, peptides, antibodies, siRNA and more and obtained in any manner. The activators can be tested singly (especially in the in vivo methods) or in combinatorial libraries, especially in the in vitro methods adapted for high through put screening. Combinatorial libraries include biological libraries; peptoid libraries (libraries of molecules having the functionalities of peptides, but with a novel, non-peptide backbone, which are resistant to enzymatic degradation but which nevertheless remain bioactive); spatially addressable parallel solid phase or solution phase libraries; synthetic library methods requiring deconvolution; the 'one-bead one-compound' library method; and synthetic libraries using affinity chromatography selection.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. All references patents, patent applications or other documents cited are herein incorporated by reference in their entirety.

Example 1

General Materials and Methods

Mouse Models.

WT C57/B6 (The Jackson Laboratory #000664), B6.V-Lep$^{ob}$/J (ob/ob, #000632), B6.129S6-Cd1d1/Cd1d2$^{tm1spb}$/J (CD1d$^{-/-}$, #008881), and B6.129P2-IL4$^{tm1Cgn}$/J, #002253) were purchased from the Jackson Laboratory and bred in our facility. The latter three have been backcrossed in the Jackson Laboratory to the B6 background over 45, 13, and 12 times, respectively. Myeloid cell-specific PPARγ$^{-/-}$ or PPARδ$^{-/-}$ mice were generated by crossing Pparg$^{flox/flox}$ or Ppard$^{flox/flox}$ mice to the B6.129P2-Lyz2$^{tm1(cre)Ifo}$/J mice (The Jackson Laboratory #004781) (Kang K. et al. (2008) Cell Metab 7, 485-495) and have been backcrossed to the C57BL/6 background for over 10 times. Mice were housed in microisolators in our brand-new pathogen-free facility with sterile 13% LFD with 13% fat, 67% carbohydrate and 20% protein from Harlan Teklad (#2914) or 60% HFD with 59% fat, 26% carbohydrate and 15% protein from Bio-Serv Inc. (F3282). The composition of each is shown in Table 1.

Antibodies and Reagents for Flow Cytometry.

Fluorochrome- or biotin-conjugated antibodies against CD3 (145-2C11), TCRβ (H57-597), CD4 (GK1.5), CD8 (YTS169), F4/80 (BM8), CD11b (M1/70), CD45 (30-F11), BrdU-FITC (PRB-1), avidin-PerCP and isotype control antibodies were purchased from BioLegend, UCSF Flow Core Facility or BD Biosciences. αGalCer-loaded CD1d-tetramer-PE was generously provided by the NIH Tetramer Facility. Data were analyzed using the CellQuest software (BD Biosciences) and Flowjo (Flowjo.com).

Quantitation of Immune Cells in Adipose Tissue Using Flow Cytometric Analysis.

Single-cell suspensions of stromal vascular cells (SVC) from adipose tissue were prepared as described (Xia et al. (2011)). SVCs from two fat pads per mouse were diluted in 120-200 µl PBS, from which one tenth was used for the subsequent staining Following incubation with anti-CD16/CD32 antibody to block Fc receptors, $1\times10^6$ cells were incubated with 20 µl of antibodies diluted at optimal concentrations for 20 min at 4° C. Cells were washed three times with PBS and then resuspended in 200 µl PBS for analysis using the FACSCalibur Flow Cytometer (BD Biosciences). NKT cells were defined as CD45$^+$αGalCer-loaded CD1d-tetramer$^+$CD3/TCRβ$^+$ lymphocytes; CD8$^+$ T cells were defined as CD8$^+$CD45$^+$ cells; macrophages were as CD45$^+$F4/80$^+$CD11b$^+$ cells. During the run, samples were completely run out and the total number of CD45$^+$ lymphocytes or immune cells were gated and counted. The total cell number for various immune cells per g adipose tissue was calculated as (% cells in total CD45$^+$ lymphocytes or immune cells×total CD45$^+$ lymphocytes or immune cells)/g adipose tissue.

Intracellular Flow Cytometric Analysis.

For the Brdu staining, mice were injected (i.p.) with αGalCer (100 ng per g body weight) at day 0, and then with BrdU (Sigma, 0.6 mg/10 g body weight) at 36 h and 12 h prior to sacrifice at day 3. SVC of adipose tissues were purified, labeled with cell surface antibodies and then fixed in cold 70% ethanol at −20° C. overnight. The rest of steps were performed as the regular flow cytometric analysis using BrdU-FITC antibody and DNA dye 7-AAD (Anaspec).

RNA Extraction and Quantitative (Q)-PCR.

RNA extraction from cells and murine tissues, and Q-PCR were carried out as previously described (36) using Trizol (Invitrogen) for liver, and Trizol plus QIAeasy kit (Qiagen) for adipose tissues with DNase digestion (Roche). Q-PCR data collected on the Roche LightCycler 480 were normalized to ribosomal l32 gene in the corresponding sample. Primer sequences are listed in Table 2.

H&E Histology.

Adipose tissues were fixed in 4% formaldehyde, embedded in paraffin and sectioned by the Cornell Histology Core Facility. Pictures were taken using the Axiovert 200M microscope (Zeiss).

Western Blot.

Tissues or cells were lysed in Tris-based lysis buffer containing 1% Triton X-100. Normally, 15-30 μg of total lysates unless otherwise indicated were used in a mini SDS-PAGE as described (Sha et al. (2009) *Cell Metab* 9, 556-564). Antibodies specific for (p-Tyr641) STAT6 and (p-Tyr705) STAT3 (Cell signaling) and Arginase 1 (N-20, Santa Cruz sc-18351) were used at 1:500-2000 and for the loading control HSP90 (Santa Cruz) was used at 1:6000. The secondary antibody goat anti-rabbit IgG HRP (1:10,000) was from Bio-Rad. Quantitation of band density was carried out using the ImageLab software of the Bio-Rad ChemiDoc XRS+system following exposure.

ELISA.

Blood was collected in animals upon 6 h fasting during the day. Circulating insulin levels were measured using the kit from Millipore per supplier's protocols.

Statistical Analysis.

Results are expressed as mean±s.e.m. Comparisons between groups were made using either unpaired two-tailed Student t-test of the EXCEL software for two-group comparisons or the one- or two-way ANOVA test with the Bonferroni Post-tests of the PRISM software for multi-group comparisons. For human studies, statistical analysis was performed with the SPSS 11.5 statistical software package. $P<0.05$ was considered as statistically significant.

TABLE 1

Composition of LFD and HFD

| Dietary fatty acid composition (mg/g diet) | 13% LFD (Teklad 2914) | 60% HFD (Bio-Serv, F3282) |
|---|---|---|
| Myristic (C14:0) | — | 5 |
| Palmitic (C16:0) | 5 | 85 |
| Palmitoleic (C16:1n7) | — | 10 |
| Stearic (C18:0) | 1 | 48 |
| Oleic (C18:1n9) | 7 | 148 |
| Linoleic (C18:2n6) | 20 | 37 |
| Linolenic (C18:3n3) | 1 | 4 |
| Calorie of fat | 13% | 59% |
| Calorie of protein | 20% | 15% |
| Calorie of CHO | 67% | 26% |

TABLE 2

Q- and RT-PCR primers

| Target genes | Sequence F | Sequence R | SEQ ID NO. For F, R |
|---|---|---|---|
| Inflammatory gene analysis (mouse) | | | |
| TNF-α (Tnfa) | TCAGCCGATTTGCTATCTCATA | AGTACTTGGGCAGATTGACCTC | 1, 2 |
| Interleukin 4 (Il4) | CATGGGAAAACTCCATGCTT | TGGACTCATTCATGGTGCAG | 3, 4 |
| Interleukin 6 (Il6) | AGACAAAGCCAGAGTCCTTCAG | TGCCGAGTAGATCTCAAAGTGA | 5, 6 |
| MIP-1α (Mip1a) | TTCTCTGTACCATGACACTCTGC | CGTGGAATCTTCCGGCTGTAG | 7, 8 |
| Arginase 1 (Arg1) | CTCCAAGCCAAAGTCCTTAGAG | AGGAGCTGTCATTAGGGACATC | 9, 10 |
| chitinase 3-like 3 (Chi3l3) | GGCTCAAGGACAACAATTTAGG | ACTGTGGAAAAACCGTTGAACT | 11, 12 |
| C-type lectin domain family 7, member a (Clec7a) | TCATTGAAAGCCAAACATCG | CCTGGGGAGCTGTATTTCTG | 13, 14 |
| Programmed cell death 1 ligand 2 (Pdcl1g2) | ACGTGGCCACTTCATGTTTT | TCTTGAGGGTTTCCCATCAG | 15, 16 |
| Resistin like alpha (Retnla) | TATGAACAGATGGGCCTCCT | AGCTGGGTTCTCCACCTCTT | 17, 18 |
| Interleukin 1 receptor antagonist (Il1rn) | TTGTGCCAAGTCTGGAGATG | TTCTCAGAGCGGATGAAGGT | 19, 20 |
| Interleukin receptor 4 alpha (Il4ra) | GAAGCCAGGAGTCAACCAAG | ATACAGCGCACCACACTGAC | 21, 22 |
| NKT TCR analysis (Human) | | | |
| Oligo 1: TRAV10 (T cell receptor alpha variable 10 or Vα24)-TRAC (TCR constant) | GATATACAGCAACTCTGGATGCA | GGCAGACAGACTTGTCACTGGAT | 23, 24 |
| Oligo 2: TRAV10 (T cell receptor alpha variable 10 or Vα24) | AAGCATCTGACGACCTTCTTG | AACAGGACCTCTCCCAGTATC | 25, 26 |

TABLE 2-continued

Q- and RT-PCR primers

| Target genes | Sequence F | Sequence R | SEQ ID NO. For F, R |
|---|---|---|---|
| Oligo 3: TRBC2 (T cell receptor beta constant 2) | CAGCGAGCCCTACTCAAATTAG | CAGCGAGCCCTACTCAAATTAG | 27, 28 |
| 18S | AGTCCCTGCCCTTTGTACACA | CGATCCGAGGGCCTCACTA | 29, 30 |

Example 2

Characterization of NKT Cells in Mouse Adipose Tissue

CD1d-restricted NKT cells can be classified into two main types with the majority being αGalCer-reactive invariant type I and the rest being variant t e II NKT cells.

Flow cytometric analysis provided an estimate of approximately 15,000 type I NKT cells per gram epididymal adipose tissue in a 6 w-old lean mouse, about half of CD4$^+$ T cells but 4 times higher than CD8$^+$ T cells (white bars in FIG. 1A). Further analyses of type I NKT cells in adipose tissue revealed that the proportion and the absolute numbers of type I NKT cells in adipose tissue were increased by approximately 20% and 25%, respectively, with 4 d HFD challenge (white vs. black bars of NKT cells in FIG. 1A-B). This was not seen in other adipose-resident T cells such as CD4$^+$, CD8$^+$ T cells (FIG. 1A-B). Additionally, adipose-resident type I NKT cells were primarily CD4$^-$CD8$^-$ with one quarter being CD4$^+$CD8$^-$ (FIG. 1C). In contrast, type I NKT cells in liver and spleen consisted primarily of CD4$^+$CD8$^-$ with a small fraction of double negative CD4$^-$CD8$^-$, and in bone marrow the ratio of CD4$^+$CD8$^-$ to CD4$^-$CD8$^-$ type 1 NKT cells was about 1:1 (FIG. 1C). Examination of other activation markers CD44, CD69 and CD25 revealed no differences among type I NKT cells in various tissues as they all were CD44$^{hi}$CD69$^+$CD25$^-$. Taken together, these data suggest that adipose tissues of lean and 4 d HFD mice contain CD4$^-$CD8$^-$ type I NKT cells.

Example 3

Abundance of Adipose-Resident Type 1 NKT in Obese Mice

Figure 2A:
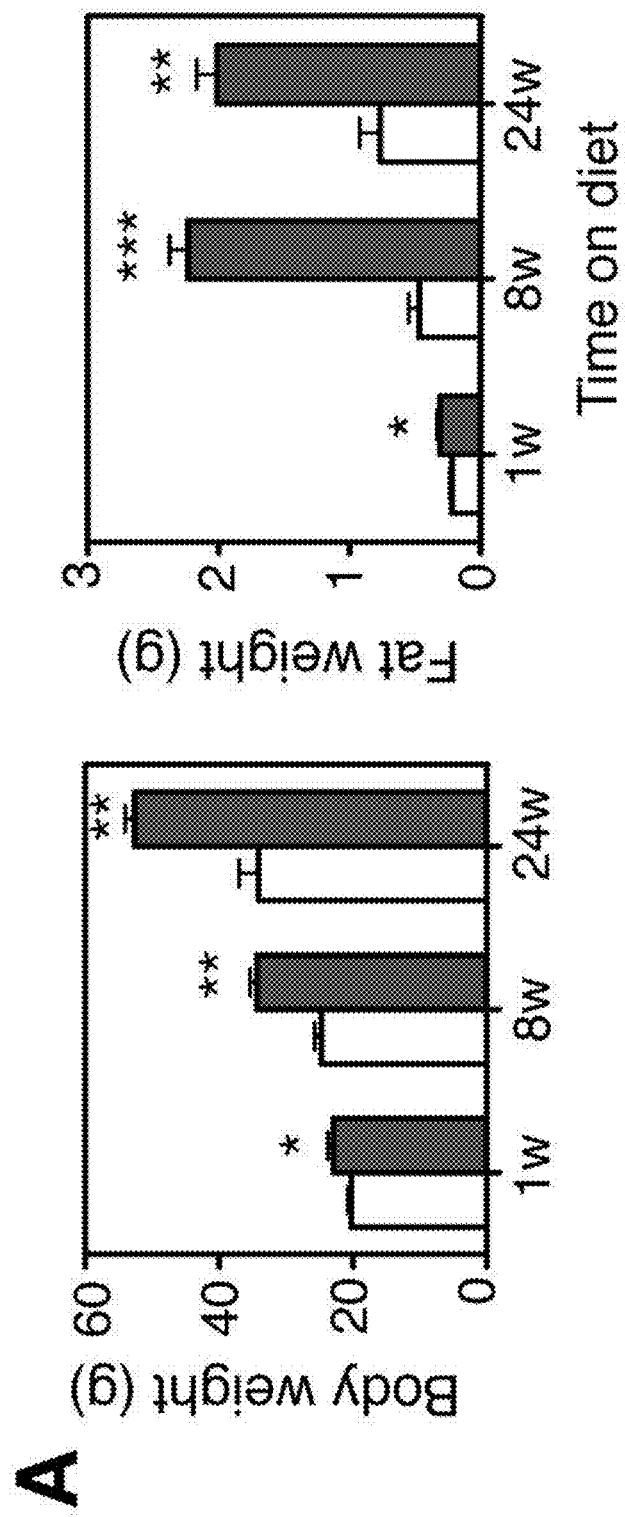
FIGS. 2A an 2B show the body and epididymal fat weights, and fasting glucose levels, respectively, of wildtype C57BL/6 male mice fed an HFD for 1 w to 24 w, compared to age-matched male mice on an LFD (n=12-15 per cohort).

To study the impact of obesity on NKT cells in adipose tissue (adipose-resident NKT cells), 6 w-old B6 mice were placed on a HFD containing 60% calories derived from fat or a 13% LFD as a control cohort (Example 1). HFD feeding progressively increased body and epididymal fat pad weights as well as fasting glucose levels (FIG. 2A-B). Interestingly, unlike CD8$^+$ T cells, abundance of type 1 NKT cells in adipose tissue, in terms of the percentage in total lymphocytes and total cell number per g adipose tissue, gradually decreased with HFD (FIG. 2C-D).

This observation was further confirmed in adult murine ob/ob genetic obesity model: the percent of NKT cells in adipose tissues were significantly reduced in ob/ob mice (FIG. 2E-F). The reduction of NKT in adipose tissue of ob/ob mice was not due to defects in NKT cell development or emigration from the thymus as the level of NKT cells in lymphoid organs such as spleen was not affected by obesity (FIG. 2G). Taken together, these data suggest that HFD progressively decreases the abundance of NKT cells in adipose tissue.

Example 4

αGalCer Activates Adipose-Resident NKT

Figure 3G:
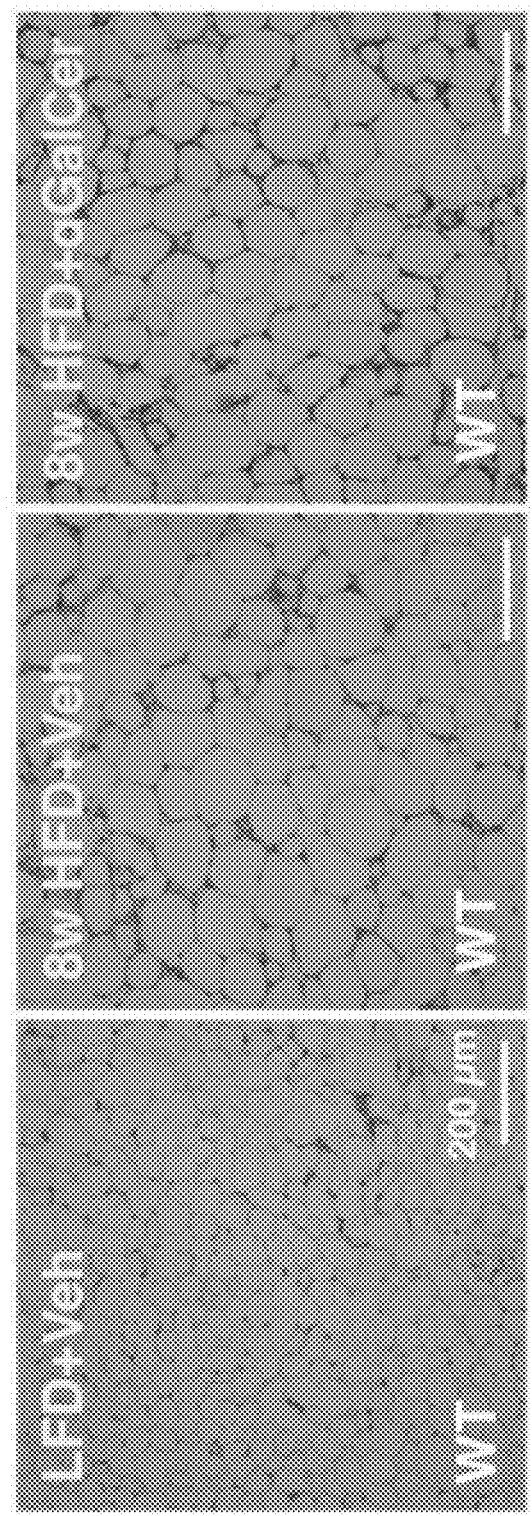
FIG. 3G shows H&E sections of adipose tissue of WT mice of 8 w HFD for the indicated treatments.
Figure 4:
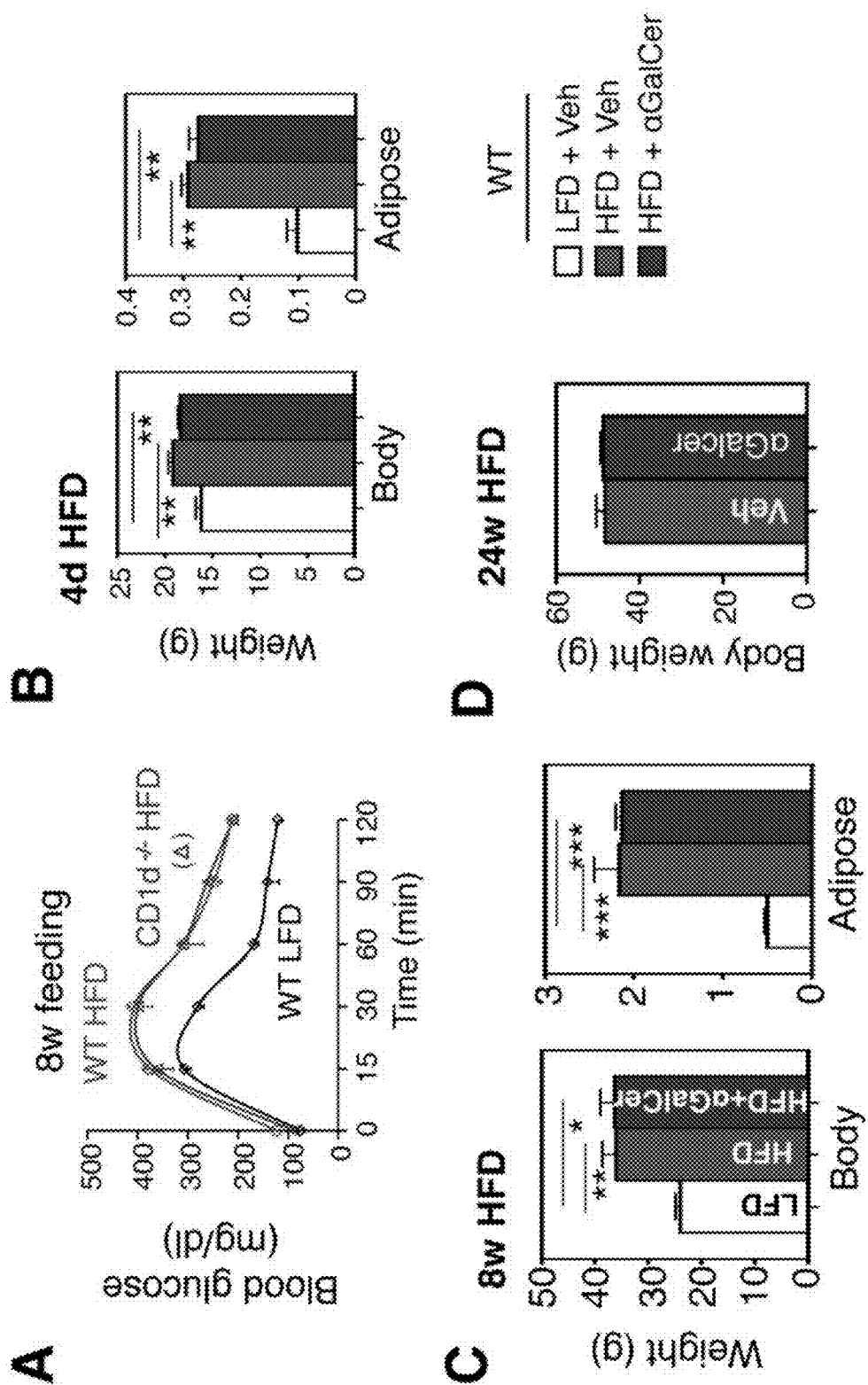
FIG. 4A graphically depicts the results of a glucose tolerance test (GTT) for WT mice on LFD (diamonds), WT on HFD (circles) and CD1d$^{-/-}$ mice on HFD (triangles) for 8-weeks (n=8-9 per cohort, 2 repeats), respectively.
FIGS. 4B-D show the body and epididymal fat weights of mice on LFD (white), HFD with vehicle (grey) or HFD with αGalCer injection (dark) for 4 days, 8 weeks or 24 weeks, respectively. Values represent mean±s.e.m. *, P<0.05, , P<0.01, *, P<0.005.
Figure 5C:
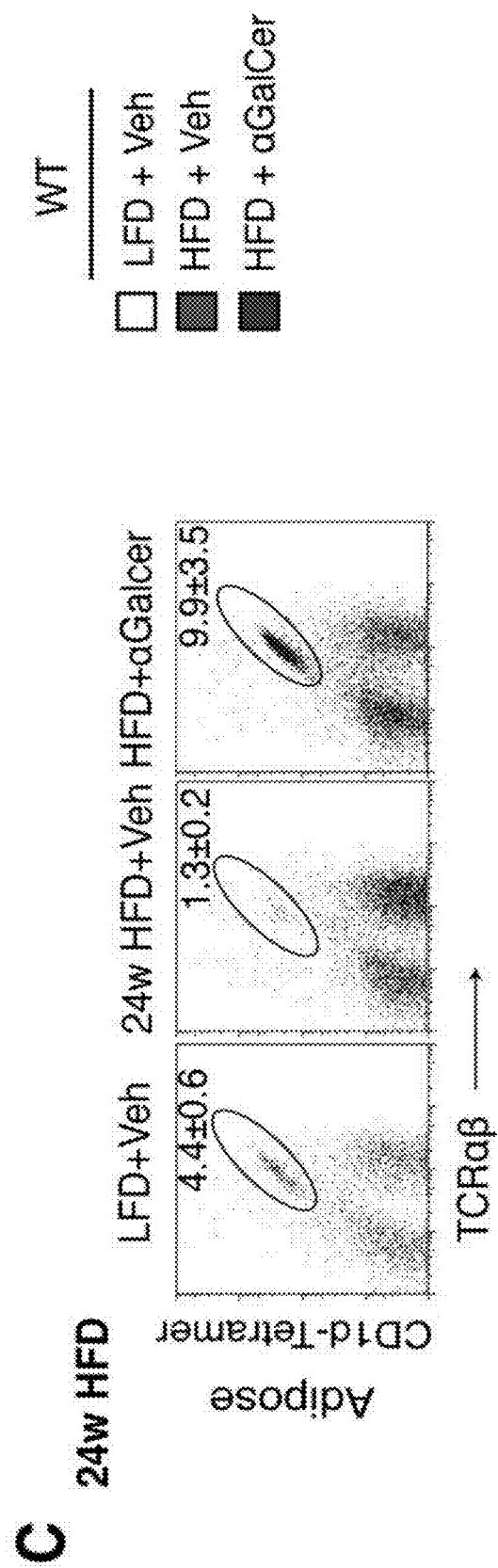
FIG. 5C shows a flow analysis of NKT cells in adipose tissue of 14 w-old mice that have been on LFD, HFD with vehicle or HFD with αGalCer challenge for 24 w (n=3-4 per cohort). Number refers to the percentage of NKT cells in total CD45$^+$ lymphocytes in SVC of adipose tissue. Values represent mean±s.e.m.*, P<0.05, , P<0.01, and *, P<0.005. For panels A and B, the bars represent LFD (white), HFD with vehicle (grey) or HFD with αGalCer injection (dark).

To address whether NKT cells can be targeted therapeutically, a gain-of-function approach was used to stimulate NKT cells in vivo with αGalCer (FIG. 3A). Other studies have established that significant expansion of NKT cells was observed from 2-3 d up to 7 d after the initial αGalCer injection, a process associated with sustained cytokine production up to 7 d (Wilson et al. (2003) Proc Natl Acad Sci USA 100, 10913-10918). To further examine therapeutic effects of NKT cell activation at different stages of obesity, studies were performed in animals that had been on HFD for 4 d, 8 w and 24 w, which represent short-term, long-term and chronic HFD feeding models, respectively.

Accordingly, 6 w-old male mice were fed with either 13% LFD or 60% HFD for indicated period of time from 4 d to 24 w as described in Example 1. αGalCer (Toronto Research Chemicals) was dissolved in pyridine at 2.5 mg/ml and then diluted 1:250 in PBS to prepare 10 μg/ml working solution prior to use. In all experiments, mice were injected i.p. with 200 μl αGalCer (100 ng αGalCer per g body weight). The vehicle control group was injected with PBS with 0.4% pyridine. The dosage and frequency of αGalCer injection were the same for all the gain-of-function experiments unless otherwise indicated. HFD mice were injected with αGalCer or vehicle at day 0 and day 2. GTT was conducted on day 4, followed by sacrificing the mice on (day 5) to harvest adipose tissues (or other tissues as indicated), which were processed for immune cell analysis, frozen for Q-PCR or Western blot, or fixed for H&E staining Flow cytometric analyses of NKT levels and other immune cells were performed on day 5.

For GTT, mice were fasted for 16-18 h followed by injection of glucose (Sigma) at 1 g/kg body weight. Blood glucose was monitored using One-Touch Ultra Glucometer. Fasting insulin levels were measured following a 6 h fast.

While αGalCer injection had no discernible effect on body and epididymal fat weights (FIG. 4B), it caused massive proliferation of NKT cells in adipose tissue (FIG. 3B) with over a 4-fold increase in percentage (FIG. 3C) and 70-fold increase in total cell number (FIG. 5A) in 4 d HFD mice. It also caused milder increases of macrophages and CD8$^+$ T cells (FIG. 5A) in 4 dHFD mice. In line with these observations, H&E staining of WAT sections revealed a significant increase in the number of cells surrounding adipocytes following αGalCer injection (FIG. 3D), and abolished by CD1d deficiency (FIG. 3E), suggesting that the expansion of immune cells including CD8+ T cells and macrophages are NKT-dependent. Similar observations were made in 8 w and 24 w HFD mice (FIGS. 3F-G, 4C-D and 5B-C).

Metabolically, αGalCer challenge improved systemic glucose tolerance in mice at all stages of HFD (FIGS. 6A-C) but had no effect on fasting insulin levels (FIG. 6D). The αGalCer effect on glucose tolerance of HFD mice is NKT cell-dependent as it had no effect in CD1d$^{-/-}$ mice (FIG. 6E). Pointing to the importance of HFD in NKT cell effect, αGalCer injection in mice on LFD had no effect on glucose tolerance (FIG. 6F). Thus, NKT cell activation by αGalCer improves systemic glucose tolerance in obese animals. NKT-deficient CD1d$^{-/-}$ mice fed 8-week HFD exhibited no changes in glucose tolerance as previously observed by others (FIG. 4A; Kotas et al. (2011); Mantell et al. (2011)).

Accordingly, αGalCer injection activates adipose-resident NKT cells and improves systemic glucose homeostasis in obesity.

Example 5

αGalCer Induces Specific M2 Genes and Proteins

Figure 7A:
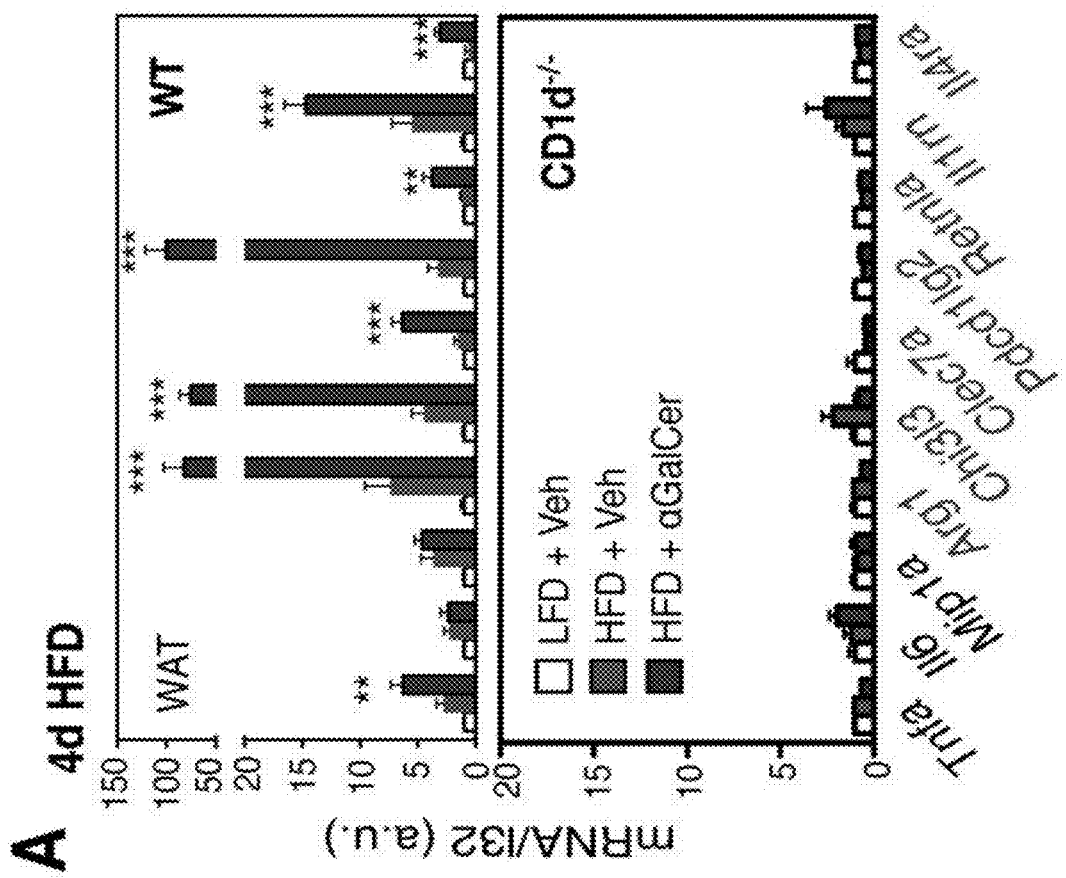
FIG. 7 shows that NKT cell activation increases M2 polarization in adipose tissue of DIO mice. Panel A provides a Q-PCR analysis of M1 genes (first three genes) and M2 genes (remaining six genes) in white adipose tissue (WAT) in WT (upper) and CD1d$^{-/-}$ (lower) mice on 4 d HFD (n=10-15 per cohort; 2-3 repeats). Panel B shows a similar Q-PCR analysis of the same M1 and M2 genes in WAT of 8 w HFD WT mice (n=4-5 per cohort, 2 repeats).
FIGS. 7C and 7D provide a Western blot analysis of Arg1 expression in WAT of WT and CD1d$^{-/-}$ cohorts with vehicle or αGalCer treatment (n=3-4 per cohort, 2 repeats). Each lane represents an independent sample in FIG. 7C. Quantitation is shown in FIG. 7D, with the values of the LFD+veh sample set at 1. Values represent mean±s.e.m. n.s. not significant. *, P<0.05, , P<0.01, and *, P<0.005. For panels A, B and C, the bars represent LFD (white), HFD with vehicle (grey) or HFD with αGalCer injection (dark).
Figure 7B:
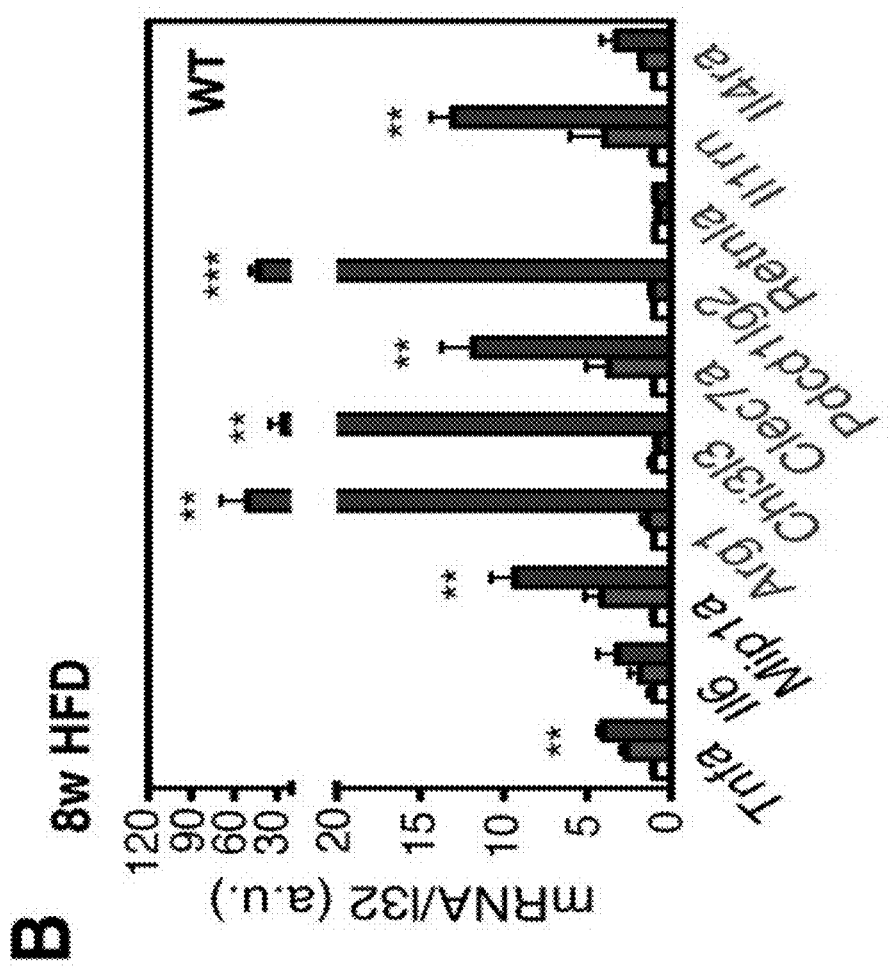
Figure 7C:
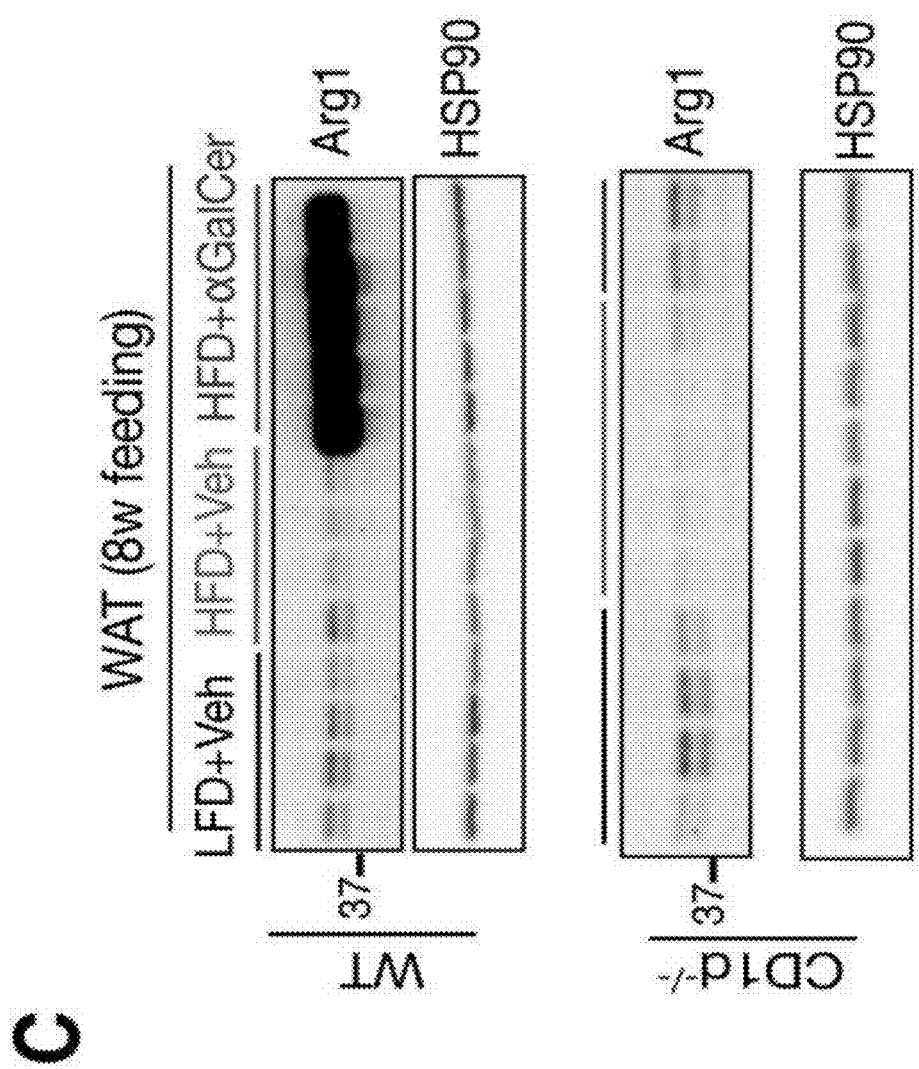
Figure 7D:
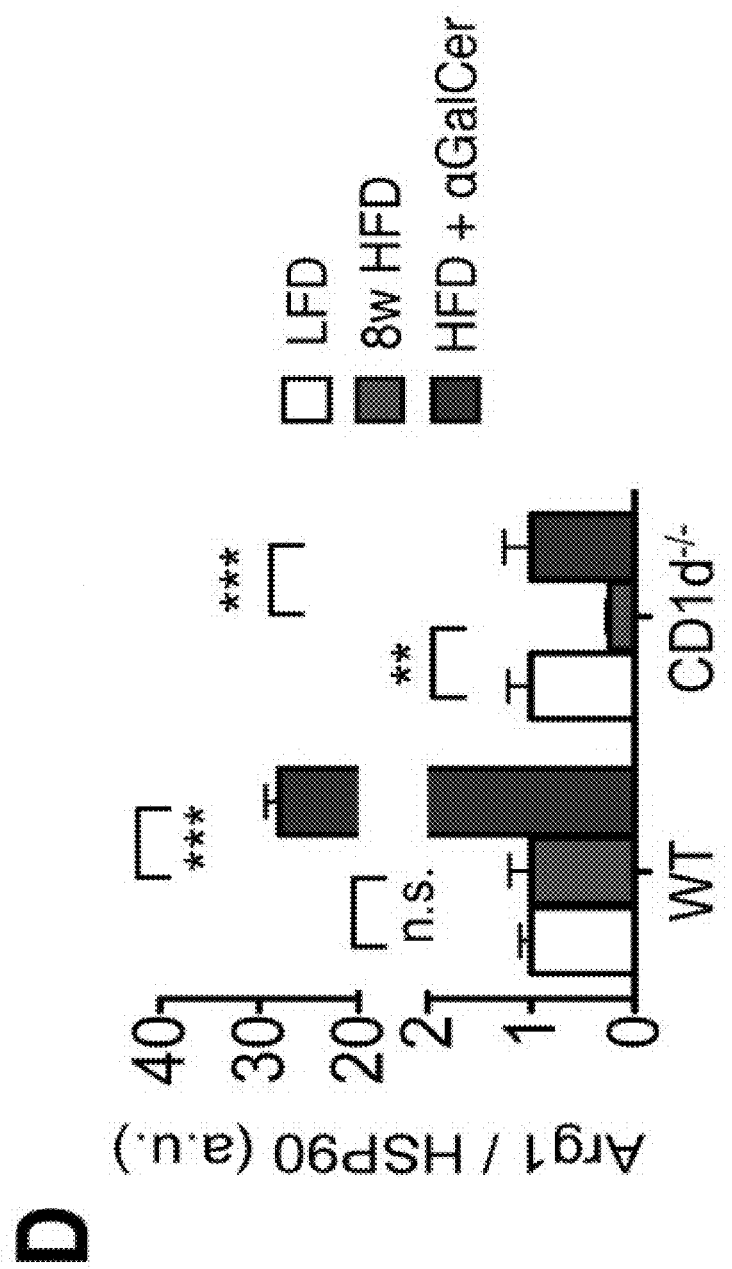
Figure 8A:
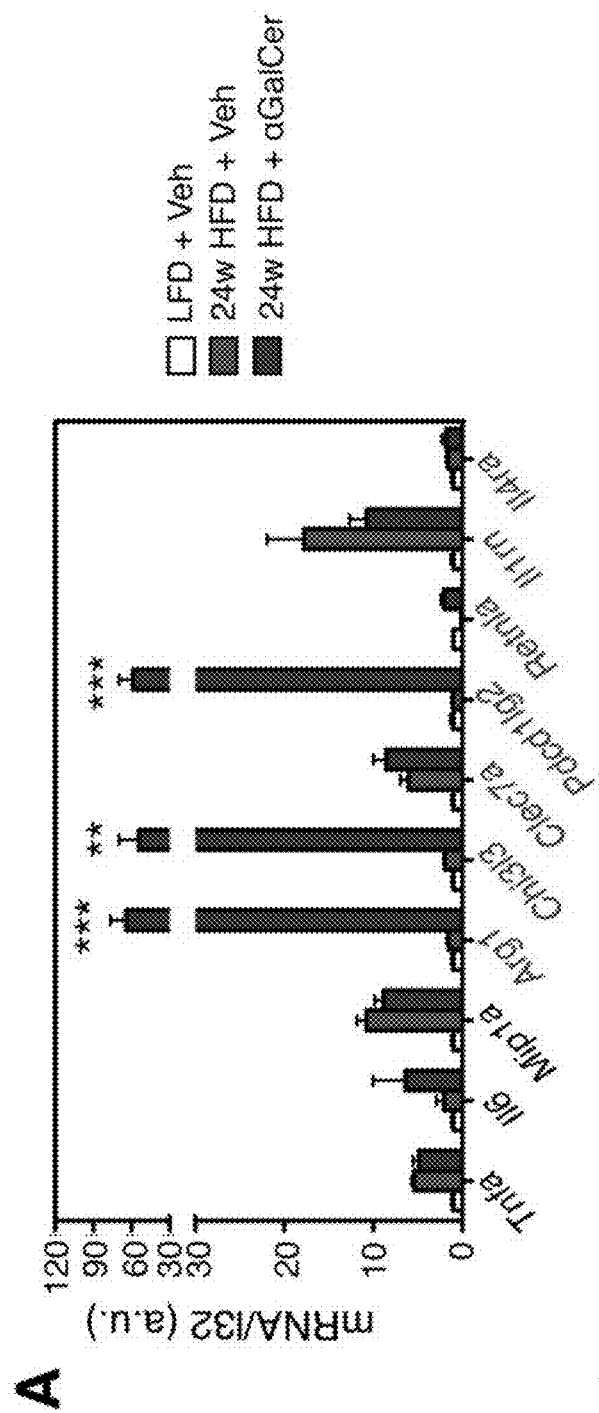
FIG. 8A provides a Q-PCR analysis of adipose tissue of 30 w-old mice that have been on LFD (white), HFD with vehicle (grey) or HFD injected with αGalCer (dark) for 24 w (n=3-4 per cohort).
Figure 8B:
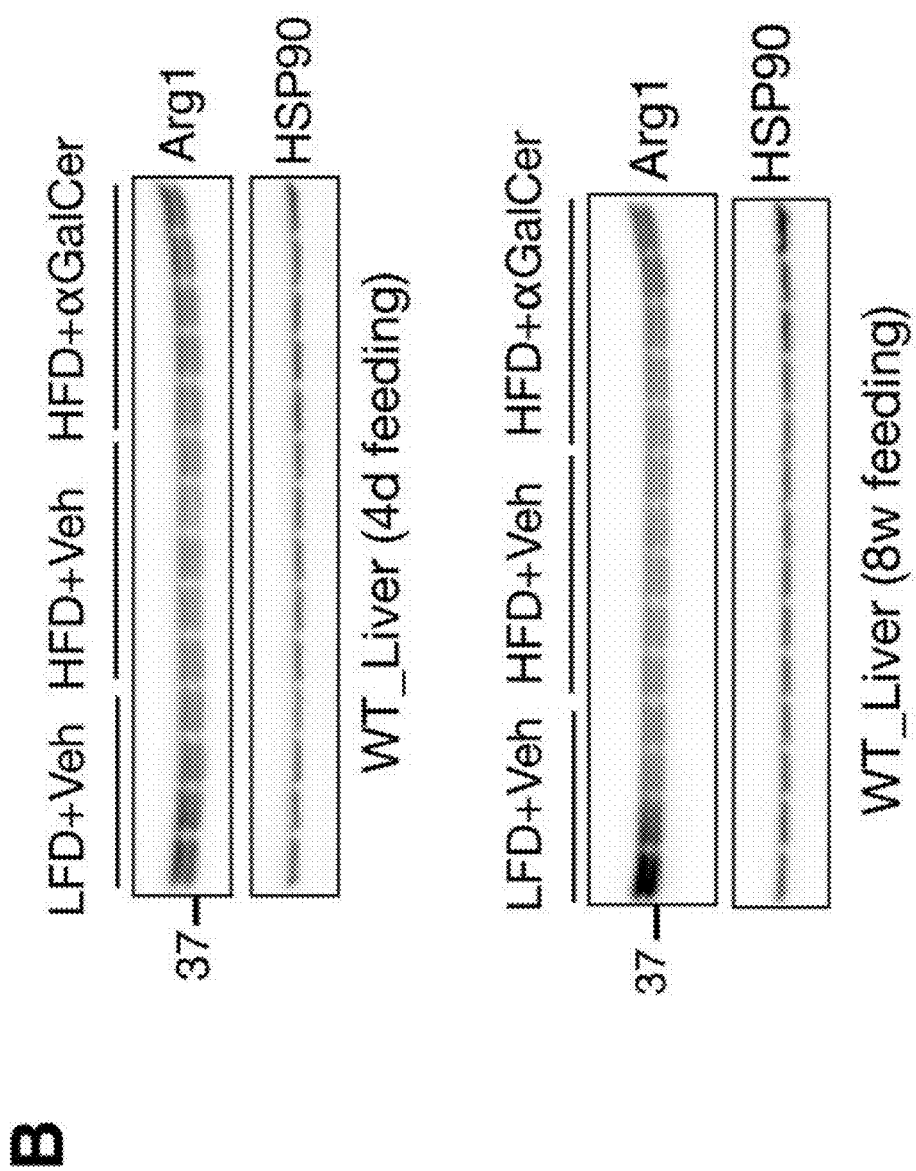
FIG. 8B shows western blots of Arg1 expression in the liver of the three cohorts under 4 d (upper) or 8 w (lower) HFD feeding (n=4-5 per cohort, 2 repeats). HSP90 is a loading control.

To explore possible mechanism underlying the beneficial effect of NKT cell activation, we assessed the inflammatory status of adipose tissue by examining the status of macrophage polarization in the adipose tissue samples obtained in Example 4. αGalCer challenge caused a marked 50-100-fold induction of a subset of M2 genes in adipose tissue in a NKT-dependent manner, including Arg1, Chi3l3 and Pdcd1lg2, and to a much lesser extent, M1 genes in all three HFD models (FIGS. 7A-B and 8A). This observation was further supported by the protein level of a key M2 macrophage marker: Arg1 protein was significantly induced in response to αGalCer in WT WAT but abolished in CD1d$^{-/-}$ WAT (FIG. 7C-D). Intriguingly, this effect was limited to adipose tissue and was not observed in the liver (FIG. 8B). Hence, it appears that NKT cell activation by αGalCer promotes M2 polarization in adipose tissue in obesity.

Example 6

Global Effect of αGalCer in Adipose Tissue

Microarray analyses of WAT were performed as described (39) with four groups of mice (n=3-4 per cohort) as follows: WT+veh, WT+αGalCer, CD1d$^{-/-}$+veh and CD1d$^{-/-}$+αGalCer. All mice were on 4 d HFD feeding with two αGalCer injections at day 0 and day 2. For gene-set enrichment analysis (GSEA), ranking was based on the normalized enrichment score, which reflected the degree to which a gene set in a certain pathway was overrepresented at the top (upregulated) or bottom (downregulated) of the ranked gene list and was corrected for gene set size. Data have been deposited into the GEO datasets (GSE36032). The array data of IL-4-treated mouse BMDM for 10 days were obtained from the Gene Expression Omnibus (GEO) database with accession number GSE25088 (Szanto A. et al. (2010)).

Figure 10A:
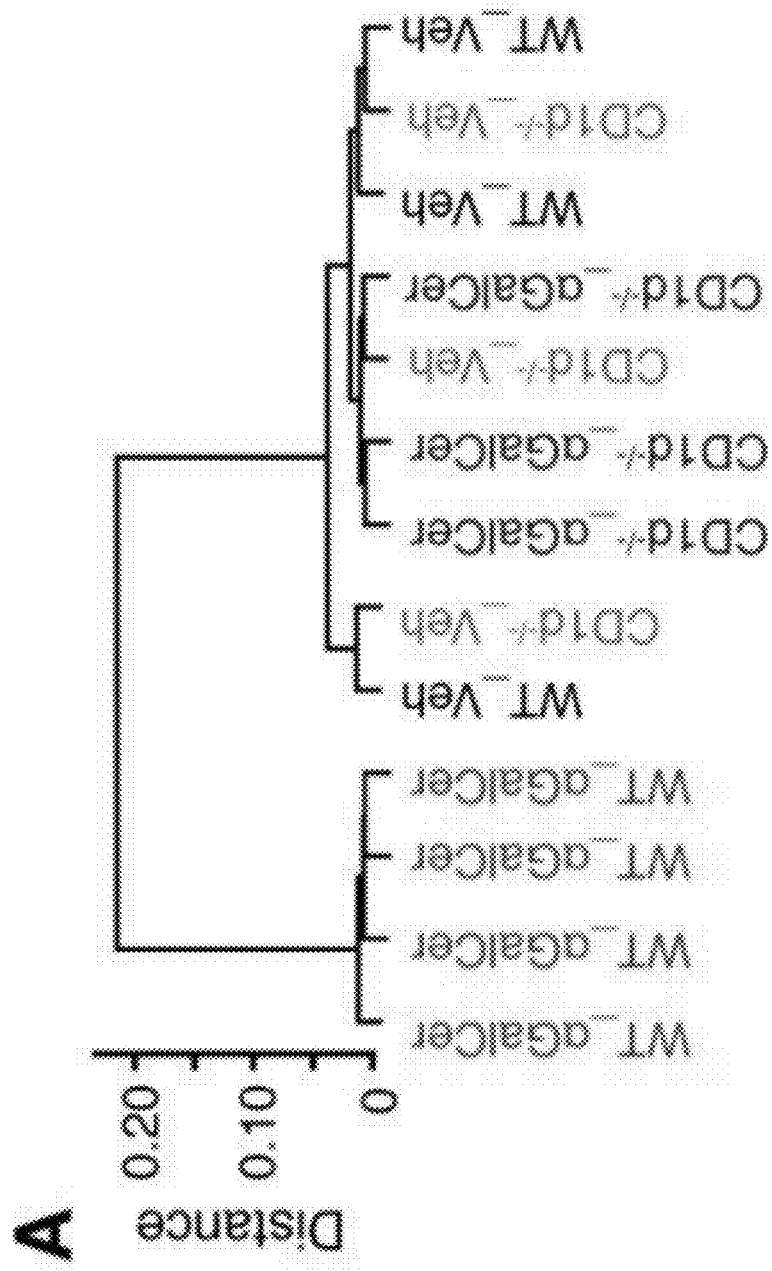
FIG. 10A presents a dendrogram showing the hierarchical clustering of microarray data of individual mice establishes a separation of the WT mice injected with αGalCer from the other groups.
Figure 10B:
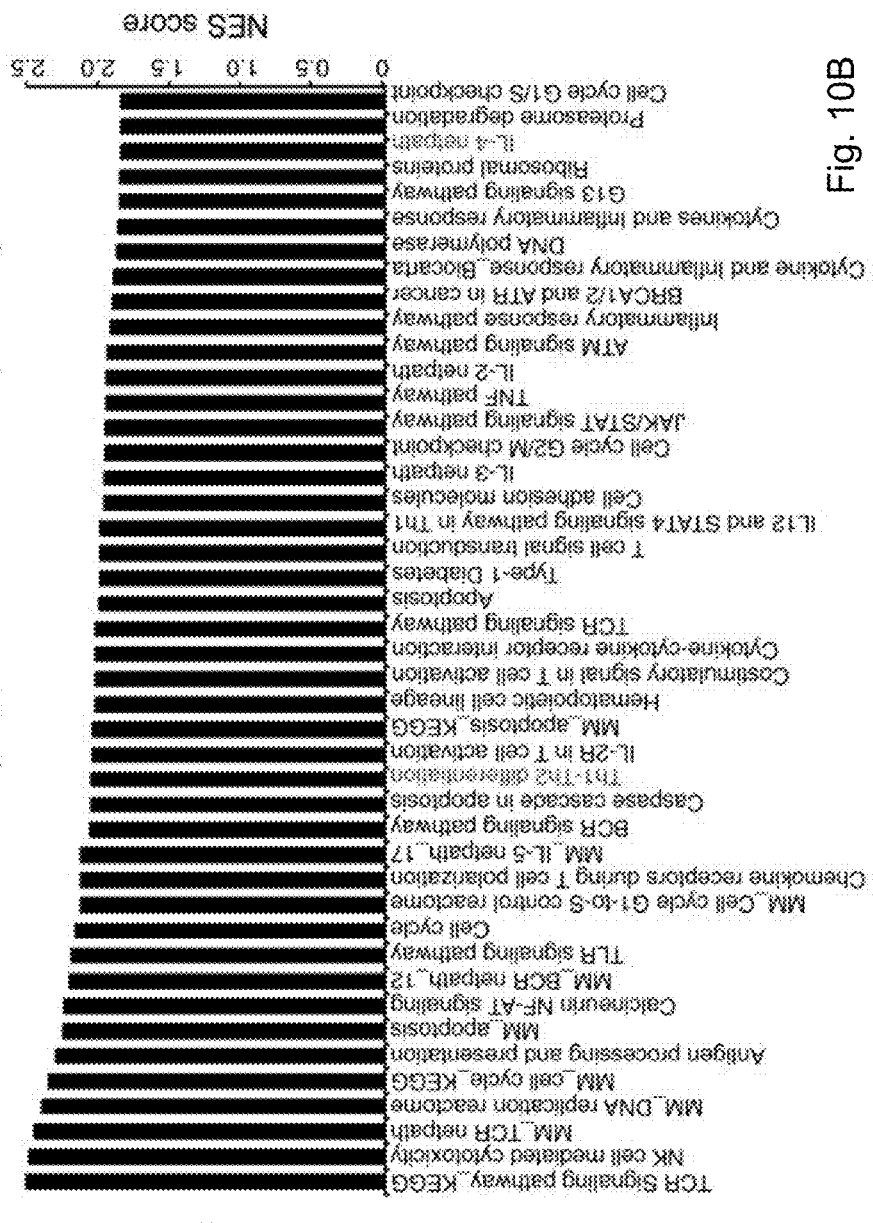
FIG. 10B shows the NES for the most significant upregulated pathways identified by GSEA (all with false discovery rate q-value<0.0003) in WT mice injected with αGalCer. The "$T_H1/T_H2$ differentiation" and "IL-4 pathway" highlighted in pale grey (red).
Figure 10C:
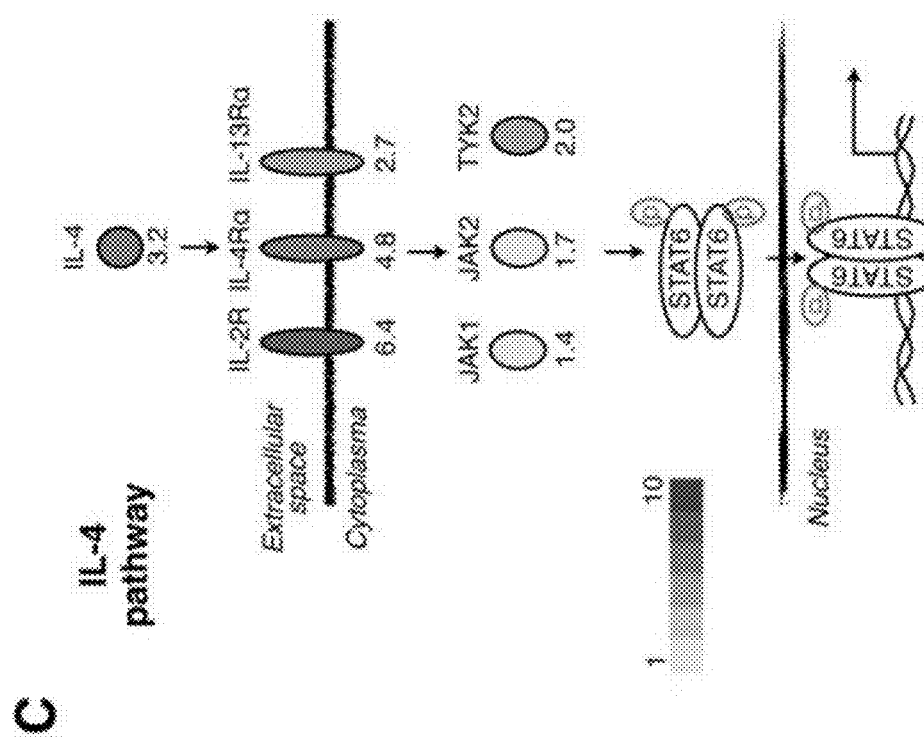
FIG. 10C diagrammatically presents the canonical IL-4 pathway and illustrates the fold induction of each key component by αGalCer in WAT. STAT6 is activated by phosphorylation and not at the transcriptional level. The color scale is shown at the bottom.

Because αGalCer effects on macrophage polarization were similar among all three DIO models, the microarray analysis was performed in adipose tissues harvested from the 4 d HFD model, where a relatively higher signal-to-noise ratio was anticipated compared to that of long-term HFD. Indeed, the expression of 1,556 genes was significantly increased by more than 2-fold in an absolute NKT-dependent manner (FIG. 9A). Hierarchical clustering of microarray data of individual mice depicted as dendogram showed clear separation of WT mice injected with αGalCer from the other groups. GSEA indicated pronounced induction of many pathways related to immune functions, including the "$T_H1/T_H2$ differentiation" and the "IL-4 pathway" (FIG. 10B). In comparison with a pre-existing dataset (40), we found that 40% of genes upregulated by IL-4 in macrophages were also induced by αGalCer in WAT (FIG. 9C). Furthermore, most components of the canonical IL-4 signaling pathway were induced by αGalCer in WAT (FIG. 10C). Pointing to a potential role of IL-4, seven out of the top 10 αGalCer-induced genes in WAT were also highly upregulated in IL-4-treated macrophages (40), and many were classical M2 genes such as Chi3l3 (138 fold, αGalCer vs. veh in WT WAT), pdcd1lg2 (53 fold) and Arg1 (32 fold) (FIG. 9B).

The array data was further supported by Q-PCR and Western blot analyses of Arg1 levels of WAT (FIGS. 7A and 9D-E). Further as direct support for the elevated IL-4 signaling in WAT, Il4 mRNA levels in WAT were highly induced by αGalCer treatment in an NKT-dependent manner (FIG. 9F). Thus, αGalCer-mediated NKT cell activation increases IL-4 signaling in adipose tissue.

Example 7

αGalCer-Mediated NKT Cell Activation in IL-4$^{-/-}$ Mice

The physiological importance of IL-4 in αGalCer-mediated NKT cell activation was assessed in IL-4$^{-/-}$ mice. For this study, 6-7 w-old WT or IL-4$^{-/-}$ mice were placed on either LFD or HFD for 4 d with two αGalCer or vehicle injections prior to metabolic phenotyping. While both body and adipose weights were comparable among WT and IL-4$^{-/-}$ cohorts following 4-day HFD (FIG. 11A), loss of IL-4 completely abolished the αGalCer effect in glucose tolerance (FIG. 11B-C) and reduced the total number of infiltrating immune cells in adipose tissue following αGalCer injection (FIG. 12A). Indeed, total lymphocytes in WAT of IL-4$^{-/-}$ mice were reduced by approximately 40% relative to WT cohorts (FIG. 12B).

Figure 11E:
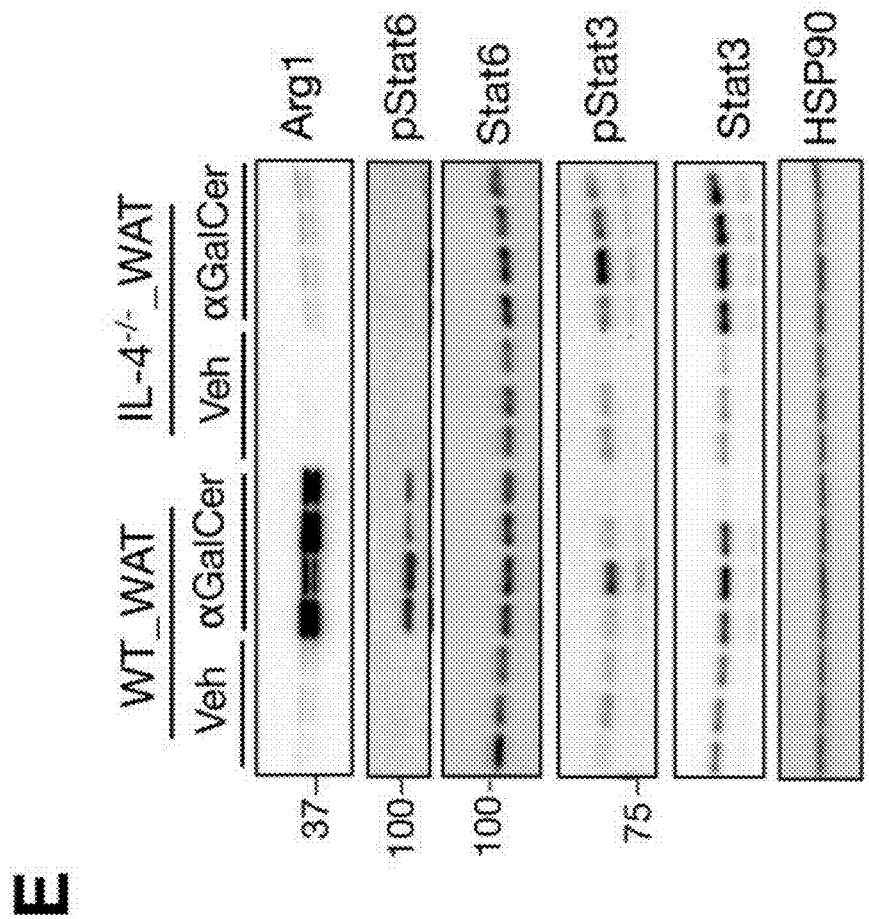
FIG. 11E shows Western blots for Arg1, (pY-) STAT6 and (pY-) STAT3 in WAT of WT and IL-4$^{-/-}$4 dHFD mice injected with vehicle or αGalCer (n=3-5 per cohort, 2 repeats).

Loss of IL-4 markedly attenuated the αGalCer-mediated induction of M2 genes Arg1, Chi3l3, and Pdcd1lg2 (FIG. 11D) and Arg1 protein in WAT (FIG. 11E-F). Moreover, loss of IL-4 completely abolished tyrosine phosphorylation (p-Y) of STAT6, but not p-Y of STAT3, in WAT following αGalCer-mediated NKT activation (FIG. 11E-F). Providing further support to the significance of adipose tissue in mediating NKT effect in vivo, hepatic STAT6 was not activated by αGalCer (FIG. 11G).

Figure 12C:
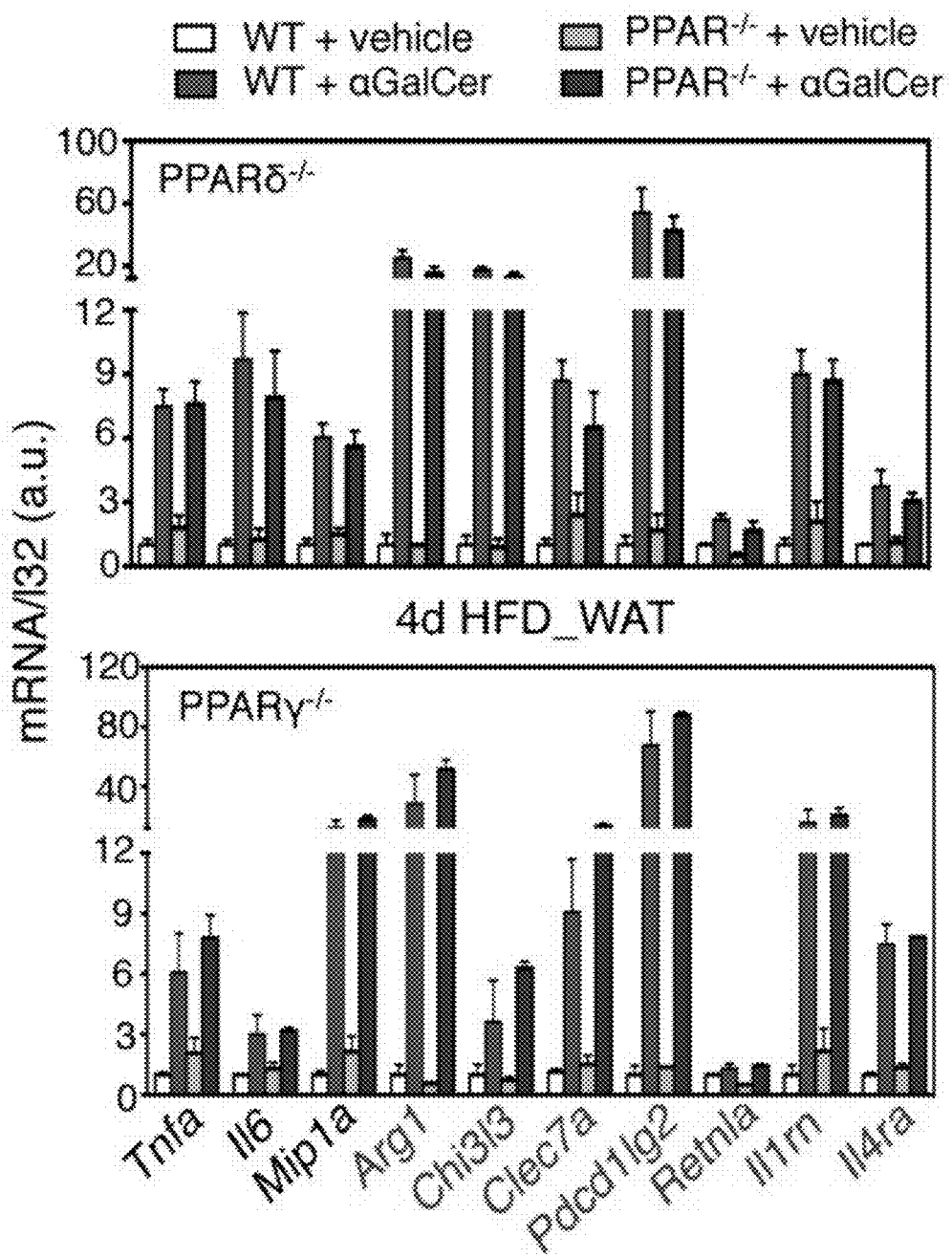
FIG. 12C provides a Q-PCR analysis for the same M1 and M2 genes in FIG. 7 from WAT of WT, PPARγ$^{-/-}$ (lower panel), PPARδ$^{-/-}$ (upper panel) mice following 4 day HFD feeding with or without αGalCer injection. Data normalized to "WT+vehicle" whose value was set at 1. Values represent mean±s.e.m. , P<0.01, and *, P<0.005. For all bar graphs, from left to right, the bars represent WT with vehicle injection (white), WT with αGalCer injection (red), IL-4$^{-/-}$ with vehicle injection (green) and IL-4$^{-/-}$ with αGalCer injection (blue).

Finally, it has been shown that the IL-4/STAT6 effect may be mediated by the activities of nuclear receptors (PPARγ or PPARβ/δ) in macrophages (Chawla (2010)). However, αGalCer-mediated induction of M2 genes was not affected in WAT of myeloid cell-specific PPARγ or PPARβ/δ-deficient animals when compared to WT control littermates (FIG. 12C). Thus, NKT cells regulate macrophage polarization and exert metabolic control largely through the IL-4/STAT6 axis in obese adipose tissue, in a PPARγ- and PPARβ/δ-independent manner.

Example 8

NKT in Human Obesity

General Methods.

39 healthy premenopausal adult Chinese women including 25 lean individuals with BMI<25 Kg/m$^2$ and 14 overweight/obese subjects with BMI≥25 Kg/m$^2$, undergoing elective abdominal surgery for benign, non-infective gynecological were recruited. Pre-operative assessment was carried out within one week of the operation. Anthropometric parameters (body weight, height, waist circumference and blood pressure) were measured, and body composition was determined by bioelectric impedance analysis (Tanita Body Composition Analyzer TBF-410, Japan). All subjects underwent an oral glucose tolerance test (OGTT) with 75 g glucose. Fasting plasma glucose and 2 h glucose levels at OGTT were measured by hexokinase method on a Hitachi 747 analyzer (Roche). Insulin was measured by microparticle enzyme immunoassay (Abbott Laboratories). HOMA index was calculated to estimate insulin resistance (IR): HOMA-IR=fasting glucose (mM)×fasting insulin (mIU/L)/22.5 (Matthews et al. (1985) *Diabetologia* 28, 412-419). During the operation, visceral adipose tissues (about 8 cm$^3$ each) were collected aseptically, and transported immediately to the laboratory for RNA extraction and Q-PCR analysis as described below.

Q-PCR Analysis of NKT Cells in Human Adipose Tissues.

Following RNA extraction using the Qiagen mini-RNA purification kit, 1 µg of total RNA from each sample was reverse-transcribed. The relative abundance of each gene was determined by Q-PCR on a Prism 7000 sequence detection system (Applied Biosystems), and was normalized against 18S rRNA. Two primer sets were used to detect NKT cell markers in human adipose tissue: one for detecting the splicing event of TCR alpha chain covering around the V-J-C rearrangement region with forward primer at TRAV10 (Vα24, Chr. 14) and reverse primer at TRAC (TCR α chain constant region, Chr. 14)—oligo set 1, fragment size 230 bp (K is et al. (2007) *J Leukoc Biol* 81, 654-662). The other primer set detected the use of TRAV10 (Vα24)—oligo set 2, fragment size 417 bp (Vijayanand et al. (2007) *N Engl J Med* 356, 1410-1422). A primer set for a common T cell gene TRBC2 (TCR β chain constant 2, chr. 7) (Vijayanand et al. (2007) *N Engl J Med* 356, 1410-1422) was included as a control for all T cells (oligo set 3, fragment size 104 bp). Primer sequences are listed in Table 2.

Results.

The abundance of NKT cells in visceral adipose tissues collected from 25 lean and 14 overweight/obese Asian female subjects were analyzed (Table 3; values are mean±standard error).

As most CD1d-restricted type 1 human NKT cells express an invariant TCR Vα24 (8,41,42), Q-PCR was used to quantitate the levels of Vα24-containing mRNA or Vα24-associated Vα24-Cα splicing event in adipose tissue. Strikingly, Vα24 NKT cells in adipose tissue decreased with BMI (FIG. 13A). Total T cells (CD4, CD8 and NKT cells) exhibited an opposite trend (FIG. 13B). Bivariant correlation analysis further revealed that the levels of Vα24 NKT cells in adipose tissue were inversely correlated with insulin resistance as measured by homeostasis model assessment (HOMA) index (FIG. 13C) and glucose levels at the 2 h point of OGTT (FIG. 13D). Thus, the abundance of NKT cells in adipose tissue negatively correlates with BMI, insulin resistance and fasting glucose in humans.

TABLE 3

Clinical characteristics of lean and overweight/obese human subjects

| | Lean subjects (N = 25) | Overweight/obese subjects (N = 14) | P value |
|---|---|---|---|
| Age (years) | 42.5 ± 7.3 | 44.9 ± 5.6 | 0.089 |
| BMI (Kg/m$^2$) [a] | 21.7 ± 2.1 | 28.6 ± 3.3 | <0.001 |
| Fasting glucose (mM) [b] | 4.7 ± 0.4 | 4.8 ± 0.5 | 0.363 |
| 2 h glucose (mM) [c] | 5.8 ± 0.9 | 7.5 ± 1.0 | <0.01 |
| Fasting insulin (mIU/L) [b] | 3.8 ± 0.6 | 5.7 ± 0.9 | 0.016 |
| HOMA-IR [d] | 1.2 ± 0.2 | 1.8 ± 0.3 | <0.01 |

[a] BMI: BMI cutoff from lean and overweight/obese is 25.
[b] Fasting glucose/insulin: glucose or insulin levels after an overnight 16 h fast.
[c] 2 h glucose: glucose levels at the end of OGTT, i.e. the 2 h time point.
[d] HOMA-IR = [fasting glucose (mM) × fasting insulin (mIU/L)]/22.5

Example 9

Model for NKT in Obesity

Figure 14A:
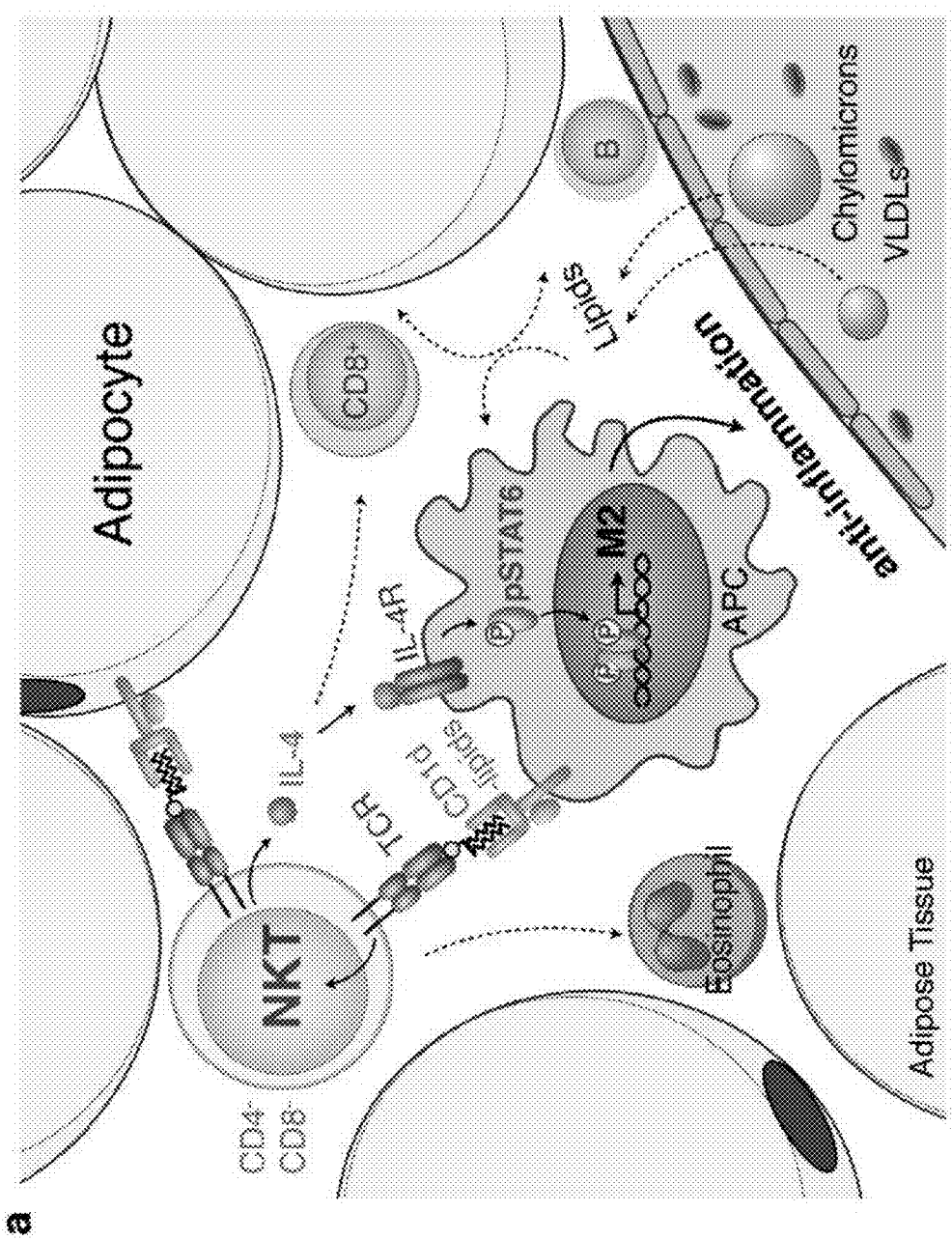
FIG. 14A illustrates a cellular model for NKT in Obesity.

FIG. 14A shows that adipose tissue possesses predominantly CD4$^-$CD8$^-$ type 1 NKT cells with lipid-sensing capability. When activated, these cells promote TH2 responses and reduce inflammation in SVC of adipose tissue via the IL-4/STATE signaling axis. NKT cells, and possibly other cells, appear to contribute to the "IL-4" pool in adipose tissue.

Figure 14B:
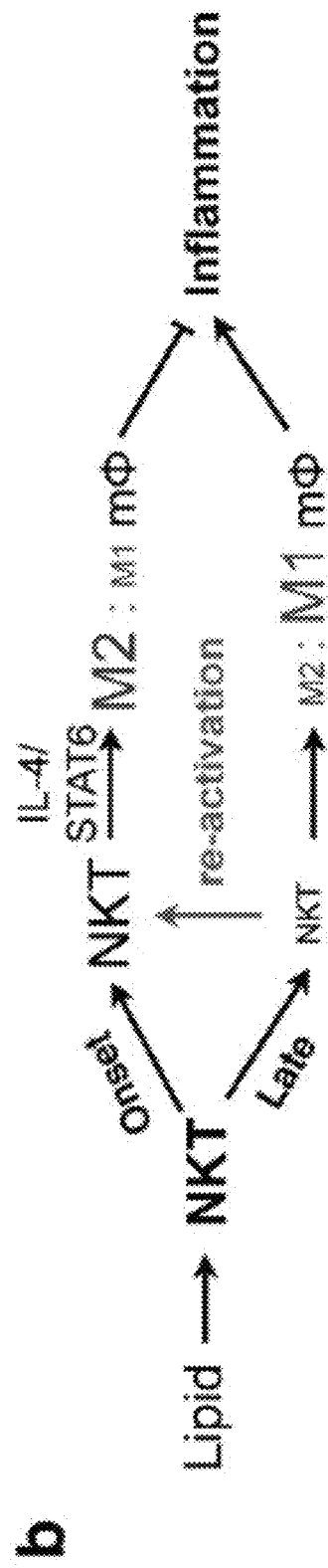
FIG. 14B depicts a mechanism of lipid activation of NKT cells at the onset and at late stage of obesity.

The actions of NKT cells at different stages of obesity are shown in FIG. 14B. At the onset of obesity, NKT cells are activated and thereby enhance M2 polarization via the IL-4/STATE signaling axis. In contrast, at the late stages of obesity, NKT cells appear in a "quiescent" or "anergic" state, which may provide a permissive environment for the development of pro-inflammatory responses with massive infiltration of other immune cells such as B cells, macrophages and CD8+ T cells. Hence, loss of NKT cells has a significant impact on inflammation at the onset of obesity, but less so at the late stages of obesity. Conversely, activation of NKT cells at both onset and late stages of obesity enhances TH2 response and attenuates inflammation, improves glucose homeostasis as well as insulin resistance in adipose tissue.

We claim:

1. A method to screen for an activator of adipose-resident NKT cells which comprises
   (a) feeding at least one mouse a high fat diet (HFD) for at least about 4 days up to about 24 weeks;
   (b) administering a candidate activator to said at least one mouse;
   (c) sacrificing said at least one mouse from about 4 to about 7 days after administering said activator;
   (d) preparing white adipose tissue (WAT) from said at least one mouse; and
   (e) detecting whether (i) said WAT contains increased expression, relative to expression in WAT from a control mouse of any one or more of IL-4, IL-13, IL-12, Arginase 1 (Arg1), chitinase 3-like 3 (Chi3l3), C-type lectin domain family 7, member a (Clec7a), Programmed cell death 1 ligand 2 (Pdcl1g2), Resistin like alpha (Retn1a), Interleukin 1 receptor antagonist (IL-1rn), and Interleukin receptor 4 alpha (IL-4ra), (ii) M2 macrophage polarization increases in said WAT relative to that in WAT from said control mouse, (iii) whether at least one $T_H2$ cytokine is produced, or a combination of (i), (ii) or (iii), wherein the control mouse is fed with the HFD and is not administered with said activator, thereby determining that said candidate activator is an activator of adipose-resident NKT cells.

2. The method of claim 1, wherein increased expression is detected by a Northern blot, by a nucleic acid hybridization technique, by RNA-Seq, by PCR, by ELISA, by immunoblotting or by immunohistochemical staining.

3. The method of claim 1, wherein said at least one mouse is a wild-type mouse or has a genetic predisposition to obesity.

4. The method of claim 1, wherein said at least one $T_H2$ cytokine is selected from the group consisting of IL-4, IL-10, IL-12 and IL-13.

* * * * *

UNITED STATES PATENT AND TRADEMARK OFFICE
CERTIFICATE OF CORRECTION

PATENT NO. : 9,623,083 B2  
APPLICATION NO. : 14/241482  
DATED : April 18, 2017  
INVENTOR(S) : Ling Qi et al.

Page 1 of 1

It is certified that error appears in the above-identified patent and that said Letters Patent is hereby corrected as shown below:

On the Title Page

Item (60) should read:
Related U.S. Application Data
(60) Provisional application No. 61/528,995, filed on Aug. 30, 2011 and provisional application No. 61/544,455, filed on Oct. 7, 2011.

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 30

<210> SEQ ID NO 1
<211> LENGTH: 22
<212> TYPE: DNA
<213> ORGANISM: Artificial Sequence
<220> FEATURE:
<223> OTHER INFORMATION: Tnfa forward primer

<400> SEQUENCE: 1
tcagccgatt tgctatctca ta                                          22

<210> SEQ ID NO 2
<211> LENGTH: 22
<212> TYPE: DNA
<213> ORGANISM: Artificial Sequence
<220> FEATURE:
<223> OTHER INFORMATION: Tnfa reverse primer

<400> SEQUENCE: 2
agtacttggg cagattgacc tc                                          22

<210> SEQ ID NO 3
<211> LENGTH: 20
<212> TYPE: DNA
<213> ORGANISM: Artificial Sequence
<220> FEATURE:
<223> OTHER INFORMATION: Il4 forward primer

<400> SEQUENCE: 3
catgggaaaa ctccatgctt                                             20

<210> SEQ ID NO 4
<211> LENGTH: 20
<212> TYPE: DNA
<213> ORGANISM: Artificial Sequence
<220> FEATURE:
<223> OTHER INFORMATION: Il4 reverse primer

<400> SEQUENCE: 4
tggactcatt catggtgcag                                             20

<210> SEQ ID NO 5
<211> LENGTH: 22
<212> TYPE: DNA
<213> ORGANISM: Artificial Sequence
<220> FEATURE:
<223> OTHER INFORMATION: Il6 forward primer

<400> SEQUENCE: 5
agacaaagcc agagtccttc ag                                          22

<210> SEQ ID NO 6
<211> LENGTH: 22
<212> TYPE: DNA
<213> ORGANISM: Artificial Sequence
<220> FEATURE:
<223> OTHER INFORMATION: Il6 reverse primer

<400> SEQUENCE: 6
tgccgagtag atctcaaagt ga                                          22

<210> SEQ ID NO 7
<211> LENGTH: 23
<212> TYPE: DNA
<213> ORGANISM: Artificial Sequence
<220> FEATURE:
<223> OTHER INFORMATION: Mip1a forward primer

<400> SEQUENCE: 7
ttctctgtac catgacactc tgc                                         23

<210> SEQ ID NO 8
<211> LENGTH: 21
<212> TYPE: DNA

```
<213> ORGANISM: Artificial Sequence
<220> FEATURE:
<223> OTHER INFORMATION: Mip1a reverse primer

<400> SEQUENCE: 8
cgtggaatct tccggctgta g                                         21

<210> SEQ ID NO 9
<211> LENGTH: 22
<212> TYPE: DNA
<213> ORGANISM: Artificial Sequence
<220> FEATURE:
<223> OTHER INFORMATION: Arg1 forward primer

<400> SEQUENCE: 9
ctccaagcca aagtccttag ag                                        22

<210> SEQ ID NO 10
<211> LENGTH: 22
<212> TYPE: DNA
<213> ORGANISM: Artificial Sequence
<220> FEATURE:
<223> OTHER INFORMATION: Arg1 reverse primer

<400> SEQUENCE: 10
aggagctgtc attagggaca tc                                        22

<210> SEQ ID NO 11
<211> LENGTH: 22
<212> TYPE: DNA
<213> ORGANISM: Artificial Sequence
<220> FEATURE:
<223> OTHER INFORMATION: Chi3l3 forward primer

<400> SEQUENCE: 11
ggctcaagga caacaattta gg                                        22

<210> SEQ ID NO 12
<211> LENGTH: 22
<212> TYPE: DNA
<213> ORGANISM: Artificial Sequence
<220> FEATURE:
<223> OTHER INFORMATION: Chi3l3 reverse primer

<400> SEQUENCE: 12
actgtggaaa aaccgttgaa ct                                        22

<210> SEQ ID NO 13
<211> LENGTH: 20
<212> TYPE: DNA
<213> ORGANISM: Artificial Sequence
<220> FEATURE:
<223> OTHER INFORMATION: Clec7a forward primer

<400> SEQUENCE: 13
tcattgaaag ccaaacatcg                                           20

<210> SEQ ID NO 14
<211> LENGTH: 20
<212> TYPE: DNA
<213> ORGANISM: Artificial Sequence
<220> FEATURE:
<223> OTHER INFORMATION: Clec7a reverse primer

<400> SEQUENCE: 14
cctggggagc tgtatttctg                                           20
```

<210> SEQ ID NO 15
<211> LENGTH: 20
<212> TYPE: DNA
<213> ORGANISM: Artificial Sequence
<220> FEATURE:
<223> OTHER INFORMATION: Pdcllg2 forward primer

<400> SEQUENCE: 15
acgtggccac ttcatgtttt                                         20

<210> SEQ ID NO 16
<211> LENGTH: 20
<212> TYPE: DNA
<213> ORGANISM: Artificial Sequence
<220> FEATURE:
<223> OTHER INFORMATION: Pdcllg2 reverse primer

<400> SEQUENCE: 16
tcttgagggt ttcccatcag                                         20

<210> SEQ ID NO 17
<211> LENGTH: 20
<212> TYPE: DNA
<213> ORGANISM: Artificial Sequence
<220> FEATURE:
<223> OTHER INFORMATION: Retnla forward primer

<400> SEQUENCE: 17
tatgaacaga tgggcctcct                                         20

<210> SEQ ID NO 18
<211> LENGTH: 20
<212> TYPE: DNA
<213> ORGANISM: Artificial Sequence
<220> FEATURE:
<223> OTHER INFORMATION: Retnla reverse primer

<400> SEQUENCE: 18
agctgggttc tccacctctt                                         20

<210> SEQ ID NO 19
<211> LENGTH: 20
<212> TYPE: DNA
<213> ORGANISM: Artificial Sequence
<220> FEATURE:
<223> OTHER INFORMATION: Il1rn forward primer

<400> SEQUENCE: 19
ttgtgccaag tctggagatg                                         20

<210> SEQ ID NO 20
<211> LENGTH: 20
<212> TYPE: DNA
<213> ORGANISM: Artificial Sequence
<220> FEATURE:
<223> OTHER INFORMATION: Il1rn reverse primer

<400> SEQUENCE: 20
ttctcagagc ggatgaaggt                                         20

<210> SEQ ID NO 21
<211> LENGTH: 20
<212> TYPE: DNA
<213> ORGANISM: Artificial Sequence
<220> FEATURE:

<223> OTHER INFORMATION: Il4ra forward primer

<400> SEQUENCE: 21
gaagccagga gtcaaccaag                              20

<210> SEQ ID NO 22
<211> LENGTH: 20
<212> TYPE: DNA
<213> ORGANISM: Artificial Sequence
<220> FEATURE:
<223> OTHER INFORMATION: Il4ra reverse primer

<400> SEQUENCE: 22
atacagcgca ccacactgac                              20

<210> SEQ ID NO 23
<211> LENGTH: 23
<212> TYPE: DNA
<213> ORGANISM: Artificial Sequence
<220> FEATURE:
<223> OTHER INFORMATION: Oligo 1 forward primer

<400> SEQUENCE: 23
gatatacagc aactctggat gca                          23

<210> SEQ ID NO 24
<211> LENGTH: 23
<212> TYPE: DNA
<213> ORGANISM: Artificial Sequence
<220> FEATURE:
<223> OTHER INFORMATION: Oligo 1 reverse primer

<400> SEQUENCE: 24
ggcagacaga cttgtcactg gat                          23

<210> SEQ ID NO 25
<211> LENGTH: 21
<212> TYPE: DNA
<213> ORGANISM: Artificial Sequence
<220> FEATURE:
<223> OTHER INFORMATION: Oligo 2 forward primer

<400> SEQUENCE: 25
aagcatctga cgaccttctt g                            21

<210> SEQ ID NO 26
<211> LENGTH: 21
<212> TYPE: DNA
<213> ORGANISM: Artificial Sequence
<220> FEATURE:
<223> OTHER INFORMATION: Oligo 2 reverse primer

<400> SEQUENCE: 26
aacaggacct ctcccagtat c                            21

<210> SEQ ID NO 27
<211> LENGTH: 22
<212> TYPE: DNA
<213> ORGANISM: Artificial Sequence
<220> FEATURE:
<223> OTHER INFORMATION: Oligo 3 forward primer

<400> SEQUENCE: 27
cagcgagccc tactcaaatt ag                           22

```
<210> SEQ ID NO 28
<211> LENGTH: 22
<212> TYPE: DNA
<213> ORGANISM: Artificial Sequence
<220> FEATURE:
<223> OTHER INFORMATION: Oligo 3 reverse primer

<400> SEQUENCE: 28
cagcgagccc tactcaaatt ag                                                  22

<210> SEQ ID NO 29
<211> LENGTH: 21
<212> TYPE: DNA
<213> ORGANISM: Artificial Sequence
<220> FEATURE:
<223> OTHER INFORMATION: 18S forward primer

<400> SEQUENCE: 29
agtccctgcc ctttgtacac a                                                   21

<210> SEQ ID NO 30
<211> LENGTH: 19
<212> TYPE: DNA
<213> ORGANISM: Artificial Sequence
<220> FEATURE:
<223> OTHER INFORMATION: 18S reverse primer

<400> SEQUENCE: 30
cgatccgagg gcctcacta                                                      19
```